(12) United States Patent
Moskowitz

(10) Patent No.: US 11,418,467 B2
(45) Date of Patent: Aug. 16, 2022

(54) METHOD FOR DELIVERY OF AN ENCODED EMS PROFILE TO A USER DEVICE

(71) Applicant: Aebeze labs, Palo Alto, CA (US)

(72) Inventor: Michael Phillips Moskowitz, Palo Alto, CA (US)

(73) Assignee: Get Together, Inc., Berkeley, CA (US)

( * ) Notice: Subject to any disclaimer, the term of this patent is extended or adjusted under 35 U.S.C. 154(b) by 340 days.

(21) Appl. No.: 16/655,265

(22) Filed: Oct. 17, 2019

(65) Prior Publication Data

US 2020/0053030 A1  Feb. 13, 2020

Related U.S. Application Data

(63) Continuation-in-part of application No. 16/570,770, filed on Sep. 13, 2019, which is a continuation-in-part of application No. 16/403,841, filed on May 6, 2019, which is a continuation-in-part of application No. 16/282,262, filed on Feb. 21, 2019, which is a continuation-in-part of application No. 16/239,138, filed on Jan. 3, 2019, now Pat. No. 11,157,700, which is a continuation-in-part of application No. 16/159,119, filed on Oct. 12, 2018, now Pat. No. 10,964,423, which is a continuation-in-part of
(Continued)

(51) Int. Cl.
*H04L 51/046* (2022.01)
*G06F 16/9536* (2019.01)
*H04L 67/306* (2022.01)
*G06F 16/9535* (2019.01)
*G06F 40/30* (2020.01)
*G06N 3/08* (2006.01)

(52) U.S. Cl.
CPC ........ *H04L 51/046* (2013.01); *G06F 16/9535* (2019.01); *G06F 16/9536* (2019.01); *G06F 40/30* (2020.01); *H04L 67/306* (2013.01); *G06N 3/08* (2013.01)

(58) Field of Classification Search
CPC . H04L 51/046; H04L 67/306; G06F 16/9535; G06F 16/9536; G06F 40/30; G06N 3/08; G10L 25/63
See application file for complete search history.

(56) References Cited

U.S. PATENT DOCUMENTS 7,733,224 B2  6/2010  Tran
10,019,962 B2  7/2018  Lin et al.
(Continued)

*Primary Examiner* — Eric Yen
(74) *Attorney, Agent, or Firm* — Patent Ventures, LLC

(57) ABSTRACT

The current invention describes a method and system for imposing a dynamic sentiment vector to an electronic message. In one embodiment of the invention, the method comprises of receiving a text input comprising message content from an electronic computing device associated with a user. The message content is further parsed and comprised in the text input for emotionally-charged language, assigned a sentiment value, based on the emotionally-charged language, from a dynamic sentiment value spectrum to the text input. Additionally, based on the sentiment value, imposing a sentiment vector, corresponding to the assigned sentiment value, to the text input, the imposed sentiment vector rendering a sensory effect on the message content designed to convey a corresponding sentiment.

21 Claims, 34 Drawing Sheets

Related U.S. Application Data application No. 15/959,075, filed on Apr. 20, 2018, now Pat. No. 10,682,086, which is a continuation-in-part of application No. 15/702,555, filed on Sep. 12, 2017, now Pat. No. 10,261,991.

(56) References Cited

U.S. PATENT DOCUMENTS

| | | | |
|---|---|---|---|
| 10,732,722 B1* | 8/2020 | Heraz | G06F 40/30 |
| 10,977,907 B1 | 4/2021 | Zalewski et al. | |
| 2005/0094779 A1* | 5/2005 | Kleinfelter | H04M 3/537 |
| | | | 379/88.12 |
| 2007/0185881 A1* | 8/2007 | Vienneau | G06F 16/2343 |
| 2010/0056222 A1* | 3/2010 | Choi | H04M 1/0247 |
| | | | 455/566 |
| 2012/0004511 A1* | 1/2012 | Sivadas | H04N 1/00307 |
| | | | 600/300 |
| 2012/0323890 A1* | 12/2012 | Dixon | G06Q 10/06311 |
| | | | 707/722 |
| 2013/0072169 A1* | 3/2013 | Ross | G16H 10/60 |
| | | | 455/414.1 |
| 2013/0339449 A1* | 12/2013 | Morin | G06F 16/9577 |
| | | | 709/204 |
| 2014/0149884 A1* | 5/2014 | Flynn, III | G06F 3/0488 |
| | | | 715/752 |
| 2014/0172431 A1* | 6/2014 | Song | G06F 16/433 |
| | | | 704/275 |
| 2015/0097755 A1* | 4/2015 | Kim | G06F 1/1641 |
| | | | 345/1.3 |
| 2015/0178915 A1* | 6/2015 | Chatterjee | G06F 16/58 |
| | | | 382/128 |
| 2015/0296323 A1* | 10/2015 | Wu | H04W 4/70 |
| | | | 455/414.1 |
| 2015/0310093 A1* | 10/2015 | Kim | G06F 16/287 |
| | | | 707/737 |
| 2016/0117597 A1* | 4/2016 | Ono | A61M 21/00 |
| | | | 706/52 |
| 2016/0162807 A1* | 6/2016 | Smailagic | G10L 25/63 |
| | | | 706/12 |
| 2016/0212466 A1* | 7/2016 | Nauseef | H04N 21/4223 |
| 2017/0188928 A1* | 7/2017 | Tanriover | A61B 5/14551 |
| 2017/0205240 A1* | 7/2017 | Nakamura | G01C 21/3484 |
| 2017/0324785 A1* | 11/2017 | Taine | H04L 67/20 |
| 2018/0077095 A1* | 3/2018 | Deyle | G10L 25/63 |
| 2020/0028810 A1* | 1/2020 | Werner | G06K 9/00302 |
| 2020/0104417 A1* | 4/2020 | Fox | G06F 16/958 |
| 2021/0012871 A1 | 1/2021 | Hagen et al. | |
| 2021/0274283 A1* | 9/2021 | Ali | A61F 11/14 |

* cited by examiner

based on the sentiment value, imposing a sentiment vector, corresponding to the assigned sentiment value, to the text input, the imposed sentiment vector rendering a sensory effect on the message content designed to convey a corresponding sentiment — S140 the sensory effect rendered by the sentiment vector includes one of color change of a component of the message content, change in text font of a component of the message content, audio effect, haptic effect, and graphical addition to the message content — S141 the sentiment vector imposed to the text input is a voice accompaniment — S142

*FIGURE 8D*

FIGURE 22 selecting at least one EMS for the user, said EMS indicating a granular assessment of at least one of a feeling, sensation, mood, mental state, emotional condition, or physical status of the user; 

choosing an audio-based digital therapeutic personalized to the user based on at least one of a stored message coupled to the selected EMS; and 

delivering said audio-based digital therapeutic to at least one of a user's device (mobile device, wearable, smart watch, tablet, desktop, laptop) or home entertainment system in communication with at least one of the user's device or a voice-activated Internet-of-Things (IoT) hub. 

FIGURE 23B fast-capturing of at least one EMS for the user based on at least one of a user-plotted point on at least one of a displayed mood map or mood wheel or user-selected from a menu, said EMS indicating an assessment of at least one of a feeling, sensation, mood, mental state, emotional condition, or physical status of the user and categorized as at least one of Dopamine, Serotonin, Epinephrine, Norepinephrine, Oxytocin, or GABA neurotransmitters; 

delivering said GCT to at least one of a user's device (mobile device, wearable, smart watch, tablet, desktop, laptop, headphones, speaker, or smart speaker) or home entertainment system in communication with at least one of the user's device or a voice-activated Internet-of-Things (IoT) hub; and 

wherein the GCT is selected from a store of EMS-specific GCT and is at least one of a suggestion or recommendation for the user to perform a task with clinical-consensus benefits to address at least one of the EMS and improve at least one of the associated neurotransmitters. 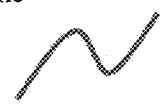

1602

1602

US 11,418,467 B2

METHOD FOR DELIVERY OF AN ENCODED EMS PROFILE TO A USER DEVICE

TECHNICAL FIELD

This invention relates generally to the field of electronic communications and the transmittance of such communications. More specifically, the invention discloses a new and useful method for delivering a therapeutic through an ecosystem of digital content based on a user-mapped EMS.

BACKGROUND

In the past few decades, the availability and use of electronic computing devices, such as desktop computers, laptop computers, handheld computer systems, tablet computer systems, and cellular phones have grown tremendously, which provide users with a variety of new and interactive applications, business utilities, communication abilities, and entertainment possibilities.

One such communication ability is electronic messaging, such as text-based, user-to-user messages. Electronic messaging has grown to include a number of different forms, including, but not limited to, short message service (SMS), multimedia messaging service (MMS), electronic mail (e-mail), social media posts and direct messages, and enterprise software messages. Electronic messaging has proliferated to such a degree that it has become the primary mode of communication for many people.

While electronic messaging can be a particularly efficient mode of communication for a variety of reasons—instant delivery, limitless distance connectivity, recorded history of the communication—electronic messaging does not benefit from the advantages of in-person communication and telecommunication. For example, when communicating via telecommunication, a person can adjust, alter, or augment the content of their message to an intended recipient through tone, volume, intonation, and cadence. When communicating in-person, or face-to-face, a person can further enhance or enrich their spoken words with eye contact and shift of focus, facial expressions, hand gestures, body language, and the like. In electronic messaging, users lack these critically important signals, clues, and cues, making it difficult for people to convey the subtler aspects of communication and deeper intent. As a result, issues of meaning, substance, and sentiment are often lost or confused in electronic messages, which can, and very often does, result in harmful or damaging misunderstandings. Miscommunications can be particularly damaging in interpersonal and business relationships.

Another unintended effect of our overreliance on electronic communication is the impairment of emotional and mental health. In a recent article published in the American Journal of Psychiatry, Dr. Jerald Block wrote "technology addiction is now so common that it merits inclusion in the Diagnostic and Statistical Manual of Mental Disorders, the profession's primary resource to categorize and diagnose mental illnesses." He went on to further state that the disorder leads to anger and depression when the tech isn't available, as well as lying, social isolation and fatigue. Our devices and experiences from said devices (receiving likes, comments and shares on social media) are in essence a drug dealer and drugs, respectively: Having the capability of doling out the same kind of dopamine hit as a tiny bump of cocaine. In effect, creating the typical addiction/dependency vicious cycle and all of the attendant consequences.

According to psychotherapist, Nancy Colier, author of "The Power of Life", "We are spending far too much of our time doing things that don't really matter to us . . . [and become] disconnected from what really matters, from what makes us feel nourished and grounded as human beings." Based on her findings, the average person checks their smartphones 150 times per day, or every six minutes. Furthermore, the average young adult sends on average 110 texts per day and 46% of respondents checked that their devices are something that they couldn't live without.

With this kind of digital ubiquity, it is becoming readily apparent that any solution to the problem involving curtailing or augmenting user behavior is not a realistic approach. Current approaches espoused by experts involve any one of, or combination of, the following: Downloading an app (Moment, Alter, etc.) that locks or limits phone usage upon reaching a pre-specified limit; disabling notifications from your phone settings; keeping the blue-hued light of your smartphone away from your place of rest; and even buying and carrying around a dummy phone.

There is a void for a solution that takes into account ubiquitous usage and provides delivery of pro-mental and emotional health content—personalized to the user, much like the way therapeutics have become narrowly tailored—to counter all of the digital-mediated ill effects plaguing our society. These effects will only logarithmically grow as we transition into the IoT era—where we will be exposed to thousands of internet-enabled objects (each capable of delivering contextualized analytics and provisioning) as part of our day-to-day living. Finally, there is a void in the market for delivering hyper-personalized digital-based therapeutics based on a higher-resolution assessment of an EMS (a more dynamic EMS or dEMS). A dynamic assessment based on a multi-correlate coordinate system (mood map) that allows users to plot as a single point along at least two correlates of behavior—resulting in a push of hyper-personalized digital content with therapeutic value to reinforce or counter the user-mapped dynamic assessment.

There is a void for fast-capture input modality for quick-assessment of an EMS and/or associated neurotransmitter requiring addressing. Furthermore, there is a void in the art combining this fast-capture for digital delivery of a design-rich visual asset with short suggestions or recommendations to address the EMS and/or associated neurotransmitter to achieve an acute psychological response. Finally, there is a void in the art combining this fast-capture for digital delivery of more substantive, textual based generalized clinician tips to achieve acute or longitudinal psychological/behavioral responses.

Moreover, there is a void in the art for a method for delivering an encoded mood or EMS profile of a user to a user device—in at least one of a logged-on, logged-off, rested, or locked state.

SUMMARY

Disclosed is a method and system for imposing a dynamic sentiment vector to an electronic message. In one embodiment of the invention, the method comprises: receiving a text input comprising message content from an electronic computing device associated with a user; parsing the message content comprised in the text input for emotionally-charged language; assigning a sentiment value, based on the emotionally-charged language, from a dynamic sentiment value spectrum to the text input; and, based on the sentiment value, imposing a sentiment vector, corresponding to the assigned sentiment value, to the text input, the imposed sentiment vector rendering a sensory effect on the message content designed to convey a corresponding sentiment.

In another embodiment of the invention, the method comprises: receiving a text input comprising message content from an electronic computing device associated with a user; converting the message content comprised in the text input received from the electronic computing device into converted text in a standardized lexicon; parsing the converted text for emotionally-charged language; generating a sentiment value for the text input from a dynamic sentiment value spectrum by referencing the emotionally-charged language with a dynamic library of emotionally-charged language; and, based on the sentiment value, imposing a sentiment vector to the text input, the imposed sentiment vector rendering a sensory effect on the message content designed to convey a corresponding sentiment.

For example, in one application of the invention, a user can write and submit a text message on the user's cellular phone for delivery to the user's best friend. After receiving the text message, the invention can analyze the message content of the text message and determine, based on the verbiage, syntax, and punctuation within the message content, that the user is attempting to convey excitement through the text message. The invention can then apply a visual filter of red exclamation points or other illustrative, performative, or kinetic attributes to the text message, indicating the excitement of the user, before the text message is delivered to the user's best friend.

In another example of one application of the invention, a user can write and submit a direct message through a social media application (e.g., Instagram, Facebook, SnapChat) on the user's mobile phone for delivery to a second user. After receiving the direct message, the invention can use a camera built into the user's mobile phone to capture an image of the user's face and analyze aspects of the user's face (e.g., curvature of the lips, motion of the eyes, etc.) to determine the user's mood or expression. Based on the user's mood or expression, the invention can then apply a vibration pattern to the direct message before the direct message is delivered to the second user.

In another object of the invention, sentiment and cues of the users emotional or mental state is not gleamed by referencing a parsed user input against a dynamic library of emotionally-charged language to generate a sentiment value and vector for overlaying the said input. Rather, the emotional and mental state (EMS) of the user is chosen by the user or determined by the system based on user engagement with the interface or content. Once the EMS of the user is defined, carefully curated and efficacious content is delivered to the user to combat the defined EMS.

In one aspect, a method is provided for delivering a digital therapeutic, specific to a user-chosen emotional or mental state (EMS), the method comprising the steps of: recognizing at least one EMS selected by the user from a plurality of EMS, the selected EMS indicating at least one of a feeling, sensation, type of discomfort, mood, mental state, emotional condition, or physical status of the user. Once the EMS is defined, the method then calls for pushing a primary-level message personalized to the user based on at least one stored message coupled to the selected EMS. Finally, pushing at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message. The primary and secondary-level messages may contain at least one of a text, image, sound, video, art asset, suggested action or recommended behavior. The efficaciousness or therapeutic value of the primary or secondary messages are validated by at least one—and typically two—independent sources of clinical research or peer-reviewed science, as verified by a credentialed EMS expert.

In another aspect, once the EMS is defined, the method may call for pushing at least a single-level message. The at least single message may contain at least one of a text, image, sound, video, art asset, suggested action or recommended behavior. Again, the efficaciousness or therapeutic value of the primary or secondary messages are validated by at least one—and typically two—independent sources of clinical research or peer-reviewed science, as verified by a credentialed EMS expert.

In yet another aspect, a system is described and claimed for delivering the digital content of validated therapeutic efficacy. The system may comprise an EMS store; at least a primary message prescriber; a processor coupled to a memory element with instructions, the processor when executing said memory-stored instructions, configure the system to cause: at least one EMS from a plurality of EMS in the EMS store to be selected by the user, said selected EMS indicating at least one of a feeling, sensation, type of discomfort, mood, mental state, emotional condition, or physical status of the user; and the at least primary message prescriber pushing a primary-level message personalized to the user based on at least one stored message coupled to the selected EMS.

In yet other aspects, at least a secondary message prescriber is included, wherein the at least secondary message prescriber pushes at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message.

In both aspects (primary or at least secondary message prescribers), the messages or content may contain at least one of a text, image, sound, video, art asset, suggested action or recommended behavior. Much like in the method aspects, the therapeutic value of the messages or content are validated by at least one—and typically two—independent sources of clinical research or peer reviewed published science and selected by a credentialed EMS expert.

In one other aspect, a system and method for generating a more dynamic assessment allowing for more hyper-personalized digital content delivery is provided. Users may plot as a single point on a multi-correlate coordinate system (mood map), wherein each axis represents a unique correlate of behavior and where a single point is a representation of a user-mapped assessment along at least two correlates of behavior, such as active/inactive and positive/negative. Other reinforcing or countering correlates may be provided. Moreover, the mood map may be three-dimensional to include a third correlate of behavior. Finally, the mood map and plotted assessment along the at least two correlates of behavior may be system enabled, as opposed to user-plotted. The system may capture emotional metrics from at least one of a facial image capture, heart/respiration rate, skin conductance, sensor gathered, digital footprint crawled, response to cognitive/physical tasks, engagement to pushed content, etc.

Whether the sentiment or cues are generated by the system or defined by the user, content is being overlaid or delivered to enhance intonation, heighten digital communication, obviate ambiguity, boost mood, support self-esteem, inspire wellness, and aid in the longitudinal and non-interventional care for people in distress or need—leveraging a familiar and known modality (digital devices). According to the claimed invention, a whole ecosystem of receiving and delivering modalities are provided for a host of digital therapeutics. The digital therapeutic offerings—with the aid of Artificial Intelligence (AI), machine learning, and, or predictive EMS assessment tools—may deliver increasingly personalized solutions uniquely tailored to aid each subscriber. Such non-interventional, anonymous, and device-centric solutions are far more appropriate to combat the rising ill-effects of device dependency—rather than pharmaceutical dosing, in-patient treatment, and altering device behavior.

In another aspect, a system and method for delivery of a GCT and/or social-based digital content for achieving acute and/or longitudinal psychological/behavioral responses based on a fast capture of an EMS and/or neurotransmitter.

Moreover, one aspect covers for the delivery of a mood or EMS profile to a user device based on an assessed or determined EMS. This profile is a symbol or color-coded representation displayed on a user device in any device-state for the user to fast-capture state of emotion or mood. In another aspect, this same visual representation of mood profile can be discerned to communicate a digital content or media diet. As a result, a user can quick-capture an contemporaneous or historical diet to better inform future media/content consumption choices.

BRIEF DESCRIPTION OF DRAWINGS

FIGS. 8A, 8B, 8C, and 8D is a graphical representation of one embodiment of the electronic messaging system. are flow diagrams of one embodiment of the electronic messaging system.

FIG. 22 illustrates a method flow chart for delivering an audio-based content (digital therapeutic or digital pharmaceutical) in accordance with an aspect of the invention.

FIG. 23B is an exemplary method flow chart of the GCT delivery in accordance with an aspect of the invention.

DETAILED DESCRIPTION OF DRAWINGS

Numerous embodiments of the invention will now be described in detail with reference to the accompanying figures. The following description of the embodiments of the invention is not intended to limit the invention to these embodiments but rather to enable a person skilled in the art to make and use this invention. Variations, configurations, implementations, and applications described herein are optional and not exclusive to the variations, configurations, implementations, and applications they describe. The invention described herein can include any and all permutations of these variations, configurations, implementations, and applications.

In the following description, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

Figure 1:
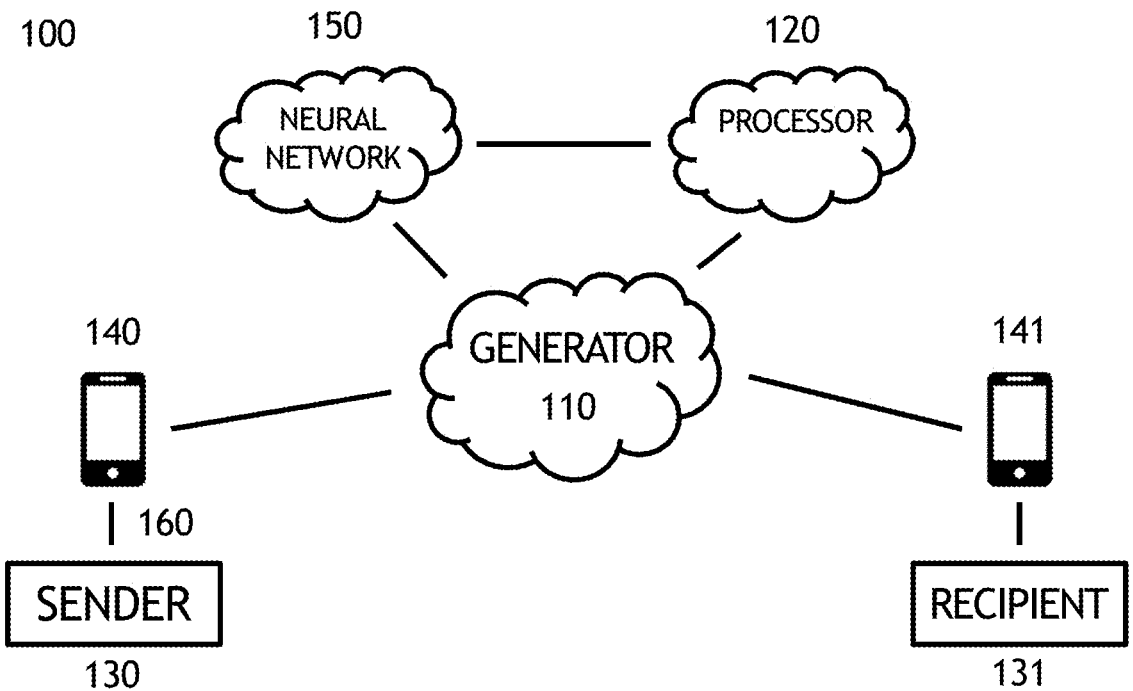
FIG. 1 is a graphical representation of one embodiment of the electronic messaging system.

FIG. 1 depicts a schematic of a system 100 for imposing a dynamic sentiment vector to an electronic message. In one embodiment, a system 100 can include: a sentiment vector generator 110, a processor 120, and an electronic computing device 140 associated with a particular user 130. The sentiment vector generator 110, the processor 120, and the electronic computing device 140 are communicatively coupled via a communication network. The network may be any class of wired or wireless network including any software, hardware, or computer applications that can provide a medium to exchange signals or data. The network may be a local, regional, or global communication network.

The electronic computing device 140 may be any electronic device capable of sending, receiving, and processing information. Examples of the computing device include, but are not limited to, a smartphone, a mobile device/phone, a Personal Digital Assistant (PDA), a computer, a workstation, a notebook, a mainframe computer, a laptop, a tablet, a smart watch, an internet appliance and any equivalent device capable of processing, sending and receiving data. The electronic computing device 140 can include any number of sensors or components configured to intake or gather data from a user of the electronic computing device 140 including, but not limited to, a camera, a heart rate monitor, a temperature sensor, an accelerometer, a microphone, and a gyroscope. The electronic computing device 140 can also include an input device (e.g., a touchscreen or a keyboard) through which a user may input text and commands.

As further described below, the sentiment vector generator 110 is configured to receive an electronic message 160 (e.g., a text input) from the particular user 130 associated with the electronic computing device 140 and run a program 116 executed by the processor 120 to analyze contents of the electronic message, determine a tone or a sentiment that the particular user 130 is expressing through the electronic message 160, and apply a sentiment vector to the electronic message 160, the sentiment vector designed to convey the tone or sentiment determined by the sentiment vector generator 110. The electronic message 160 can be in the form of a SMS message, a text message, an e-mail, a social media post, an enterprise-level workflow automation tool message, or any other form of electronic, text-based communication. The electronic message 160 may also be a transcription of a voice message generated by the particular user 130. For example, in one embodiment, from a messaging application installed on the electronic computing device 140, the user 130 may select to input a voice (i.e., audio) message through a microphone coupled to the electronic computing device 140 or initiate a voice message through a lift-to-talk feature (e.g., the user lifts a mobile phone to the user's ear and the messaging application automatically begins recording a voice message). In this example, the system 100 can generate a transcription of the voice message or receive a transcription of the voice message from the messaging application. After receiving or generating the transcription (i.e., an electronic message), the sentiment vector generator 110 can then analyze the message content within the electronic message, determine the mood or sentiment of the message content, and apply a corresponding sentiment vector to the electronic message, as further described below.

In one embodiment, the system 100 may receive an electronic message 160 in the form of an electroencephalograph (EEG) output. For example, in this embodiment, a user can generate a message using an electronic device communicatively coupled to the user and capable of performing an electroencephalograph to measure and record the electrochemical activity in the user's brain. In this example, the system 100 can transcribe the EEG output into an electronic message 160 or receive a transcription of the EEG output from the electronic device communicatively coupled to the user. After receiving or generating the electronic message 160 from the EEG, the sentiment vector generator 110 can then analyze the message content within the electronic message 160, determine the mood or sentiment of the message content, and apply a corresponding sentiment vector to the electronic message. In one example of this embodiment, a user is connected to an augmented reality (AR) or virtual reality (VR) headset capable of performing an EEG or an equivalent brain mapping technique. The user can generate a message simply by thinking of what the user is feeling or would like to say. The headset can monitor and record these thoughts and feelings using the EEG and transcribe the thoughts and feelings into an electronic message or send the EEG output signals directly to the system 100. The system 100 can then analyze the message content included within the electronic message 160, determine the mood or sentiment of the message content, and apply a corresponding sentiment vector to the electronic message 160, creating a vectorized message. The system 100 can then send the vectorized message to the user's intended recipient (e.g., a recipient that the user thought of).

In one embodiment, the particular user 130 may submit an electronic message 160 through a mobile application (e.g., a native or destination app, or a mobile web application) installed on the particular user's mobile phone or accessed through a web browser installed on the user's phone. In one example of this embodiment, the user accesses the mobile application, submits the electronic message 160 in the form of a text input. The sentiment vector generator 110 can then analyze the message content included within the electronic message 160, determine the mood or sentiment of the message content, and apply a corresponding sentiment vector to the electronic message 160, creating a vectorized message. In this example, the user can then send the vectorized message to the user's intended recipient(s) 131 (e.g., by copying and pasting the vectorized message into a separate messaging application or selecting to export the vectorized message to a separate application, as further described below). In one variation of this embodiment, the user may send the vectorized message to the intended recipient 131 directly through the mobile application. In one embodiment, the user may submit an electronic message 160, or a component of an electronic message (e.g., a single word or phrase within the message content of an electronic message) using a touch input gesture. In one example of this embodiment, the user may submit the electronic message 160 through an electronic computing device by swiping a finger on a touch screen coupled to the electronic computing device 140 in a U-shaped gesture on the electronic message.

In another embodiment, the user may input an electronic message 160 into an entry field of a third-party application such as an email client (e.g., Gmail, Yahoo Mail) or a social media application (e.g., Facebook, Twitter, Instagram). For example, the user may input a message into the body of an email, or into a status update on Facebook. In this embodiment, the system 100 can detect the input of the electronic message 160 into the third-party application and upload the electronic message 160 to the sentiment vector generator 110. The sentiment vector generator 110 can then analyze the message content contained within the electronic message 160, determine the mood or sentiment of the message content, and apply a corresponding sentiment vector to the electronic message 160, creating a vectorized message. The sentiment vector 110 can then replace the electronic message 160 within the third-party application with the vectorized message. Alternatively, the user may select to replace the electronic message 160 with the vectorized message (e.g., by copying and pasting the vectorized message into the entry field).

Figure 2:
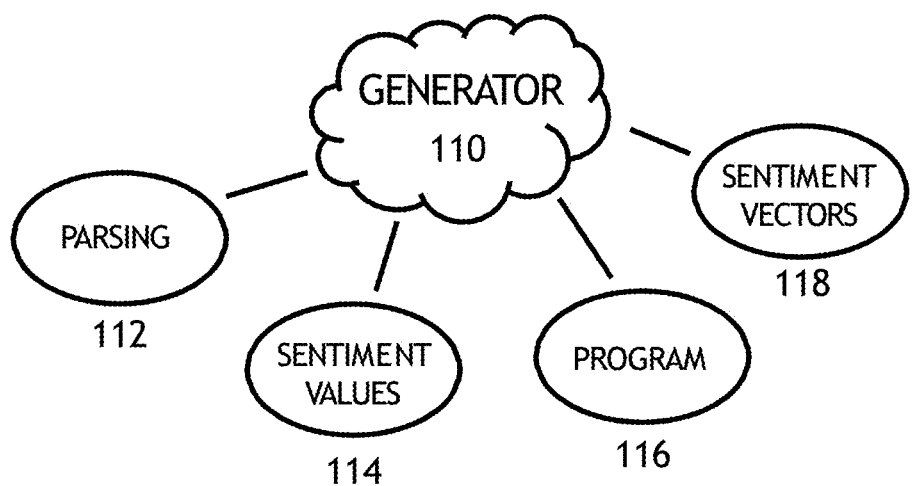
FIG. 2 is a graphical representation of one embodiment of the electronic messaging system.

FIG. 2 depicts a [schematic] of the sentiment vector generator 110. In one embodiment, the sentiment vector generator 110 includes a parsing module 112, a dynamic sentiment value spectrum 114, a program 116, and a library of sentiment vectors. In this embodiment, after receiving an electronic message 160, the sentiment vector generator 110 can activate the program 116 executed by a processor 120 to analyze message content contained within the electronic message 160 using the parsing module 112, the sentiment value spectrum 114, and the library of sentiment vectors, which are discussed in further detail below. Part or all of the sentiment vector generator 110 may be housed within the electronic computing device 140. Likewise, part of all of the sentiment vector generator 110 may be housed within a cloud computing network.

Figure 3A:
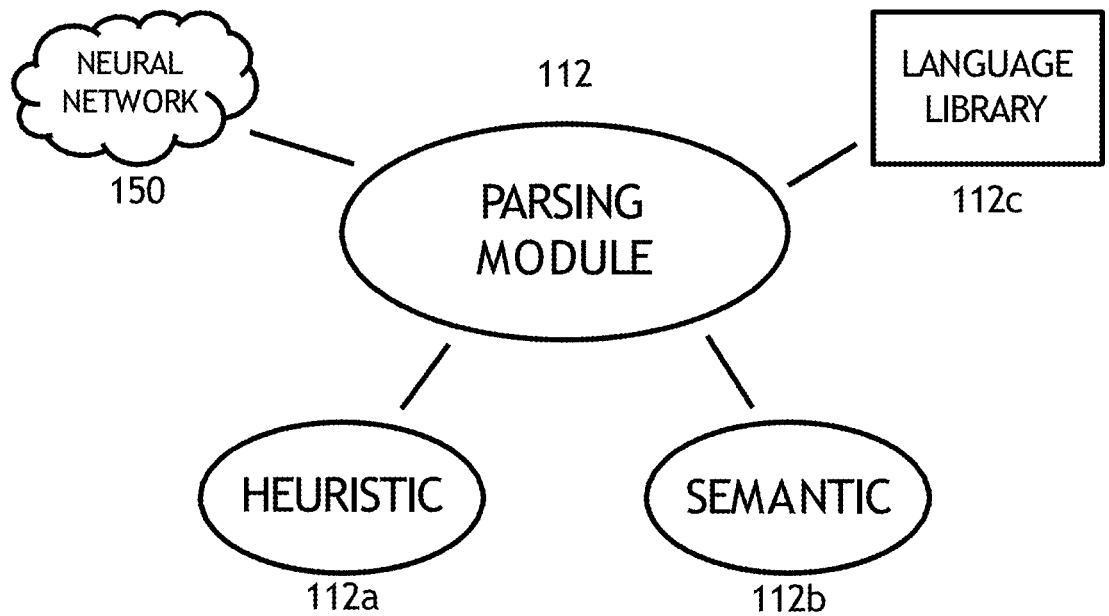
FIGS. 3A and 3B are graphical representations of one embodiment of the electronic messaging system.
Figure 3B:
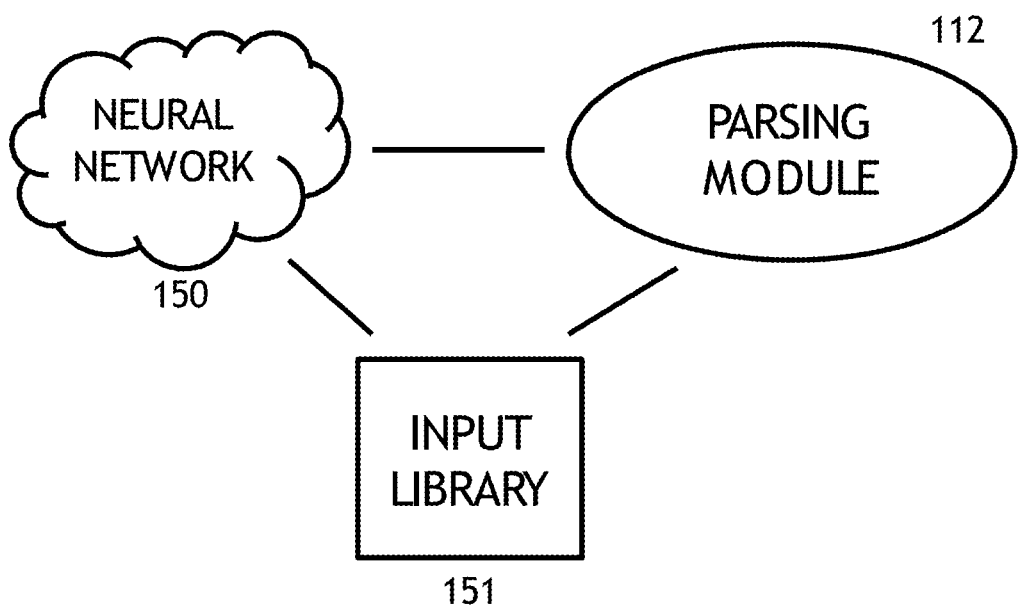

FIG. 3 depicts a schematic of the parsing module 112. The parsing module 112 is configured to parse message content contained within an electronic message 160 received by the sentiment vector generator 110 for emotionally-charged language and determine a sentiment value for the electronic message 160 from the dynamic sentiment value spectrum 114. In one embodiment, the parsing module 112 can include one or both of a heuristic layer 112a and a semantic layer 112b. The heuristic layer 112a is configured to recognize, within the message content contained within the electronic message 160, shorthand script, symbols, and emotional icons (emoticons). For example, the message "r u okay?:(" contains the shorthand character "r" to represent the word "are," the shorthand character "u" to represent the word "you," and the emoticon ":(," representing an unhappy face, each of which the heuristic layer 112a is configured to recognize. The heuristic layer 112a can be further configured to translate recognized shorthand script, symbols, and emoticons into a standardized lexicon. For example, referring back to the previous example, the heuristic layer can translate "u" into "you," "r" into "are," and ":(" into "[sad]." The heuristic layer 112a can thus translate the entire message from "r u okay?:(" to "are you okay? [sad]" in order to compare the sentiments expressed within different messages in a more objective manner and determine the nature of the emotionally-charged language contained within the message of content of the electronic message 160.

The semantic layer 112b is configured to recognize, within the message content contained within the electronic message 160, natural language syntax. For example, in the message "is it ok if we text on WhatsApp?" the construction of the phrases "is it ok" and "WhatsApp?" reflect natural language syntax that can express particular sentiments. "is it ok[?]" can express tentativeness in addition to the objective question that the phrase asks. For reference, inverting and contracting the first two words to create the phrase "it's okay[?]" results in a phrase that can express more confidence. Likewise, the space inserted between "WhatsApp" and "?" can have the effect of "softening" the question mark in comparison to "WhatsApp?" The semantic layer 112b is configured to recognize the use of natural language syntax such as "is it ok" and "WhatsApp?" and can be further configured to translate the recognized natural language syntax into a standardized lexicon. The standardized lexicon can be a standard set of words and terms (e.g., an Oxford dictionary) that the parsing module 112 is able to parse for emotionally-charged language. In one embodiment, the standardized lexicon is a standard set of words and terms with predefined attributes. For example, again referring to the previous example, the semantic layer 112b can translate the entire message from "is it ok if we text on WhatsApp?" to "can[soft] we text on WhatsApp?[soft]" in order to compare the sentiments expressed within different messages in a more objective manner and determine the nature of the emotionally-charged language contained within the message of content of the electronic message 160.

In one embodiment, the parsing module 112 can include a library of emotionally-charged language 112c. In this embodiment, after parsing the message content contained within the electronic message 160, the parsing module 112 can cross-reference the words and terms contained with the message content to the library of emotionally-charged language 112c. The words and terms contained within the library of emotionally-charged language 112c may be tagged with attributes according to the sentiments they most commonly express. For example, the library of emotionally-charged language 112c may include the terms "disastrous," "splendid," "terrible," and "awesome." Within the library of emotionally-charged language 112c, "disastrous" may be tagged with the attribute [bad] or [negative]; "splendid" may be tagged with the attribute [good] or [positive]. In one embodiment, the terms contained within the library of emotionally-charged language 112c may additionally or alternatively be tagged with a numeric value. For example, "disastrous" may be tagged with the attributes [negative; 7], and "terrible" may be tagged with the attributes [negative; 5], indicating that while "disastrous" and "terrible" may express similar "negative" sentiments, "disastrous" is more negative than "terrible." In one embodiment, the parsing module 112 (or, alternatively, any component of the system 100) can dynamically add or remove words or terms to and from the library of emotionally-charged language 112c. The parsing module 112 may use any technique to tag or evaluate the sentiments of emotionally-charged language.

In one embodiment, the library of emotionally-charged language 112c is specific to the particular user 130. In this embodiment, each particular user 130 of the system 100 access a unique library of emotionally-charged language 112c associated only with that particular user. In one variation of this embodiment, the particular user 130 may manually add or remove words and terms to and from the library of emotionally-charged language 112c. In one embodiment of the system 100, the system 100 can be accessed by multiple users. In one variation of this embodiment, the library of emotionally-charged language 112c employed by the parsing module 112 is the same for each user.

In one embodiment of the system 100, the parsing module additionally includes a neural network 150 and a library of inputs 151. In this embodiment, after parsing the message content of an electronic message 160 received by the sentiment vector generator 11, the parsing module 112 can store the electronic message 160 in the library of inputs 151, along with the emotionally-charged language found within the message content and any accompanying attributes, creating a database of messages and their accompanying emotionally-charged language. In this embodiment, the neural network 150 can employ machine learning techniques to analyze this database for patterns and trends in order to dynamically improve the performance of the sentiment vector generator 110. For example, the neural network 150 may determine through the application of an algorithm that the particular user 130 uses the term "disastrous" ten times more often than the particular user 130 uses the term "terrible." Thus, even though "disastrous" may be a more negative term than "terrible" for the average user or person, the neural network can determine that, for the particular user 130, "disastrous" generally carries less emotional weight than "terrible." In this example, the neural network 150 can then update the parsing module 112 and the library of emotionally-charged language accordingly. For example, in the example in which the terms "disastrous" and "terrible" begin as tagged within the library of emotionally-charged language 112c as [negative; 7] and [negative; 5], respectively, the neural network 150 can update the attributes to read [negative; 5] and [negative 7], respectively. In one embodiment, the parsing module 112 can store electronic messages into the library of inputs 151 along with their standardized lexicon conversions.

FIG. 4 depicts graphical representations of the parsing of electronic messages by the parsing module 112. FIG. 4A depicts the parsing of three separate electronic messages 160, "it definitely has given me more time and flexibility and channels creativity differently" 160a, "is it ok if we text on WhatsApp?" 160b, and "Oh u live in Williamsburg" 160c for emotionally-charged language by the parsing module 112. In, this example, in the message content of 160a, the parsing module 112 determines three emotionally-charged words and terms: "definitely has," "and," and "differently;" in the message content of 160b: "ok," "we," and "WhatsApp?" and in the message content of 160c: "u" and "Williamsburg." In one embodiment, as discussed above, after parsing the message content, the parsing module 112 can determine attributes for the emotionally-charged language found in the message content, as depicted by S123 in FIG. 4B. In the example depicted in FIG. 4B, the parsing module 112 tags "definitely has" with [positive, active], "and" with [neutral], and "differently" with [negative]. In one embodiment, as discussed above, the parsing module 112 includes a semantic layer 112b configured to recognize, within the message content contained within the electronic message 160, natural language syntax, as depicted by S122 in FIG. 4B. In the example depicted in FIG. 4B, the semantic layer 112b recognizes the space between "WhatsApp" and "?" in "is it ok if we text on WhatsApp?" as an instance of natural language syntax. In one embodiment, as discussed above, the parsing module 112 includes a heuristic layer 112a configured to recognize, within the message content contained within the electronic message 160, shorthand script, symbols, and emoticons, as depicted by S124 in FIG. 4B. In the example depicted in FIG. 4B, the heuristic layer 112a recognizes "u" as a shorthand term for "you."

Figure 4A:
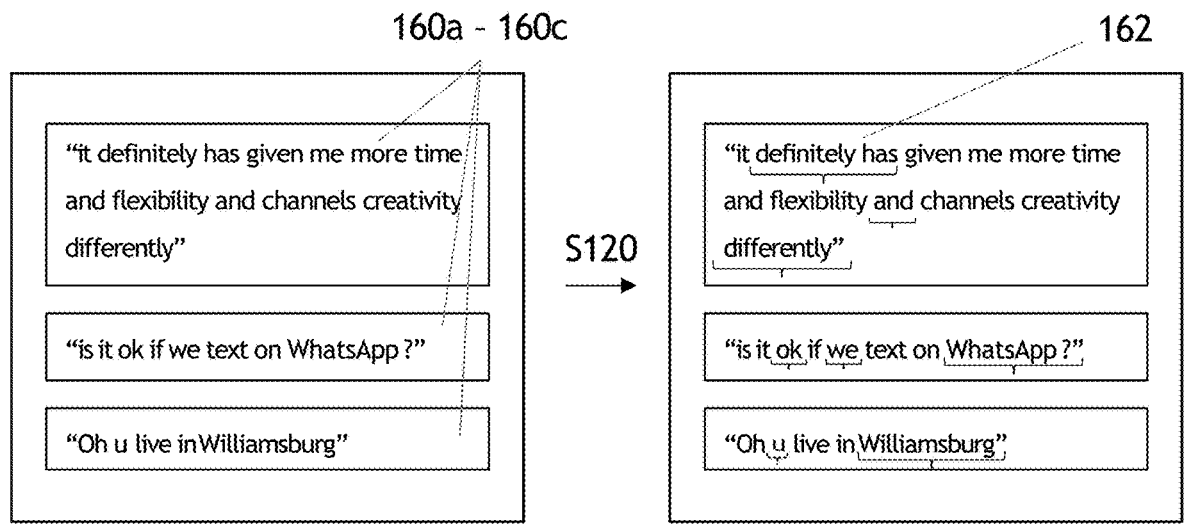
FIGS. 4A, 4B, 4C and 4D are graphical representations of one embodiment of the electronic messaging system.
Figure 4B:
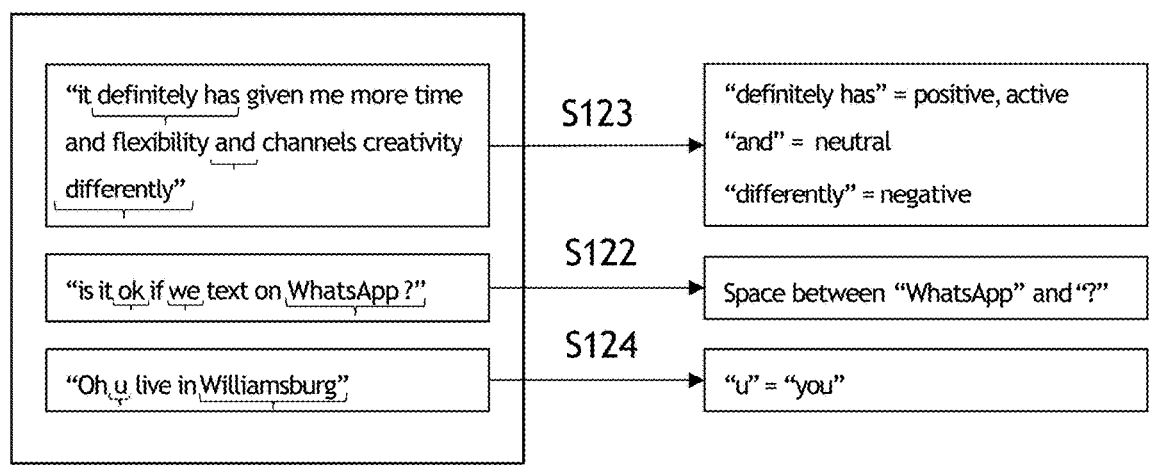
Figure 4C:
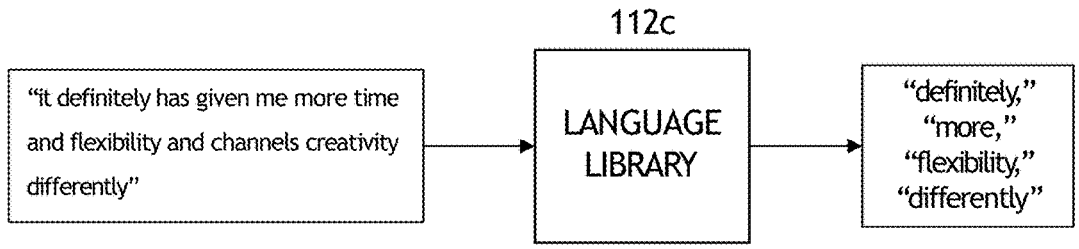
Figure 4D:
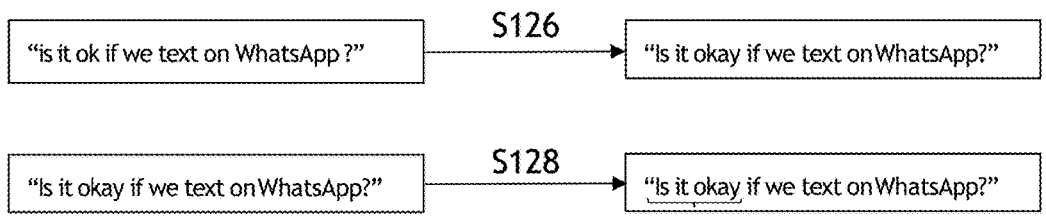

In one embodiment, as discussed above, after parsing the message content contained within the electronic message 160, the parsing module 112 can cross-reference the words and terms contained with the message content to a library of emotionally-charged language 112c, as depicted in FIG. 4C. In the example depicted in FIG. 4C, the parsing module 112 cross-references electronic message 160a with the library of emotionally-charged language 112c and determines that "differently," "more," "flexibility," and "differently" are emotionally-charged words or terms. In one embodiment, as discussed above, before parsing the message content of an electronic message 160, the parsing module 112 can convert the message content into a standardized lexicon, as depicted in FIG. 4D. In the example depicted in FIG. 4D, the parsing module 112 converts "is it ok if we text on WhatsApp?" into the converted text, "is it okay if we text on WhatsApp?" in step S126 before parsing the converted text for emotionally-charged language in step S128.

Figure 5A:
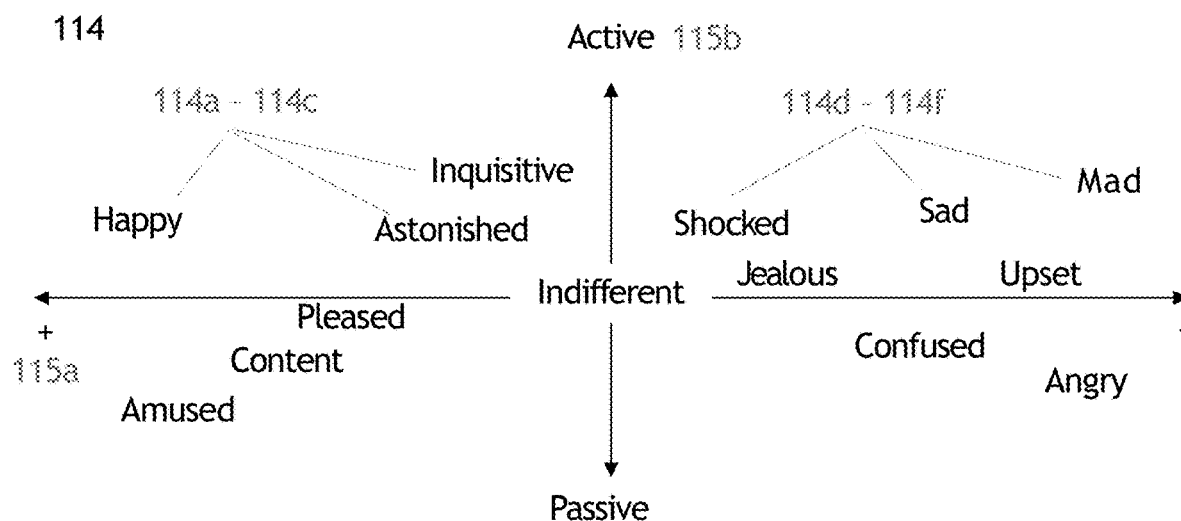
FIGS. 5A, 5B, and 5C are graphical representations of one embodiment of the electronic messaging method.
Figure 5B:
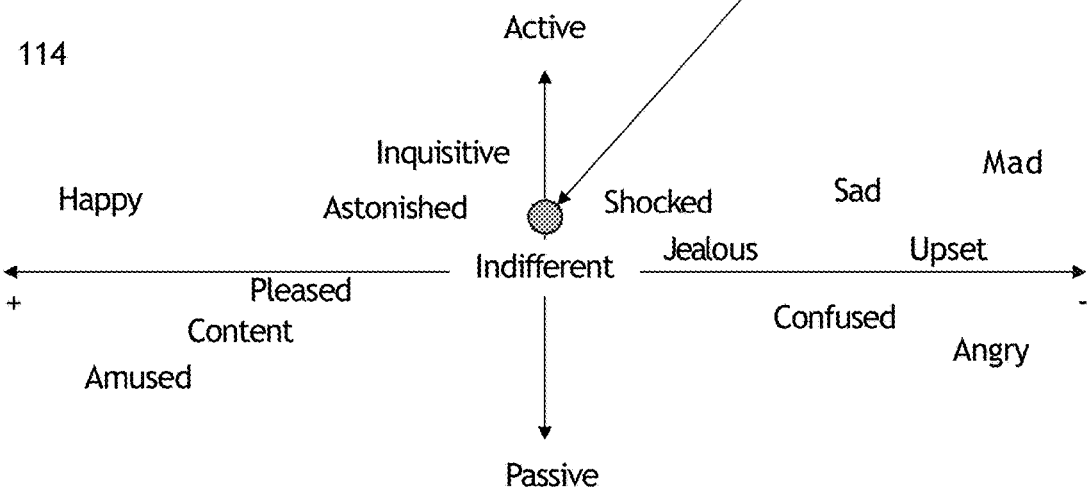
Figure 5C:
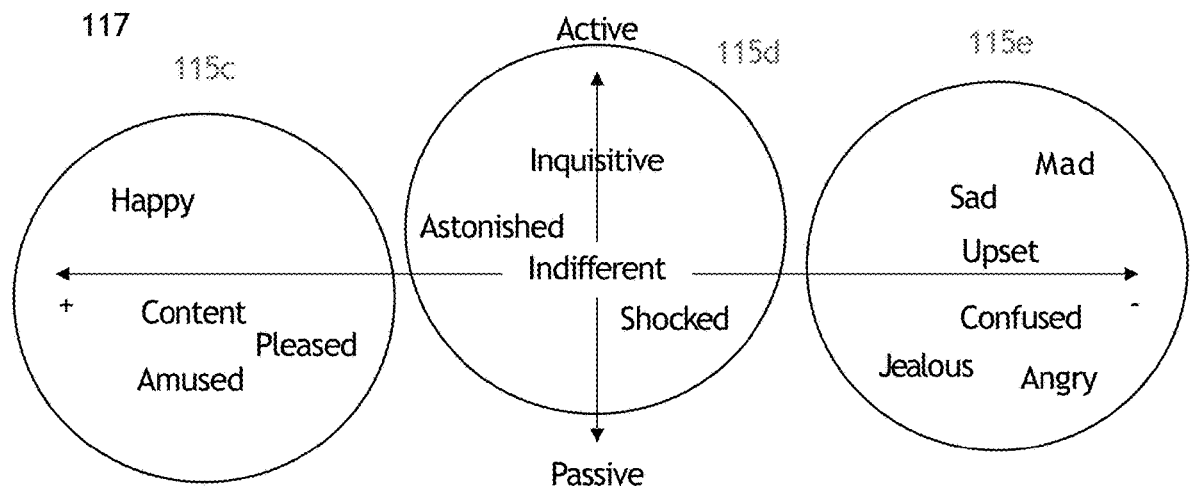

FIGS. 5A, 5B, and 5C depict a graphical representation of a dynamic sentiment value spectrum 114. In one embodiment, after parsing message content of an electronic message 160 for emotionally-charged language, the sentiment vector generator 110 can generate a sentiment value from a dynamic sentiment value spectrum 114 for the electronic message 160. In one variation of this embodiment, the dynamic sentiment value spectrum 114 can be represented as a coordinate system, as depicted in FIG. 5A. In the example depicted in FIG. 5A, the dynamic sentiment value spectrum 114 is a Cartesian coordinate system consisting of two axes: a horizontal axis 115a ranging from positive to negative (henceforth, the positivity axis) and a vertical axis 115b ranging from passive to active (henceforth, the activity axis). In this example, the dynamic sentiment value spectrum 114 consists of a multitude of different sentiments, each occupying a different position on the coordinate system. For example, the sentiments "Happy," "Astonished," and "Inquisitive" (114a-114c, respectively) all occupy the second quadrant of the coordinate system, defined by a positive position on the positivity scale and an active position on the activity scale (i.e., each of these sentiments are determined by the sentiment vector generator 110 to be positive and active sentiments). In this example, the sentiment vector generator considers Inquisitive 114c to be a more active but less positive sentiment than Astonished 114b and Astonished to be a less positive and less active sentiment than Happy 114a. Also, in this example, the sentiments "Shocked," "Sad," and "Mad" (114d-114f, respectively) all occupy the first quadrant of the coordinate system, defined by a negative position on the positivity scale and an active position on the activity scale (i.e., each of these sentiments are determined by the sentiment vector generator to be active and negative sentiments). However, the dynamic sentiment value spectrum 114 need not be a coordinate system. Rather, the dynamic sentiment value spectrum 114 may take on any appropriate form (e.g., a list, a linear scale, etc.). Additionally, the sentiment value spectrum does not need to be dynamic.

In one embodiment, as discussed above, after parsing message content contained within an electronic message 160 for emotionally-charged language, the parsing module 112 can assign attributes to the emotionally-charged language found in the message content of the electronic message 160. In one embodiment, the sentiment vector generator 110 can analyze the emotionally-language and their accompanying attributes to generate a sentiment value from the dynamic sentiment value spectrum 114, as depicted in FIG. 5B. For example, in the example depicted in FIG. 5B, the parsing module 112 can assign each emotionally-charged term found in the message content of an electronic message with respective coordinate values on the positivity and activity axes of the Cartesian coordinate dynamic sentiment value spectrum discussed in the example above. In this example, the sentiment vector generator 110 can take the coordinate position of each emotionally-charged term, calculate an average position of the emotionally-charged terms, and plot the average positon on the dynamic sentiment value spectrum 114 depicted in FIG. 5A. Then, in this example, the sentiment vector generator 110 can generate a sentiment value for the electronic message by determining the sentiment value on the dynamic sentiment value spectrum 114 closest to the average position of the emotionally-charged terms.

In one embodiment, the sentiment vector generator 110 can generate a sentiment value for an electronic message 160 by determining which of the emotionally-charged terms found in the message content of the electronic message carries the most emotional weight. For example, in one embodiment, the parsing module 112 can parse the message content of an electronic message 160 for emotionally-charged language and assign each emotionally-charged term with a positivity scale value, an activity scale value, and an emotional weight value. In this embodiment, the sentiment vector generator 110 can then determine a sentiment value for the electronic message by determining which of the emotionally-charged terms has the highest emotional weight value, and then determining the sentiment value on the dynamic sentiment value spectrum 114 closest to the position of emotionally-charged term with the highest emotional weight value.

In one embodiment, the library of emotionally-charged language 112*c* associates each emotionally-charged term contained within the library with a sentiment value from the dynamic sentiment value spectrum 114. For example, the library of emotionally-charged language 112*c* may associate the words "gleeful," "splendid," and "terrific" with a "happy" sentiment value. In this example, if the message content of an electronic message 160 includes any of the terms "gleeful," "splendid," or "terrific," the sentiment vector generator 110 can generate a "happy" sentiment value for the electronic message 160. However, the sentiment vector generator can generate a sentiment value for an electronic message 160 using any other methodology.

In one embodiment, the particular user 130 may select a sentiment value from the dynamic sentiment value spectrum for an electronic message 160. In one variation of this embodiment, after the parsing module 112 parses the message content of an electronic message 160 submitted by the particular user 130, the sentiment vector generator 110 can generate multiple sentiment values for the electronic message 160 and present the multiple sentiment values for the electronic message 160 to the particular user 130 for selection. For example, after receiving electronic message 160*a* (depicted in FIG. 4A), the sentiment vector generator 110 may generate an "excited" sentiment value and a "melancholy" sentiment value for electronic message 160*a*. In this example, the particular user 130 may be given the choice to pick between the "excited" sentiment value and the "melancholy" sentiment value, in order to further ensure that the proper (i.e., intended) sentiment will be expressed.

In one embodiment, as discussed above, the system 100 includes a neural network 150 and a library of inputs 151 communicatively coupled to the sentiment vector generator 110. In one variation of this embodiment, after generating a sentiment value for an electronic message 160, the sentiment vector generator 110 store the electronic message 160 and its accompanying sentiment value in the library of inputs 151 creating a database of messages and their accompanying sentiment values. In this embodiment, the neural network 150 can employ machine learning techniques to analyze this database for patterns and trends in order to dynamically improve the performance of the sentiment vector generator 110. In one variation of this embodiment, the neural network 150 can dynamically edit or rearrange the dynamic sentiment value spectrum 114. In the rearranged version, the sentiment values have adjusted and coalesced into more discrete sections (115*c*-115*e*). This may reflect that a particular user 130 associated with the rearranged sentiment value spectrum 117 generates messages most of their messages with a similar tone, making the difference between similar sentiments subtler than that of the average person.

Figure 6:
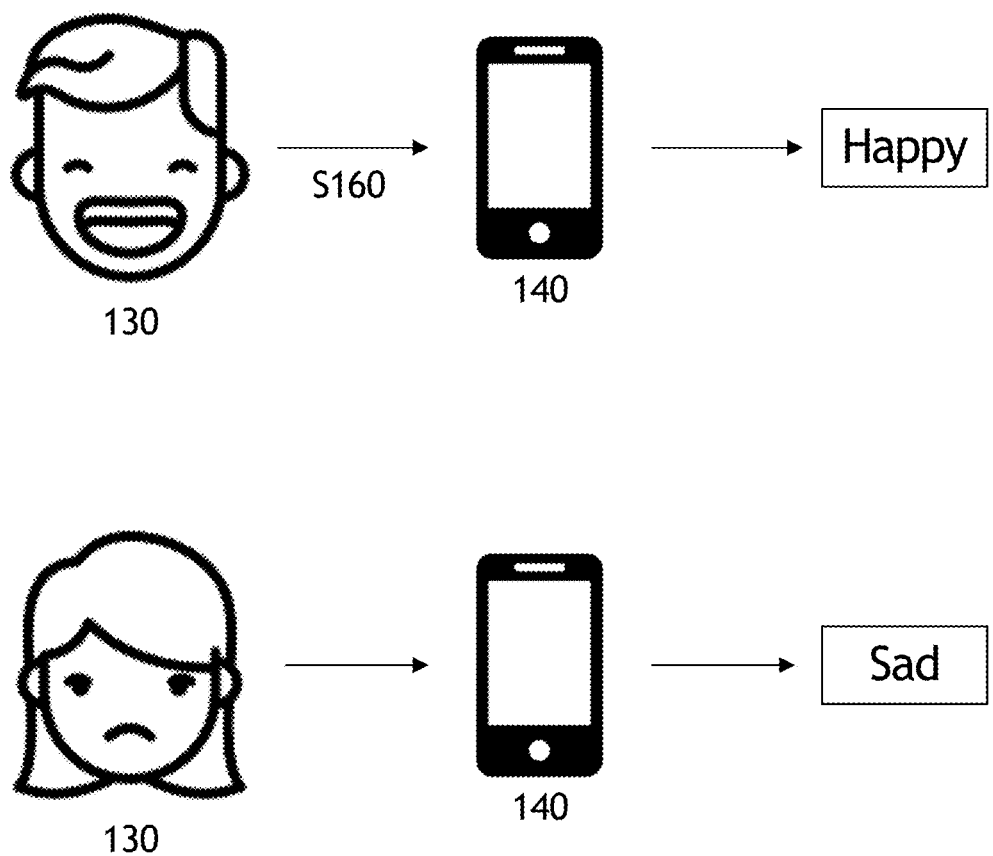
FIG. 6 is a graphical representation of one embodiment of the electronic messaging method.

In one embodiment, the sentiment vector generator 110 can generate a sentiment value for an electronic message 160 at least in part by utilizing information about a particular user 130. For example, in one embodiment, the system 100 can generate sender context associated with a particular user 130. The sender context can include, but is not limited to: social media data associated with the particular user, data obtained from IoT (internet of things) devices associated with the particular user, data obtained from wearable devices associated with the particular user, genetic profile data associated with the particular user, and stress data of the particular user. In one variation of this embodiment, the system 100 can leverage sensors and inputs coupled to an electronic computing device 140 associated with the particular user 130 to generate sender context associated with the particular user 130, as depicted by step S160 in FIG. 6. For example, in the example depicted in FIG. 6, the system 100 can leverage a camera built into a mobile phone associated with the particular user 130 to capture images of the face of the particular user. In this example, the system 100 can then analyze the images of the face of the user (e.g., the eye motion or lip curvature of the user) and determine the mood of the user at the time that the electronic message 160 is generated. The sentiment vector generator 110 can then generate a sentiment value using the determined mood of the user. In one variation of this embodiment, the system 100 can leverage sensors coupled to wearable devices associated with a particular user, such as a smart watch, intelligent contact lenses, or cochlear implants. For example, the system 100 can leverage a microphone built into a cochlear implant to capture the heartrate of a user at the time that the user is generating an electronic message 160. Using the captured heartrate, the sentiment vector generator 110 can then determine a stress level of the user at the time that the user generated the electronic message 160 and generate a sentiment value using the determined stress level of the user. Sender context can additionally or alternatively include: facial expression, motion or gesture, respiration rate, heart rate, and cortisol level.

In another variation of the previous embodiment, the sentiment vector generator 110 can generate a sentiment value for an electronic message 160 at least in part by utilizing information about an intended recipient of the electronic message 160. In this embodiment, after receiving an electronic message 160, the system 100 can determine an intended recipient 131 of the electronic message 160. The system 100 can then generate recipient context associated with the intended recipient 131. The recipient context can include but is not limited to: social media data associated with the intended recipient, data obtained from IoT (internet of things, e.g., a smart home assistant such the Amazon Echo) devices associated with the intended recipient, data obtained from wearable devices associated with the intended recipient, genetic profile data associated with the intended recipient, and stress data associated with the intended recipient. For example, in one embodiment, the system 100 can leverage sensors built into an electronic device 141 associated with the intended recipient to determine a mood of the intended recipient 131 at the time that the electronic message 160 is generated. The sentiment vector generator 110 can then generate a sentiment value for the electronic message 160 based at least in part on the determined mood of the intended recipient 131.

Figure 7A:
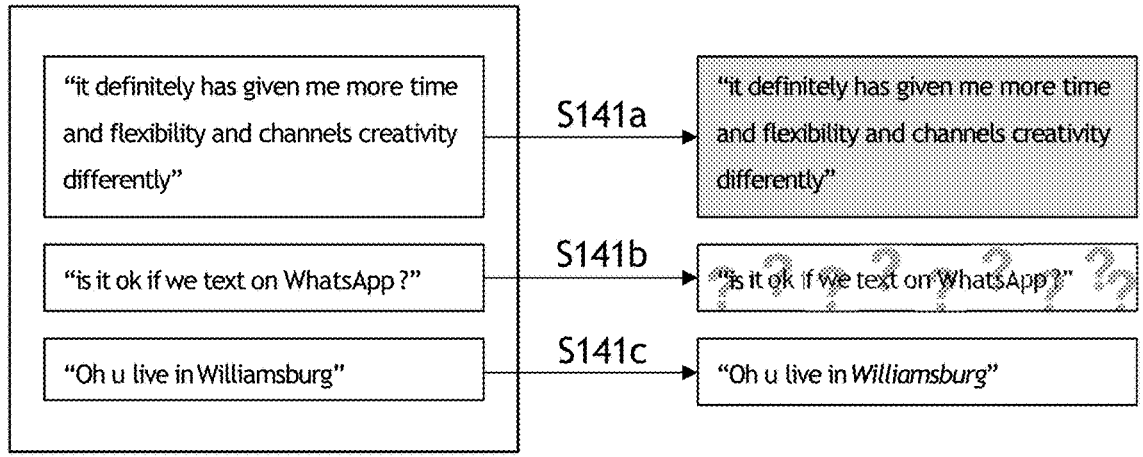
FIGS. 7A and 7B are graphical representations of one embodiment of the electronic messaging system.

After generating a sentiment value for an electronic message 160, the sentiment vector generator 110 can then select a sentiment vector from a library of sentiment vectors 118, the selected sentiment vector designed to convey a sentiment corresponding to the generated sentiment value, and impose the selected sentiment vector to the electronic message 160, as depicted in FIG. 7. The library of sentiment vectors 118 can include but is not limited to: a color change of a component of the message content, a change in the text font of a component of the message content, an audio effect, a haptic effect, and a graphical addition to the message content. For example, in one embodiment, after generating a "mad" sentiment value, the sentiment vector generator 110 may change the background of the electronic message 160, as depicted by step S141$a$ in FIG. 7A, such as changing the background of the electronic message 160 to red to reflect the mad sentiment. Or, for example, in one variation of this embodiment, the sentiment vector generator 110 may opt to highlight only key words or terms in red, or change the fonts of key words or terms to red. The sentiment vector generator 110 can impose any sort of color change to the electronic message 160 in order to convey a corresponding sentiment.

In one embodiment, for example, after generating an "inquisitive" sentiment value for an electronic message 160, the sentiment vector generator 110 may impose a graphic onto the electronic message 160, as depicted by step 141$b$ in FIG. 7A, such as adding question mark graphics to the background of the electronic message 160. In one variation of this example, the sentiment vector generator 110 can add one question mark to the end of the message content of the electronic message 160 in a font size that is larger than the font size of the rest of the message content. In another variation of this example, the sentiment vector generator 110 may impose a .gif file to the background of electronic message 160, in which one question mark grows and shrinks in periodic intervals. The sentiment vector generator 110 can impose any sort of static or dynamic graphic to the electronic message 160 in order to convey a corresponding sentiment.

In one embodiment, for another example, after generating a "judgmental" sentiment value for an electronic message 160, the sentiment vector generator 110 can edit the font of a key word in the message content, as depicted by step S141$c$ in FIG. 7A, such as italicizing one of the words contained in the message content. Such font effects can include, but are not limited to, italicizing the font, changing the size of the font, bolding, underlining, and changing the spacing between characters, words, and lines. The sentiment vector generator 110 can impose any sort of font change to the electronic message 160 in order to convey a corresponding sentiment.

In one embodiment, the sentiment vector generator 110 can impose an animated character or personality to the electronic message 160, or transpose the electronic message 160 into a graphic of an animated character or personality. For example, in one variation of this embodiment, the library of sentiment vectors 118 may include a series of the same animated character (take, for example, an animated llama or chicken) performing various actions associated with various corresponding sentiments. For example, the library of sentiment vectors 118 may include a static or dynamic graphic of an animated chicken stomping with red eyes (expressing anger), another graphic of the animated chicken laying in a hammock and basking in the sun (expressing contentedness), and another graphic of the animated chicken blowing a kiss (expressing affection). In this example, after generating an "anger" sentiment value for an electronic message 160, the sentiment vector generator 110 can transpose the electronic message into the graphic of the animated chicken stomping and saying the message content of the electronic message 160.

In one embodiment, the sentiment vector generator 110 can impose a haptic effect onto an electronic message 160. For example, after generating an "anger" sentiment value for an electronic message 160, the sentiment vector generator 110 can impose a vibration or vibration pattern onto the electronic message 160, as depicted by step S141$d$ in FIG. 7B, such as three short vibrations. In another example, after generating a "contented" sentiment value for an electronic message 160, the sentiment vector generator 110 can impose one long and muted vibration to the electronic message 160. The sentiment vector generator 110 can impose any form of vibration or vibration pattern to an electronic message in order to convey a corresponding sentiment.

In one embodiment, the sentiment vector generator 110 can impose an audio effect onto an electronic message 160. For example, after generating an "unhappy" sentiment value for an electronic message 160, the sentiment vector generator 110 can impose an audio accompaniment onto the electronic message 160, as depicted by step S142 in FIG. 7B, such as protracted "nooo." In another example, the sentiment vector generator 110 can impose a voice accompaniment dictating the message content of the electronic message 160 and stressing key words contained within the message content. The voice accompaniment may stress key words contained within the message content in any number of ways including, but not limited to: increasing or decreasing in volume, changing the intonation of the voice, changing the speed of the voice, or changing the cadence of the voice accompaniment. In one embodiment, the voice accompaniment vector may be a recorded and processed version of the particular user's voice. In one embodiment, the voice accompaniment vector may be the voice of another individual, such as a celebrity, or a combination of the particular user's voice and the voice of another individual.

Figure 7B:
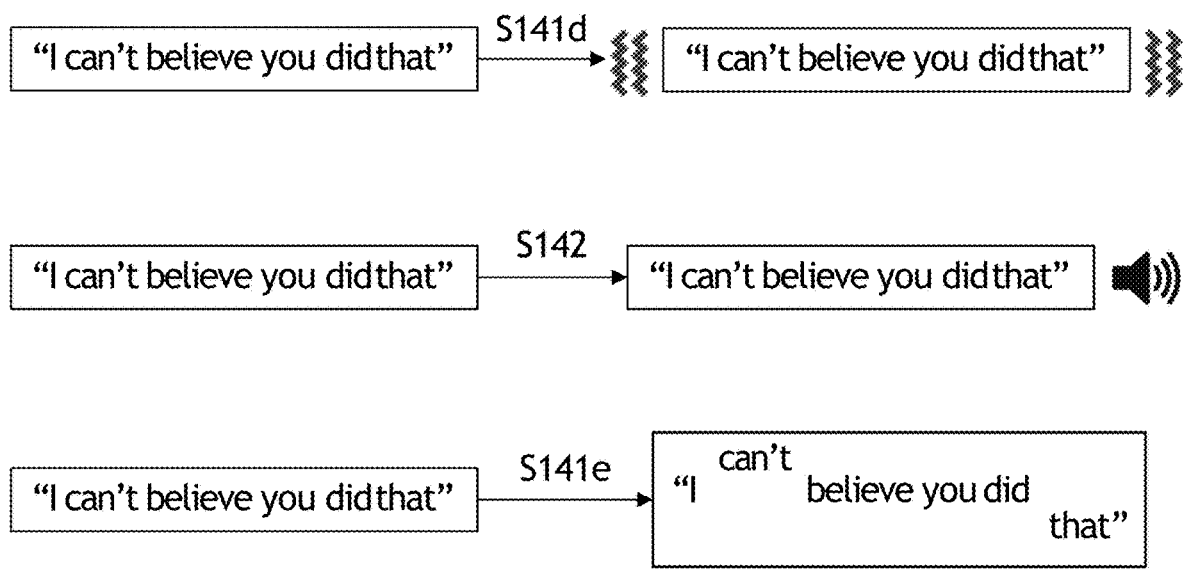
Figure 8A:
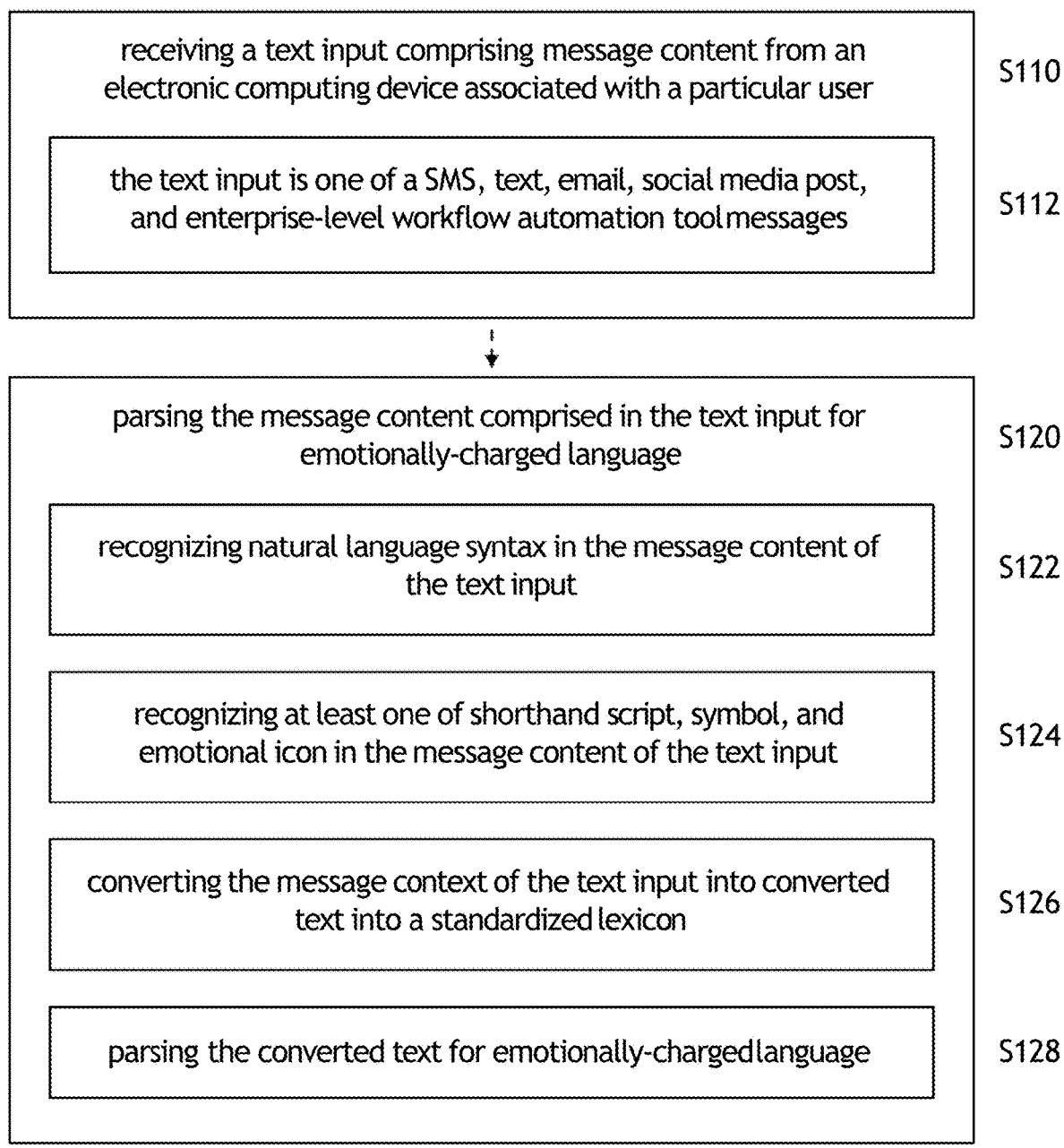
Figure 8B:
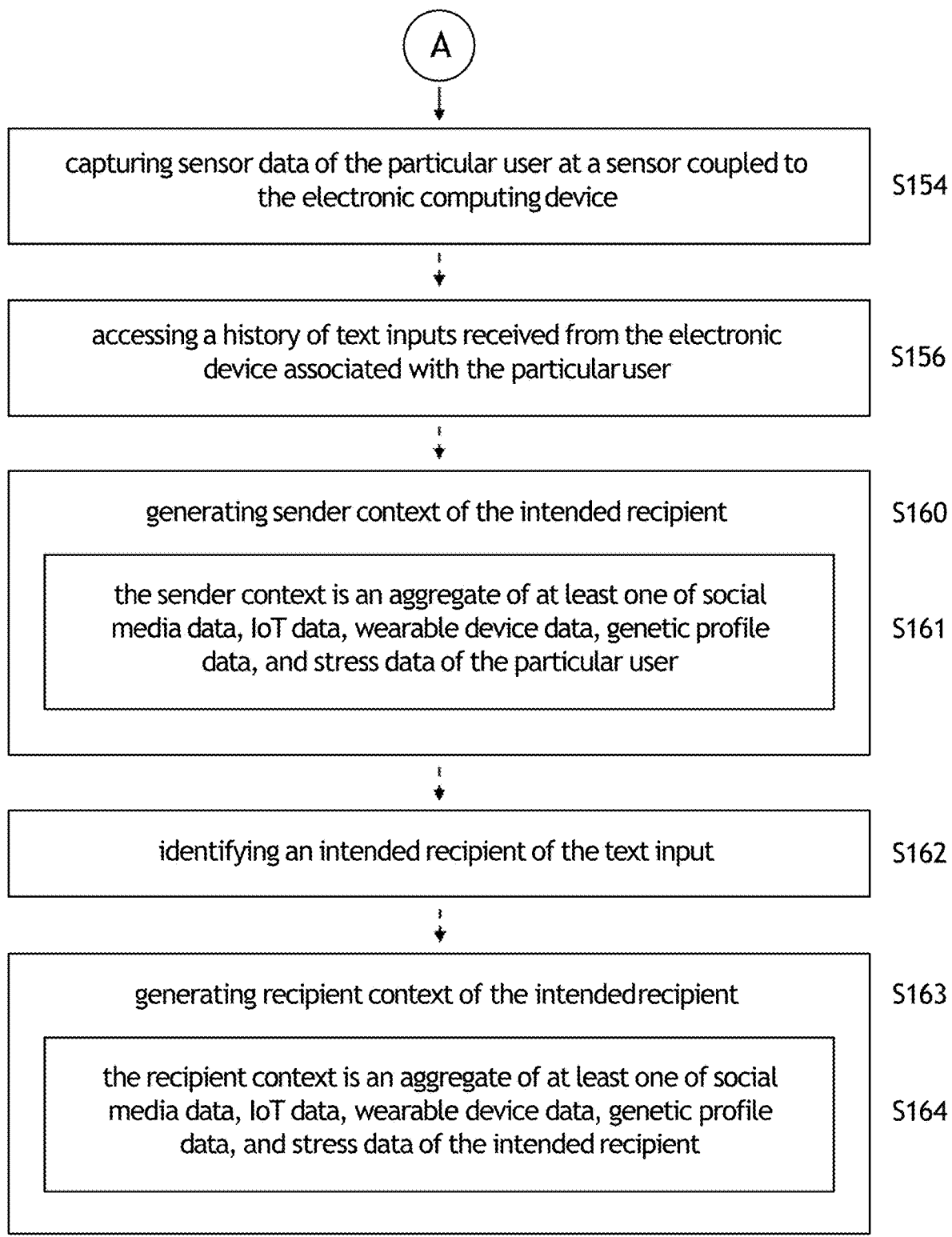
Figure 8C:
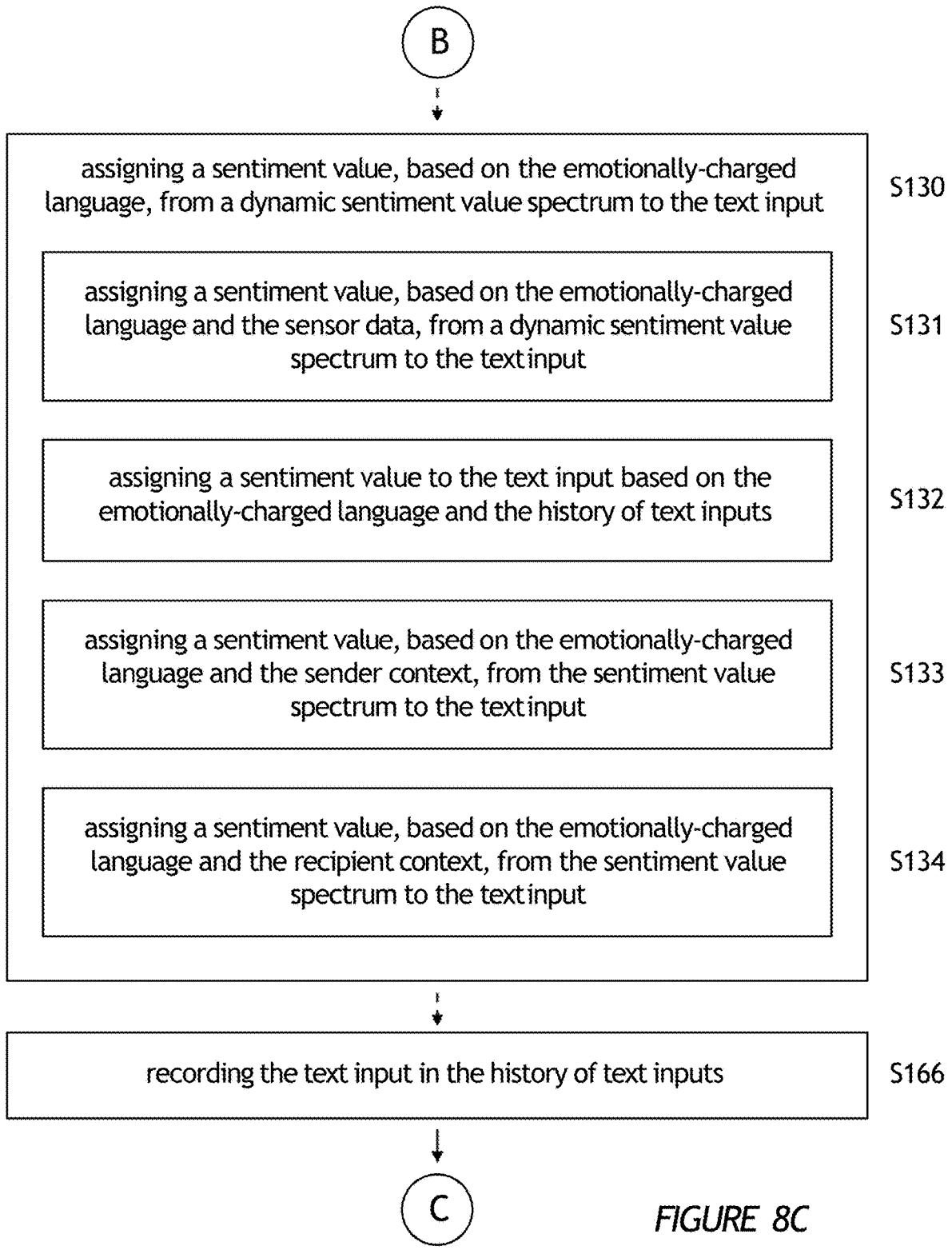

In one embodiment, after generating a sentiment value for an electronic message 160, the sentiment vector generator 110 can impose a vector onto the electronic message 160 that adjusts the position of the words contained with the message content of the electronic message, as depicted by step S141$e$ in FIG. 7B. In one variation of this embodiment, the adjustment of the words contained within the message content is static, such that the words occupy new positions in a static image. In one variation of this embodiment, the adjustment of the words contained within the message content is dynamic, such that the words contained within the message content move within the resulting vectorized message.

In one embodiment, a user may submit sentiment vectors to the sentiment vector generator 110. For example, in one embodiment, a user may submit a picture or graphic design to impose onto the background of an electronic message and select a sentiment value for the picture or graphic design to be associated with. In this example, after generating a sentiment value for an electronic message 160 corresponding to the sentiment value that the user has selected to associate with the picture or graphic design, the sentiment vector generator 110 can impose the picture or graphic design to the background of the electronic message 160 to convey the corresponding sentiment. In another example, in one variation of this embodiment, a user can select a sentiment vector previously included in the library of sentiment vectors 118 and previously associated with a sentiment value and disassociate the sentiment vector from the associated sentiment value, or re-associate the sentiment vector with a different sentiment value. In yet another example, in one variation of this embodiment, a user can select one or more elements from existing sentiment vectors contained within the library of sentiment vectors 118 and combine them to create a new sentiment vector. In this example, the user can also choose a sentiment value to associate with the new sentiment vector. In another example, in one variation of this embodiment, a user can select a sentiment vector by scrolling through a list of sentiment vectors (e.g., a list including options to adjust text weight, height, font, color, highlight, or content animation) using a flicking gesture, within a mobile application, on a touch screen coupled to an electronic computing device.

The sentiment vector generator can include or generate, but is not limited to, sentiment vectors using any combination of the elements of the sentiment vectors described herein. Additionally, environmental conditions and factors for example, but not limited to, wind, heat, humidity, cold may also play a role in generating the sentiment vector.

In one embodiment of the system 100, a user can submit an electronic message 160 to the sentiment vector generator 110 through a mobile application (e.g., a native application), as discussed above. In one variation of this embodiment, the mobile application can store vectorized messages generated by the sentiment vector generator and allow the user to search through the vectorized messages. In this embodiment, the user can search through the vectorized messages using different filters or queries including, but not limited to: mood, color, content, and sentiment. For example, in one embodiment, the user can enter a sentiment as "anger" as a search query, and a graphical user interface of the mobile application can display a list of all of the vectorized messages that the user has created through the sentiment vector generator 110 with a sentiment value corresponding to an "anger" sentiment. In one embodiment, the sentiment vector generator 110 can impose a hyperlink onto an electronic message 160. FIGS. 8A, 8B, 8C, and 8D are flow diagrams of one embodiment of the electronic messaging system.

In an embodiment of the invention, the sentiment vector generator 110 can impose a hyperlink onto an electronic message 160. An imperative function of the sentiment vector is GEEQ (genetics, emotion and electroencephalography) and its capacity to integrate messages and messaging with user movement and thought as well as the ability to pair information with form and performative elements. In a nutshell, our technology will introduce, integrate, account for, and actively utilize GEEQ (Genetics, Emotion, and Electroencephalography). GEEQ, by its very design, integrates and intermingles the beliefs and postulates of Darwin, Mendel, Mendelssohn, Morgan, and Martha Graham.

Figure 9:
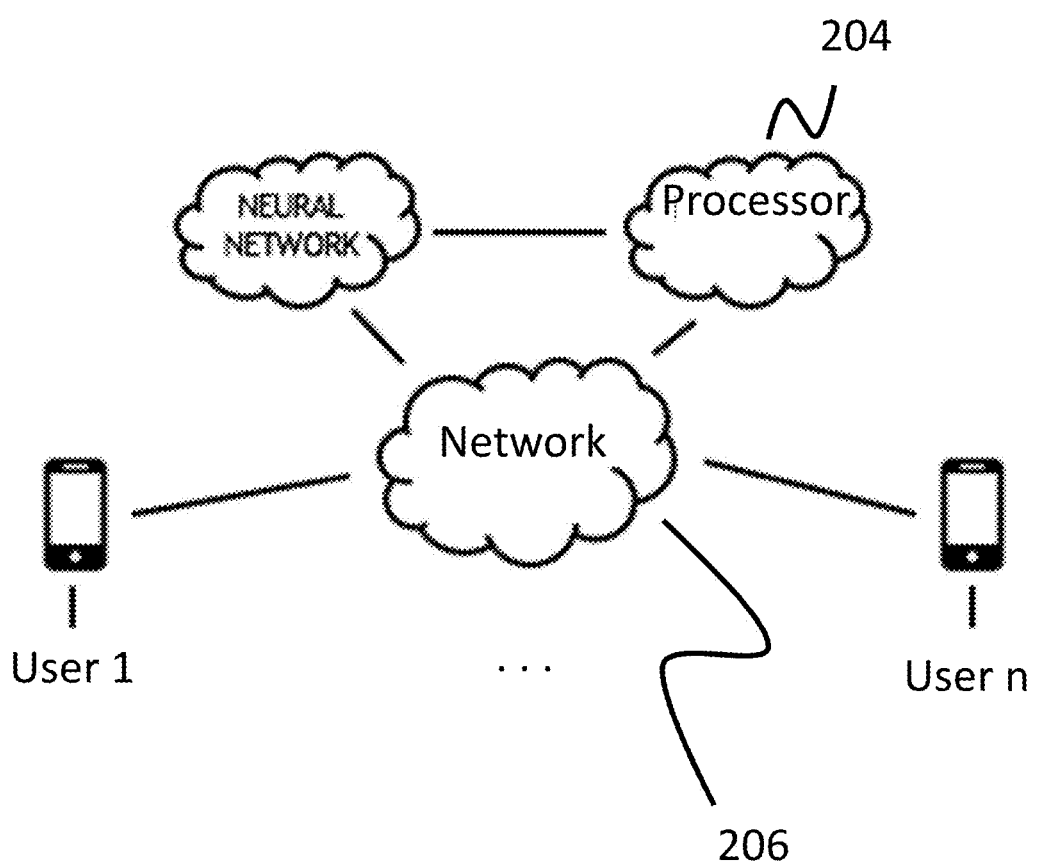
FIG. 9 illustrates a network diagram in accordance with an aspect of the invention.

FIG. 9 illustrates a network diagram of the digital therapeutic system in accordance with an aspect of the invention. As shown, at least one processor 204 is connected to the Internet (network) 206 via either a wireless (e.g. WiFi link) or wired link to an Internet connected router, usually via firewall. The network 206 may be any class of wired or wireless network including any software, hardware, or computer applications that can provide a medium to exchange signals or data. The network 206 may be a local, regional, or global communication network. Various servers 204, such as a remote VCS Internet server, and associated database memory can connect with the at least a user device (1 . . . n). Additionally, various user devices (e.g. Smartphones, tablet computers, laptop computers, desktop computers and the like) can also connect to both the processor-controlled IoT hubs, sensors disposed on the device configured for data gathering, and/or the remote VCS Internet server 204.

As will be discussed, often a plurality of different user devices may be used, but for simplicity this plurality of devices will often be spoken of in the singular form. This use of the singular form is not intended to be limiting, and in general the claims and invention should be understood as operating with a plurality of devices. Although for simplicity, often mobile client computerized devices such as Internet connected versions of the popular Android, iOS, or Windows smartphones and tablets will be used as specific examples of devices, these specific examples are not intended to be limiting. The electronic computing device may include any number of sensors or components configured to intake or gather data from a user of the electronic computing device including, but not limited to, a camera, a heart rate monitor, a temperature sensor, an accelerometer, a microphone, and a gyroscope. The electronic computing device can also include an input device (e.g., a touchscreen or a keyboard) through which a user may input text and commands.

While not shown, note that server, Internet connected storage device and database memory may all be located in the cloud. This is intended to both designate and remind the reader that the server, Internet connected storage device and database memory are in fact operating according to scalable Internet cloud-based methods that in turn operate according to automated service provisioning and automated virtual machine migration methods. As previously discussed, examples of such scalable methods include, but are not limited to, Amazon EC2, Microsoft Windows Azure platform, and the Google App Engine. Thus, for example, server and Internet connected storage device will often be implemented as automatically provisioned virtual machines under a cloud service system that can create a greater or lesser number of copies of server and Internet connected video storage device and associated database memory according to the underlying demands on the system at any given time.

Preferred embodiments may include the addition of a remote server 204 or cloud server to further provide for back-end functionality and support. Any one of the storage or processing may be done on-board the device or be situated adjacent or remotely from the system and connected to each system via a communication network 206. In one embodiment, the server 204 may be used to support user behavior profiling; user history function; predictive learning/analytics; alert function; network sharing function; digital footprint tracking, etc. The remote server 204 may be further configured to authenticate the user and retrieve data of the user, device, and, or network and applies the data against a library of messages, content, validated user information, etc.

Figure 10:
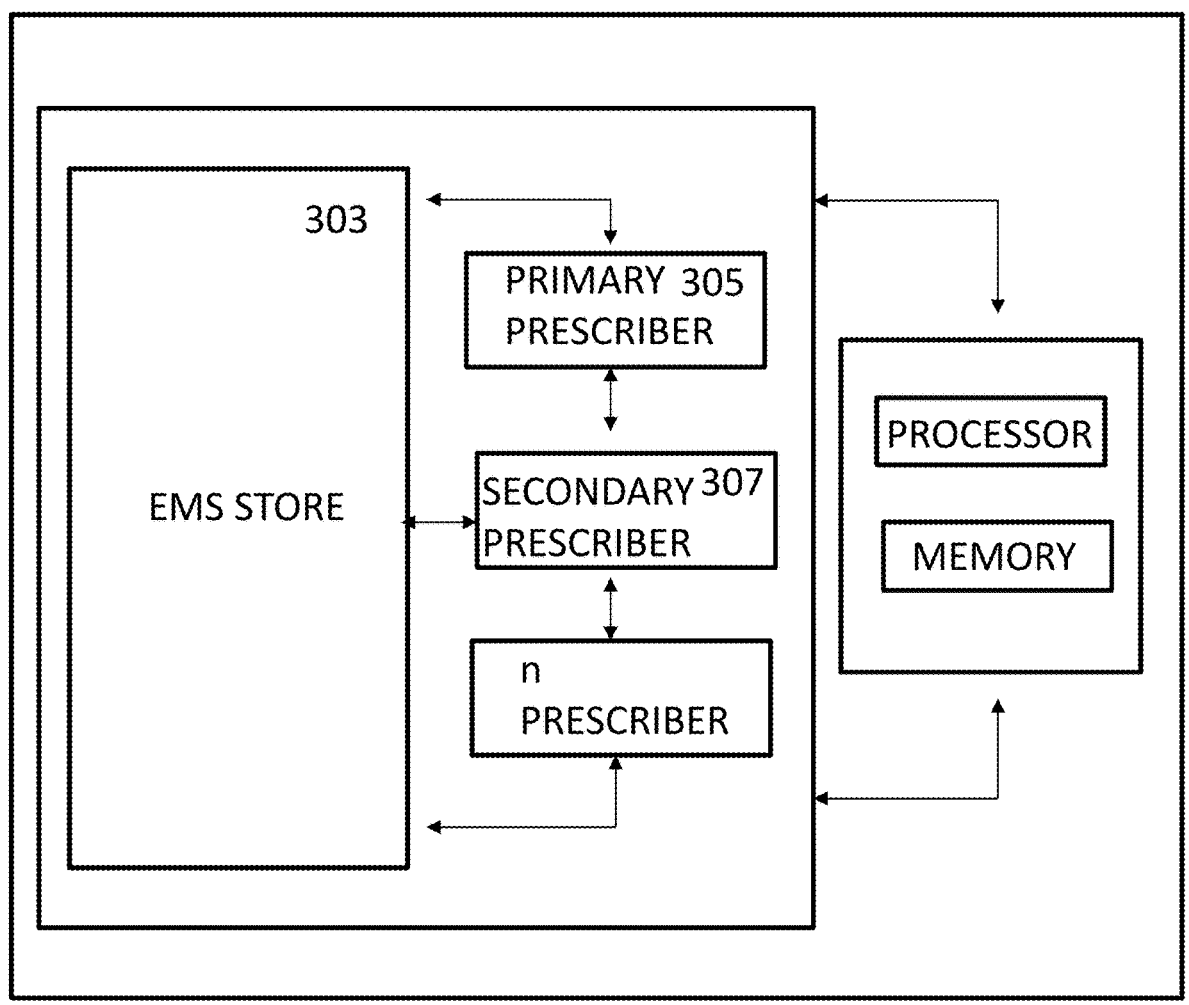
FIG. 10 illustrates a block diagram depicting the digital therapeutic system in accordance with an aspect of the invention.
Figure 11:
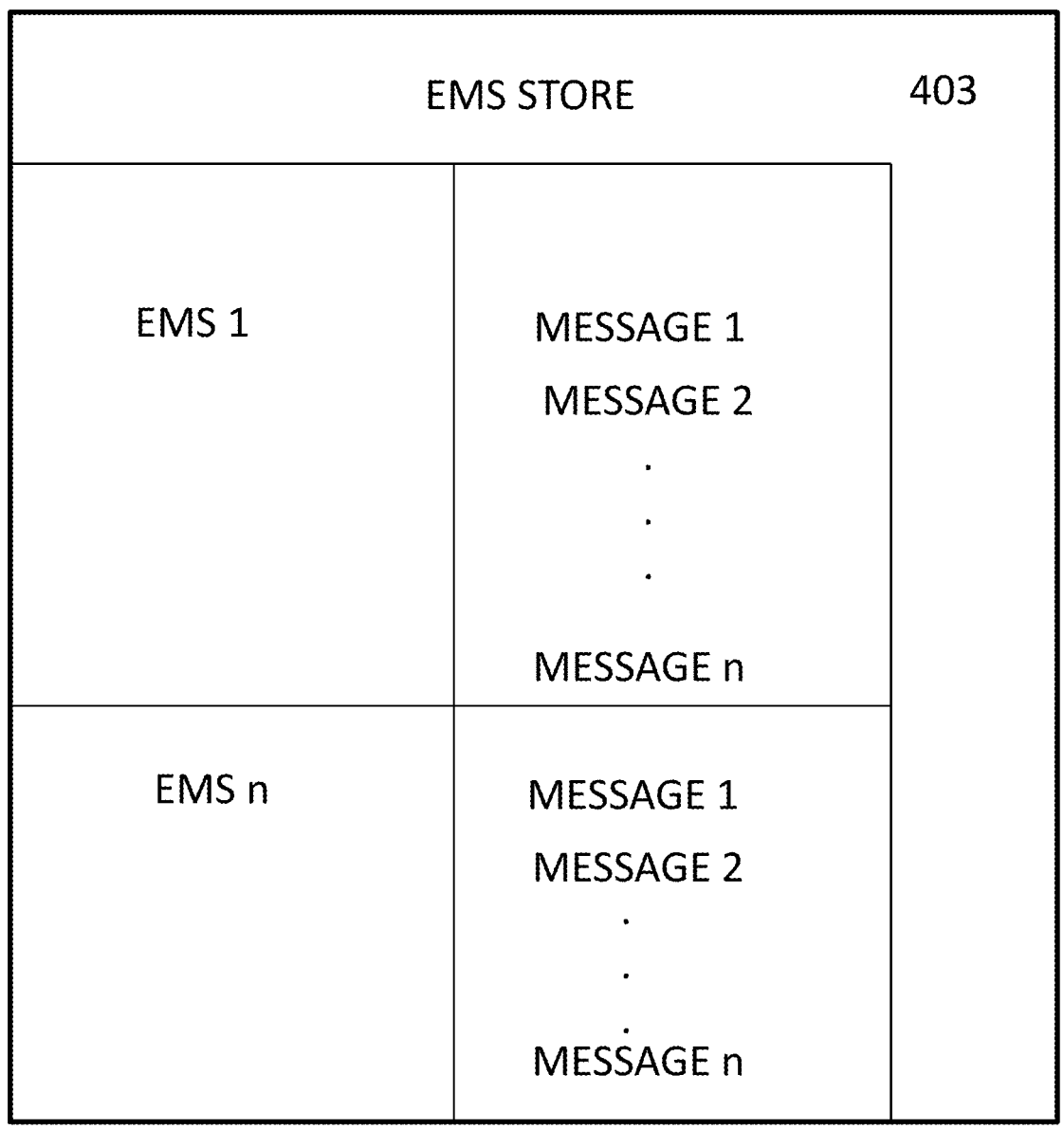
FIG. 11 illustrates a block diagram depicting the digital therapeutic system in accordance with an aspect of the invention.

Now in reference to FIGS. 10 and 11. FIGS. 10 and 11 both illustrate an exemplary embodiment of the digital therapeutic delivery system. FIGS. 10 and 11 illustrate an exemplary processing unit with at least a one prescriber 305, 307 configured for displaying interactively therapeutic content from an EMS store 303, 403 based on a user-specific EMS. As shown, the system may comprise an EMS store 303, 403; at least a primary message prescriber 305; a processor coupled to a memory element with instructions, the processor when executing said memory-stored instructions, configure the system to cause: at least one EMS from a plurality of EMS in the EMS store 303, 403 to be selected by the user.

As shown in FIG. 11, any number of EMS or EMS types may be included in the EMS store 303, 403. Each EMS may indicate at least one of a feeling, sensation, type of discomfort, mood, mental state, emotional condition, physical status of the user, and, or a behavioral intervention or training regimen. FIG. 11 also illustrates the fact that any number of messages or interactively therapeutic content may be associated with each EMS type. Each message; or interactively therapeutic content; or pushed therapeutic may contain at least one of a text, image, sound, video, art asset, suggested action or recommended behavior. The matching of message; interactively therapeutic content; or pushed therapeutic with EMS type may be pre-defined by at least one of an accredited expert or source; probabilistic; or deep learned. In a preferred embodiment, an accredited expert or source will require at least two independent sources of peer-reviewed scholarship or data in order to validate the match.

The at least primary message prescriber 305 may push a message or interactively therapeutic content personalized to the user based on at least one stored message matched to the selected EMS. For example, within the EMS store 403, if EMS 1 (lethargic) is selected as defined by the user or the system, any one of message 1, 2 . . . n may be selected by the prescriber 305. The pre-defined messages validated by the accredited expert may all be messages with documented utility in elevating mood and energy (rubric). The mood and energy documented for each message may be on a scale. For instance, EMS 1 message 1 may be low-moderate; EMS 1/message 2 may be moderate; and EMS 1/message n may be high-severe, etc. Any variant of the scale may be featured without departing from the scope of the invention. In other embodiments, the messages, while falling under the same rubric and un-scaled, can vary along design cues. For instance, the prescriber 305 may choose EMS 1/message 2, over other available messages, due to the fact that the message is comprised of traditionally feminine cues (pink-colored bauhaus typeface) for a female user. Other user profile or demographic information may further inform the prescribers 305 choice of message type, such as age, education level, voting preference, etc. User profile or demographic information may be user inputted or digitally crawled.

Still in reference to FIG. 11, the prescriber's 305 choice of message type is not specific to a user, user profile, or crawled user data. In a certain embodiment, the prescriber 305 may have to choose between any one of the message types (message 1, message 2 . . . message n) from the selected EMS type. This type of message assignment may be completely arbitrary. In other embodiments, the message assignment may be not specific to a user-generated or crawled profile but may be based on user history. In other words, a user's tracked level of engagement with a previous message or message from a previous session may inform message assignment by the prescriber 305. Tracking engagement of a user with a pushed or prescribed therapeutic message may be by camera-captured eye gazing, touch-screen interaction, time span between pushed therapeutic and user follow-up action, choice of follow-up action, etc.

In some embodiments, the full list of message types is not grouped by EMS type or along any design categories, but rather simply listed arbitrarily and mapped or matched to an appropriate EMS type. In this arbitrarily listed manner, the prescriber 305 may match to more than one EMS type. Likewise, a user may be defined by more than one EMS type and be prescribed the same message type.

Figure 12:
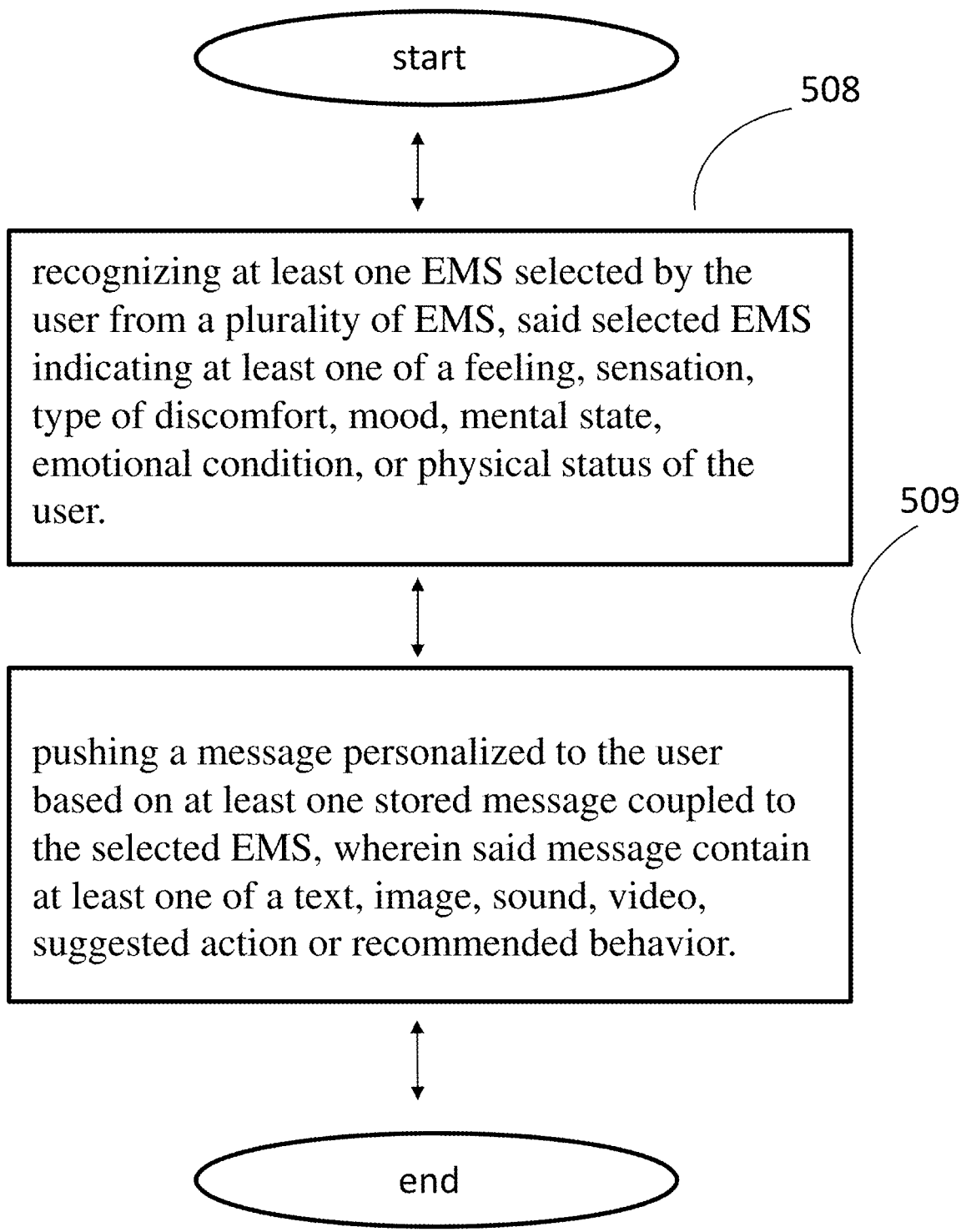
FIG. 12 illustrates a flow diagram depicting the digital therapeutic method in accordance with an aspect of the invention.

FIG. 12 illustrates a flow diagram depicting the method of delivering a digital therapeutic in accordance with an aspect of the invention. In a preferred embodiment, the method may comprise the steps of: (1) recognizing at least one EMS selected by the user from a plurality of EMS, the selected EMS indicating at least one of a feeling, sensation, type of discomfort, mood, mental state, emotional condition, or physical status of the user 508. Once the EMS is defined, the method then calls for (2) pushing at least a primary-level message personalized to the user based on at least one stored message coupled to the selected EMS 509.

In some embodiments, the system or method may call for pushing at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message. Much like the primary message or primary-level message, the secondary-level messages may also contain at least one of a text, image, sound, video, art asset, suggested action or recommended behavior. Again, the efficaciousness or therapeutic value of the primary or secondary messages are validated by at least one—and typically two—independent sources of clinical research or peer-reviewed science, as verified by a credentialed EMS expert.

In order to facilitate the at least secondary message or secondary-level message, the primary prescriber 305 may be used: Assigning a second message to the same user in the same session for the first defined EMS type. As is with the assignment of the first message, the assignment of the second may arbitrarily choose among EMS-grouped messages or from the full arbitrary list of messages in the EMS store. Moreover, the primary prescriber 305 may perform the secondary assignment in a logic-defined manner, wherein gathered, contextualized, or profiled data informs the assignment. In yet other aspects, second-level assignment may be performed by at least a secondary message prescriber 307, wherein the at least secondary message prescriber 307 pushes at least a secondary-level message personalized to the user based on a threshold-grade match of the user response to the pushed primary-level message with at least one stored response coupled to a stored primary-level message, whereby the user and stored response is a measure of at least one of a reaction, compliance, engagement, or interactivity with the pushed and, or stored primary-level message.

For instance, when a user-generated or system-generated EMS is defined as 'unfulfilled' for user A, a primary prescriber 305 assigns message 2 (uplifting; inspiring message) from EMS 1 (unfulfilled). In one embodiment, a secondary prescriber 307 prescribes a pro-social behavior, such as a local community service, immediately upon a touch interaction with the first inspiring message pushed. In other embodiments, a level of engagement, interaction or compliance may be tracked by the system to infer severity of the EMS. For instance, if user A does not comply with the touch-interaction requests from the first inspiring message or pro-social behavior recommendation of the second message, then the secondary prescriber 307 may push a less physically strenuous pro-social recommendation, such as suggesting to call an in-network licensed expert or simply make a cash donation to a charitable organization of the users choosing via a linked micro-payment method. For the purposes of inferring severity of EMS, any number of diagnostics that leverage any one of the on-device tools may be used, such as gyroscopic sensors or cameras. Secondary assignment may also be based on learned history, such as a past positive reaction (compliance) to a receiving a message from a loved one that a donation was made in user A's name to a charitable organization. Based on such history, a secondary prescriber 307 may assign a primary or secondary message recommending to make a donation in the name of a loved one during an 'unfulfilled' EMS experienced by user A.

The processing unit may further be communicatively coupled to at least one of an interface module, display module, input module, logic module, a context module, timeline module, tracking module, notification module, and a payment/gifting module. In accordance with one aspect, the notification module may be configured to generate reports at regular intervals (such as daily at 12:00 PM, weekly and monthly), on-demand (when the user requests for a report corresponding to the user), when triggered by an event, or upon a detected severe EMS. In an embodiment of the present invention, the notification module may also be configured to send a notification to the user or to a chosen loved one of the user. The notification may be a message, a phone call or any other communication means.

In an embodiment of the present invention, a timeline module may push already pushed messages in at least one of a static, dynamic, and, or scheduled fashion based on at least one of the user's scheduler criteria. The line of static, dynamic, and, or scheduled messages may be curated by the user, pre-set, or dynamically pushed based on any one of a user parameter. In some embodiments, the timeline module enables the displayed line of static, dynamic, and, or scheduled messages to be further replicated on at least one of a social media timelines or stories. In other words, the timeline module enables the displayed messages to be further shared with social media outlets.

In an embodiment of the present invention, a payment or gifting module may enable purchasing and gifting donations, physical objects, or digital assets. The gifting module may further be coupled to a distributive digital ledger, wherein each transaction among any user is represented as a unique node in the digital ledger. Each node tagged with meta data facilitating at least one of a transaction, validation and, or registration for each transaction.

Figure 13:
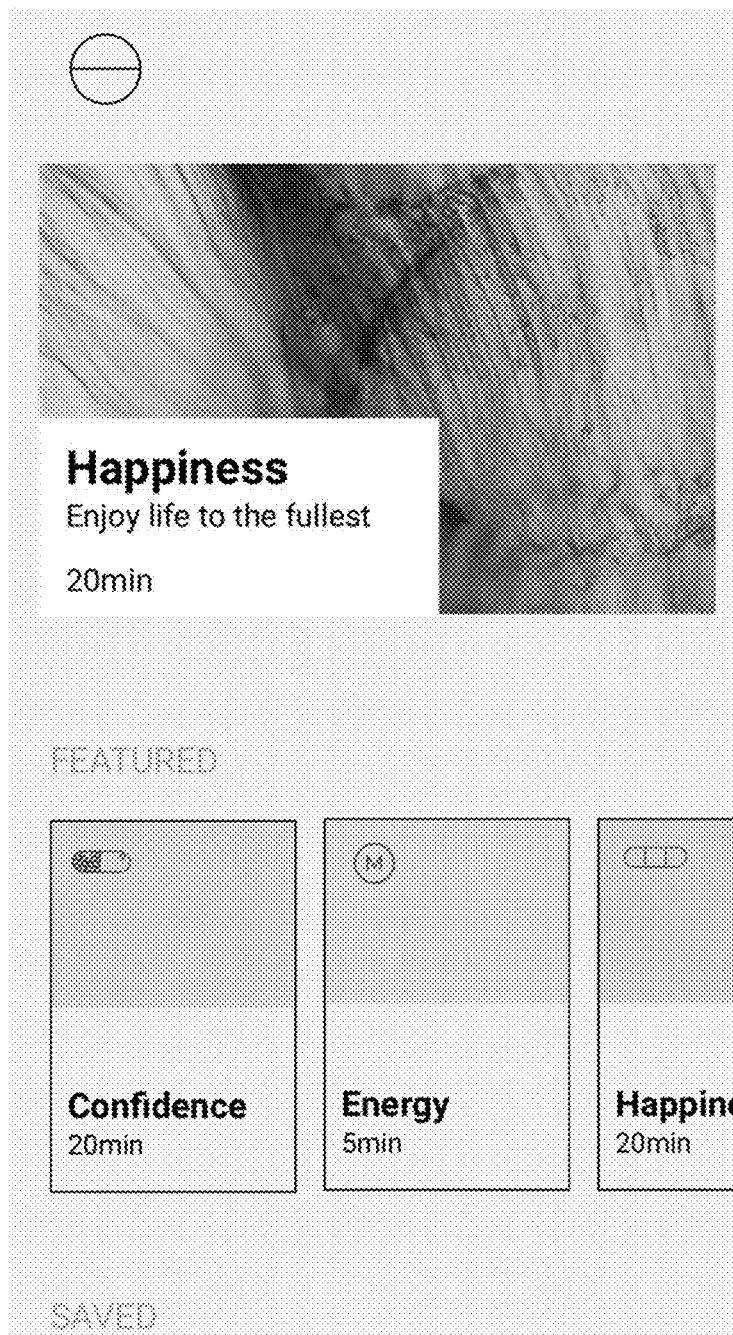
FIG. 13 illustrates a representative screen shot depicting an exemplary user interface in accordance with an aspect of the invention.

FIG. 13 is a representative screen shot depicting an exemplary user interface in accordance with an aspect of the invention. As shown, the top layer 602 depicts a spotlighted EMS and the bottom layer is a scroll menu of EMS. In this case, the concept of EMS, as earlier defined, also includes behavioral interventions or training regimens, in addition to an emotional and mental state. In some embodiments, an exemplary user experience may have both top layer 602 and bottom layer 604 within the same screen, wherein the top layer 602 is a spotlighted rendering of the focused EMS from the EMS menu depicted in the bottom layer 604. In other embodiments, the window may only feature the scrolling EMS menu as depicted in the bottom layer 604, wherein the focused EMS from the plurality of EMS may pop-out, or be emphasized anyhow. In yet other embodiments, the window may only feature the one EMS at a time, allowing for the user to go through the entire menu, one window (EMS) at a time. In yet other embodiments, the menu may be featured in a thumbnail format, allowing the user to choose at least one EMS from a thumbnail menu, sized to fit in a single window, or alternatively, configured for scrolling.

Figure 14:
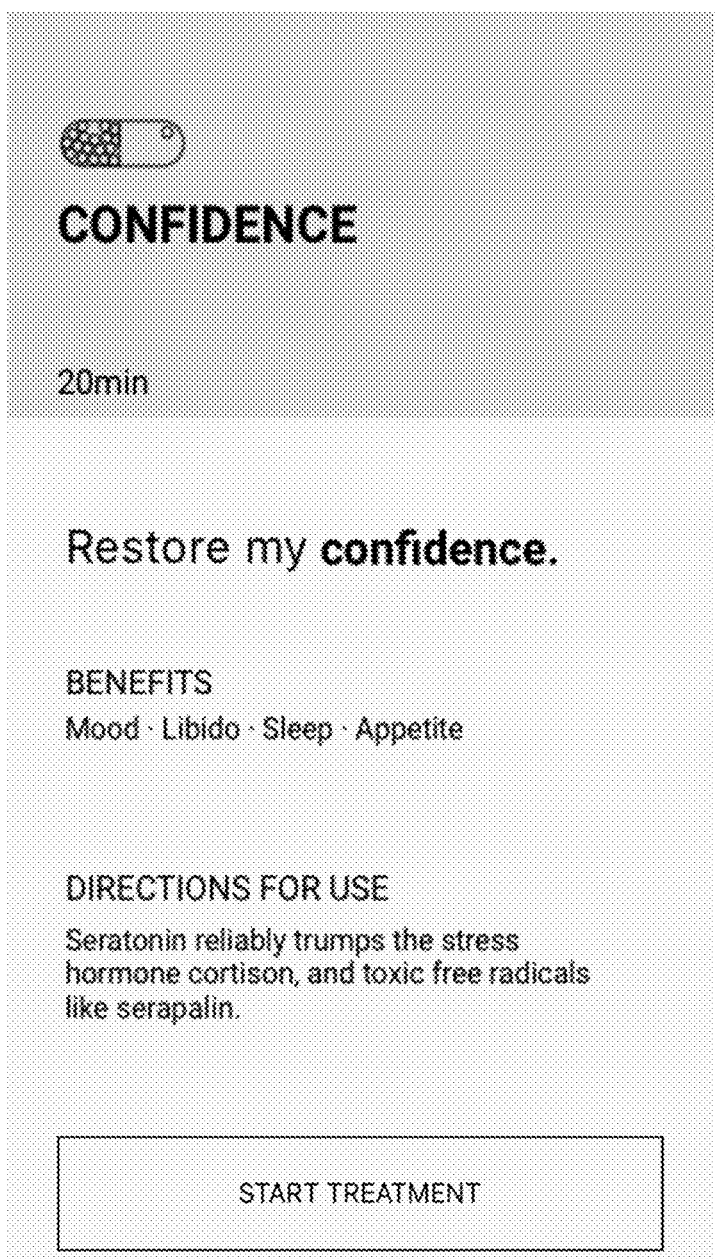
FIG. 14 illustrates a representative screen shot depicting an exemplary user interface in accordance with an aspect of the invention.

FIG. 14 is a representative screen shot depicting an exemplary user interface in accordance with an aspect of the invention. Once the EMS (behavioral intervention or training regimen) is defined, users can read more about the intervention or training regimen they're going to start and self-administer (have pushed to their device) from a top portion of the card (window) 702. On the same card (window), the bottom portion may highlight proven benefits, and then provide directions for use, mixing real guidance with elements of humor 704. The medical-inspired alliteration and iconography are intended to invoke a sense of prescriptive health care or wellness.

Figure 15:
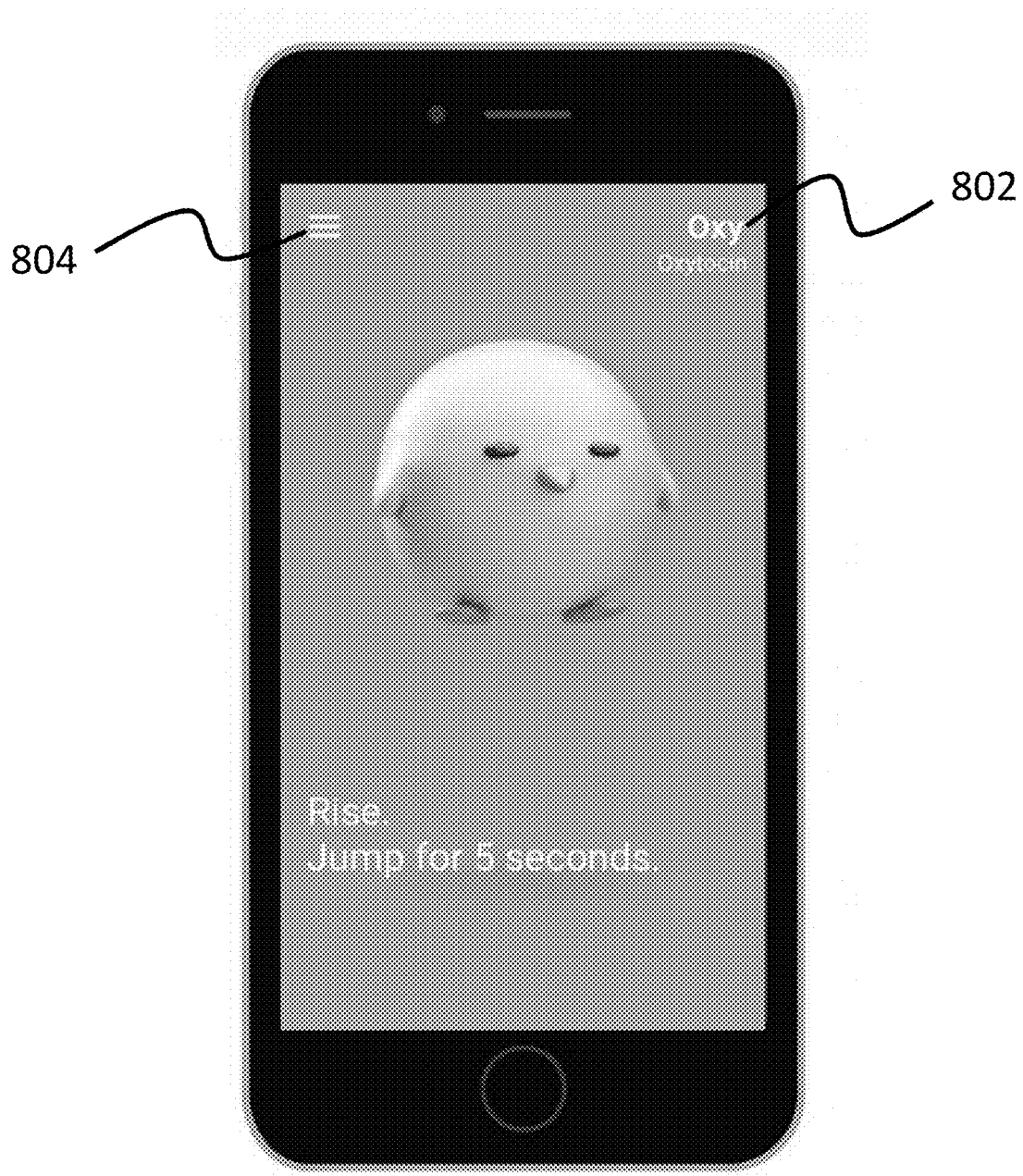
FIG. 15 illustrates a representative screen shot depicting an exemplary user interface in accordance with an aspect of the invention.
Figure 16:
FIG. 16 illustrates a representative screen shot depicting an exemplary user interface in accordance with an aspect of the invention.

FIGS. 15 and 16 are a representative screen shot depicting an exemplary user interface in accordance with an aspect of the invention. As shown on FIG. 15, once the EMS (regimen) is defined and a particular course of treatment (message) is started, on the top-right portion of the next card explicitly identifies the specific drug benefit 802. While not shown, by tapping the drug abbreviation, users can see the source of supporting scientific research 802. By tapping the hamburger icon, users can choose to save the individual card, or share the card and its contents with friends across social media. It is to be understood by a person of ordinary skill in the art that these icons, or any icons, on this card (window), or any card (window), may be positioned elsewhere (or anywhere), without departing from the inventive scope.

As shown on FIGS. 15 and 16, the focal point of the card (window) is the actual EMS-defined message (treatment), and in the case of this window, is a suggested action—jump for 5 seconds. FIG. 15 represents an exemplary card formatted for a mobile phone, while FIG. 16 represents an exemplary card formatted for a smart watch. Jumping for 5 seconds is a suggested action to restore the oxytocin neurotransmitter, which is documented for building happiness and confidence—the initially chosen EMS or behavioral intervention by the user (FIG. 13). The veracity of the message or suggested action is supported by the referenced peer-reviewed research and co-signed credentialed expert 802. As a person, skilled in the art will recognize from the previous detailed description and from the figures and claims, modifications and changes can be made to the embodiments of the cards, windows, icons, design elements, EMS types, behavioral intervention types, message types, without departing from the scope of this invention as defined in the following claims.

While not shown in FIGS. 15 and 16, the messages (cards/windows) may comprise a single or battery of physical and, or cognitive tasks and based on responses, further indicate a more nuanced EMS for a more tailored initial or subsequent message. Responses may include a level of compliance, engagement, interaction, choices, etc. Furthermore, for deeper and more nuanced EMS definition, assigning an indication score or color-coded range to further convey EMS severity may be achievable. As a result, matching of message type to scored or color-coded EMS may produce a more refined match for pushing of even more personalized digital content or therapeutics.

Figure 17:
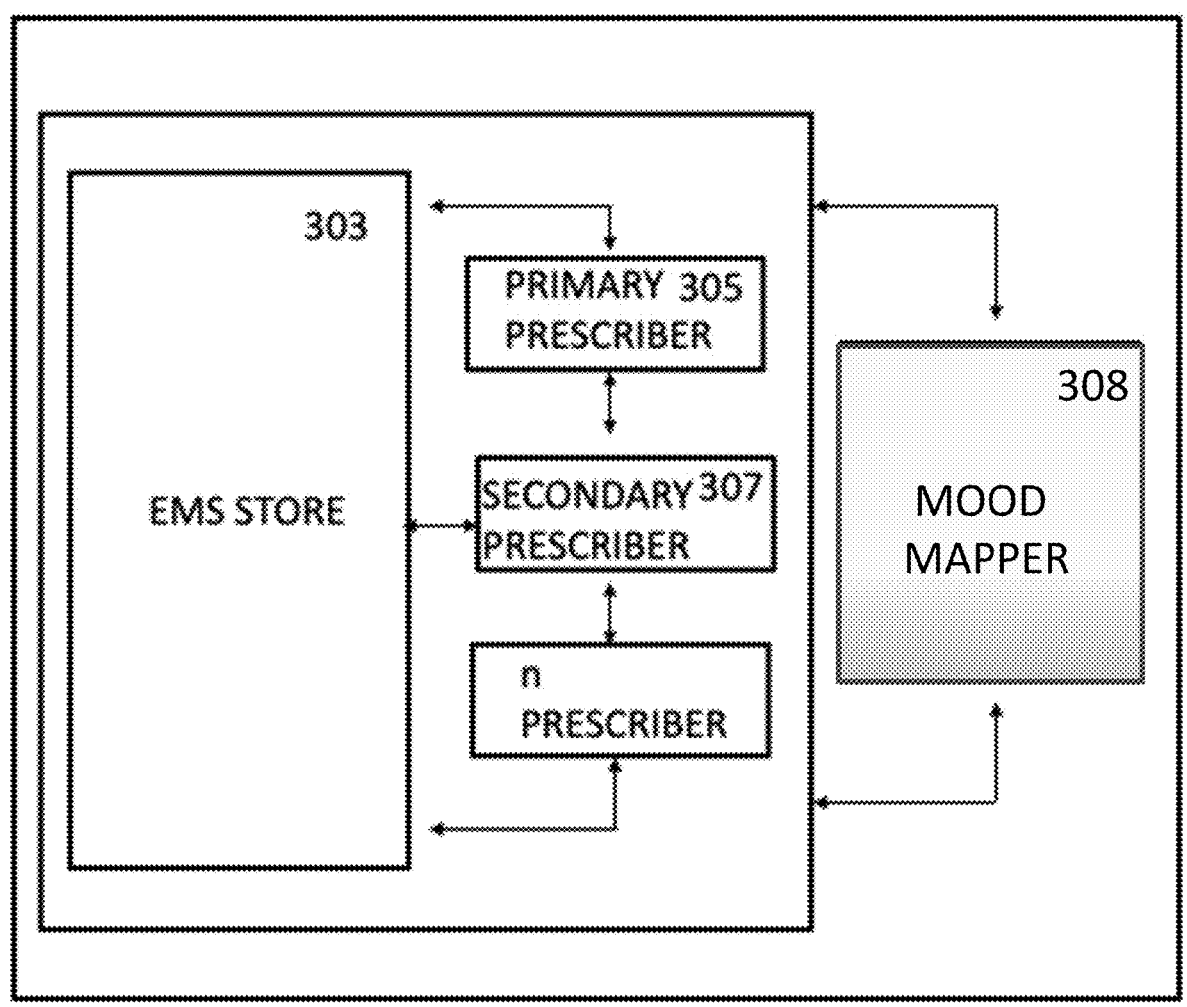
FIG. 17 illustrates a block diagram representing a system including the mood mapper module in relation to the EMS store and prescribers in accordance with an aspect of the invention.
Figure 18:
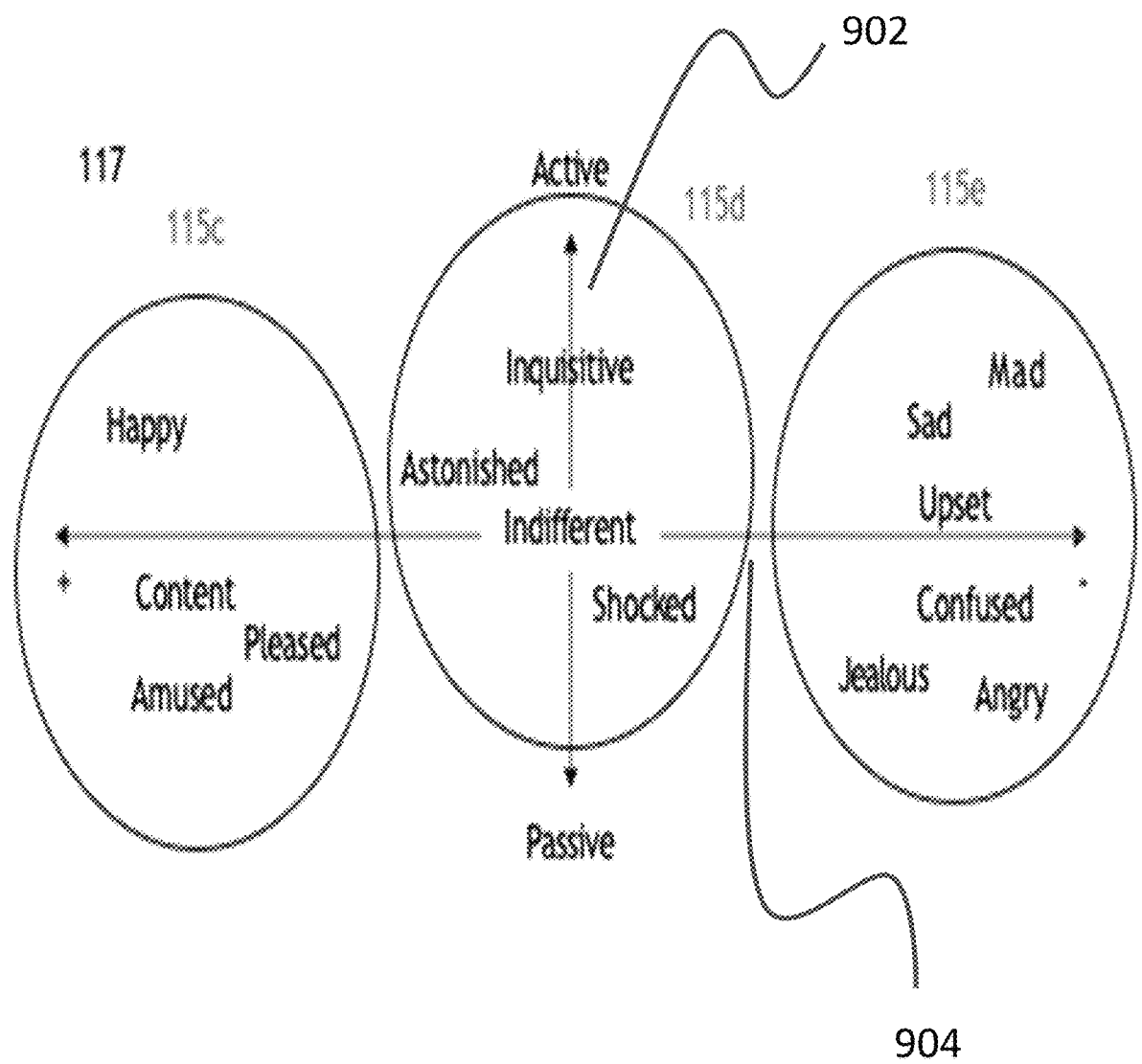
FIG. 18 illustrates a graphical representation of the mood map including the at least two correlates of behavior underlying the user-plotted assessment of behavior in accordance with an aspect of the invention.

FIG. 17 illustrates a block diagram representing a system including the mood mapper module 308 in relation to the EMS store and prescribers in accordance with an aspect of the invention. In combination, the system enables a specific sub-routine that ultimately provisions a dynamic assessment of a user's EMS (dEMS) based on a multi-correlate coordinate system (mood map). FIG. 18 illustrates a graphical representation of the mood map including the at least two correlates of behavior (active/passive 902; positive/negative 904) underlying the user-plotted assessment of behavior in accordance with an aspect of the invention. The mood map allows users to plot as a single point along at least two correlates of behavior—resulting in a push of hyper-personalized digital content with therapeutic value to reinforce or counter the user-mapped dynamic assessment.

In a preferred embodiment, as demonstrated in FIG. 17/18, the system featuring a user-plotted mood map for deriving a dEMS for a hyper-personalized digital therapeutic comprises a message prescriber 305, 307; an EMS store 303; a processor coupled to a memory element stored with instructions, said processor when executing said memory-stored instructions, configure a mood mapping module (mood mapper) 308 to cause display of a coordinate-based sentiment value spectrum (mood map) comprising one positive to negative-scaled axis 904 and one perpendicular active to passive scaled axis 902 forming a two-dimensional plot of a sentiment value along a positive to negative line (positivity correlate) and an active to passive line (activity correlate); at least one user-plotted point on the displayed mood map to reflect a two-dimensional EMS (dynamic EMS) along the two correlates of positivity and activity, said dynamic EMS indicating a granular assessment of at least one of a feeling, sensation, mood, mental state, emotional condition, or physical status of the user; and the message prescriber 305, 307 delivering at least a primary-level message (digital therapeutic) personalized to the user based on at least one of a stored message coupled to the dynamic EMS (hyper-personalized digital therapeutic).

In alternative embodiments, the mood map may comprise at least three axis in a three-dimensional representation, wherein one axis represents the positivity correlate; the second axis the activity correlate; and the third axis a time or duration correlate. In yet other embodiments, any type of correlates of behavior along any number of axis may be represented to capture a dEMS based on a user-plot on the mood map.

FIG. 17 illustrates an exemplary processing unit with at least a one prescriber 305 configured for displaying interactively therapeutic content from an EMS store 303 based on a user-plotted dEMS (hyper-personalized digital therapeutics). As shown, the system may comprise an EMS store 303; at least a primary message prescriber 305; a processor coupled to a memory element with instructions, the processor when executing said memory-stored instructions, configure the system to cause: at least one EMS from a plurality of EMS in the EMS store 303 to be pushed based on the user-plotted point, and alternatively, the dynamic sentiment value represented by the user-plotted point based on the intersecting correlates of behavior.

While not shown in FIG. 17, any number of EMS or EMS types may be included in the EMS store 303. Each EMS may indicate at least one of a feeling, sensation, type of discomfort, mood, mental state, emotional condition, physical status of the user, and, or a behavioral intervention or training regimen. Any number of messages or interactively therapeutic content may be associated with each EMS type. Each message; or interactively therapeutic content; or pushed therapeutic may contain at least one of a text, image, sound, video, art asset, suggested action or recommended behavior. The matching of message; interactively therapeutic content; or pushed therapeutic with EMS type may be pre-defined by at least one of an accredited expert or source; probabilistic; or deep learned. In a preferred embodiment, an accredited expert or source will require at least two independent sources of peer-reviewed scholarship or data in order to validate the match.

The at least primary message prescriber 305 may push a message or interactively therapeutic content hyper-personalized to the user based on at least one stored message matched to the selected EMS. For example, within the EMS store 303, if EMS 1 (amused) is selected as plotted in the far bottom left corner (FIG. 18, 115c) the by the user, any one of message 1, 2 . . . n may be selected by the prescriber 305. The pre-defined messages validated by the accredited expert may all be messages with documented utility in elevating mood and energy (counter-effect) or playful, light-hearted (reinforcing). The effects documented for each message may be on a scale. For instance, EMS 1 message 1 may be low-moderate; EMS 1/message 2 may be moderate; and EMS 1/message n may be high-severe, etc. EMS types or message types may be color coded or scored to indicate severity. Any variant of the scale may be featured without departing from the scope of the invention. In other embodiments, the messages, while falling under the same rubric and un-scaled, can vary along design cues. For instance, the prescriber 305 may choose EMS 1/message 2, over other available messages, due to the fact that the message is comprised of traditionally feminine cues (pink-colored bauhaus typeface) for a female user. Other user profile, demographic information, or contextual information may further inform the prescribers 305 choice of message type, such as age, education level, voting preference, etc. User profile or demographic information may be user inputted, digitally crawled, sensed or captured.

Still in reference to FIG. 17, the prescriber's 305 choice of message type may not specific to a user, user profile, or crawled user data. In a certain embodiment, the prescriber 305 may have to choose between any one of the message types (message 1, message 2 . . . message n) from the selected EMS type. This type of message assignment may be completely arbitrary. In other embodiments, the message assignment may be not specific to a user-generated or crawled profile but may be based on user history. In other words, a user's tracked level of engagement with a previous message or message from a previous session may inform message assignment by the prescriber 305. Tracking engagement of a user with a pushed or prescribed therapeutic message may be by camera-captured eye gazing, touch-screen interaction, time span between pushed therapeutic and user follow-up action, choice of follow-up action, etc.

In some embodiments, the full list of message types is not grouped by EMS type or along any design categories, but rather simply listed arbitrarily and mapped or matched to an appropriate EMS type. In this arbitrarily listed manner, the prescriber 305 may match to more than one EMS type. Likewise, a user may be defined by more than one EMS type and be prescribed the same message type. For instance, as illustrated in FIG. 18, a plot may indicate for an intermediary EMS between astonished and indifferent 115d or between sad and mad 115e. In such an example, two EMS types may be diagnosed/assigned. Message types may be prescribed suited for the intermediary EMS diagnosis. For example, in the case of the intermediary astonished/indifferent, the plot point may indicate that the user is stronger leaning towards astonished than indifferent, and as a result, exclude certain message types associated with the traditional indifferent EMS type. In other embodiments, the mood mapper module 308 can take the coordinate position of each plot, calculate a precise position, and plot the positon on the dynamic sentiment value spectrum, wherein every coordinate position correlates with a precise EMS. Precise EMS types may be on a scale or depicted with certain leanings/dispositions toward a specific correlate or other EMS types.

Figure 19A:
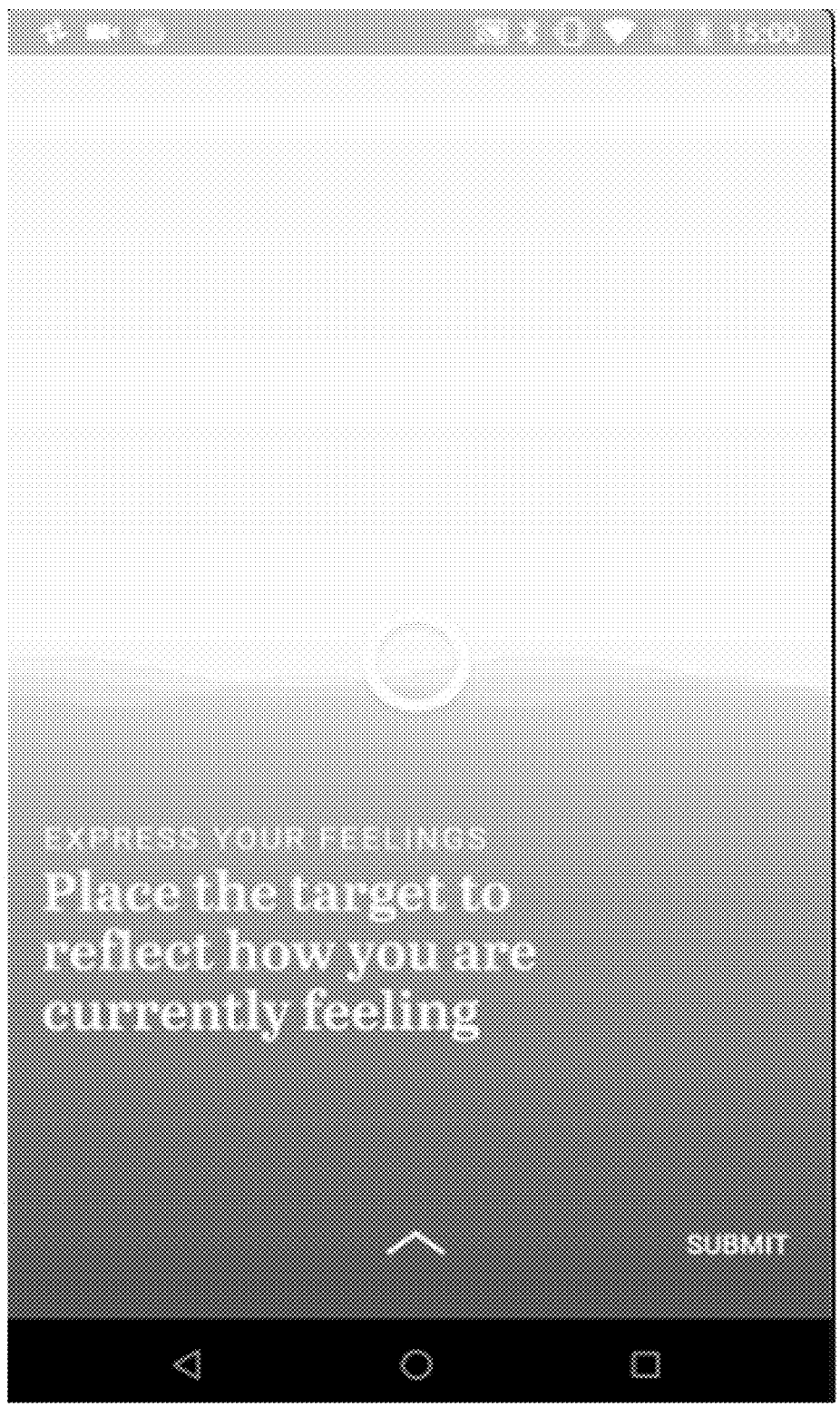
FIG. 19A, FIG. 19B, FIG. 19C, and FIG. 19D are exemplary screen shots of the mood map interface in accordance with an aspect of the invention.
Figure 19B:
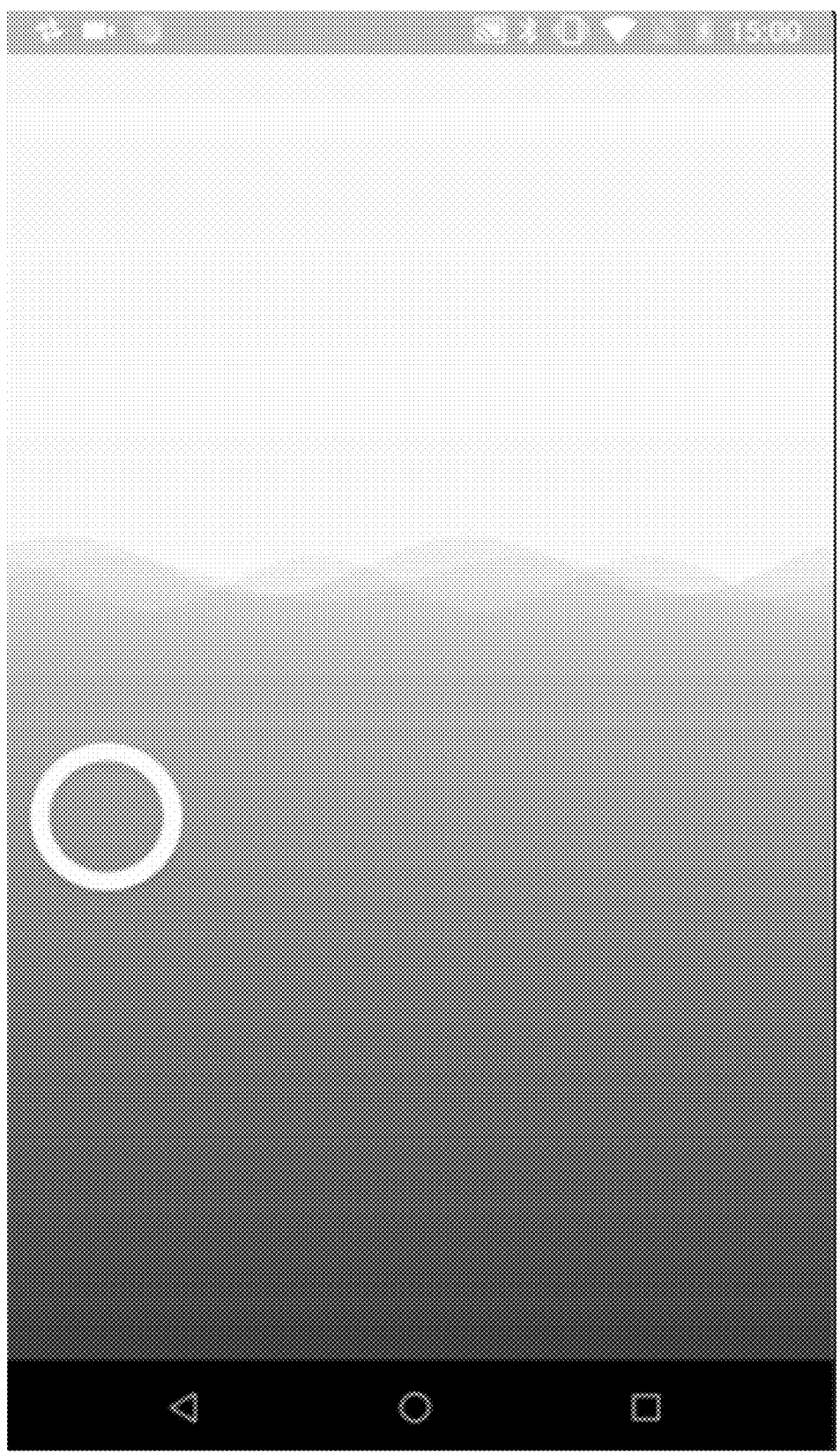
Figure 19C:
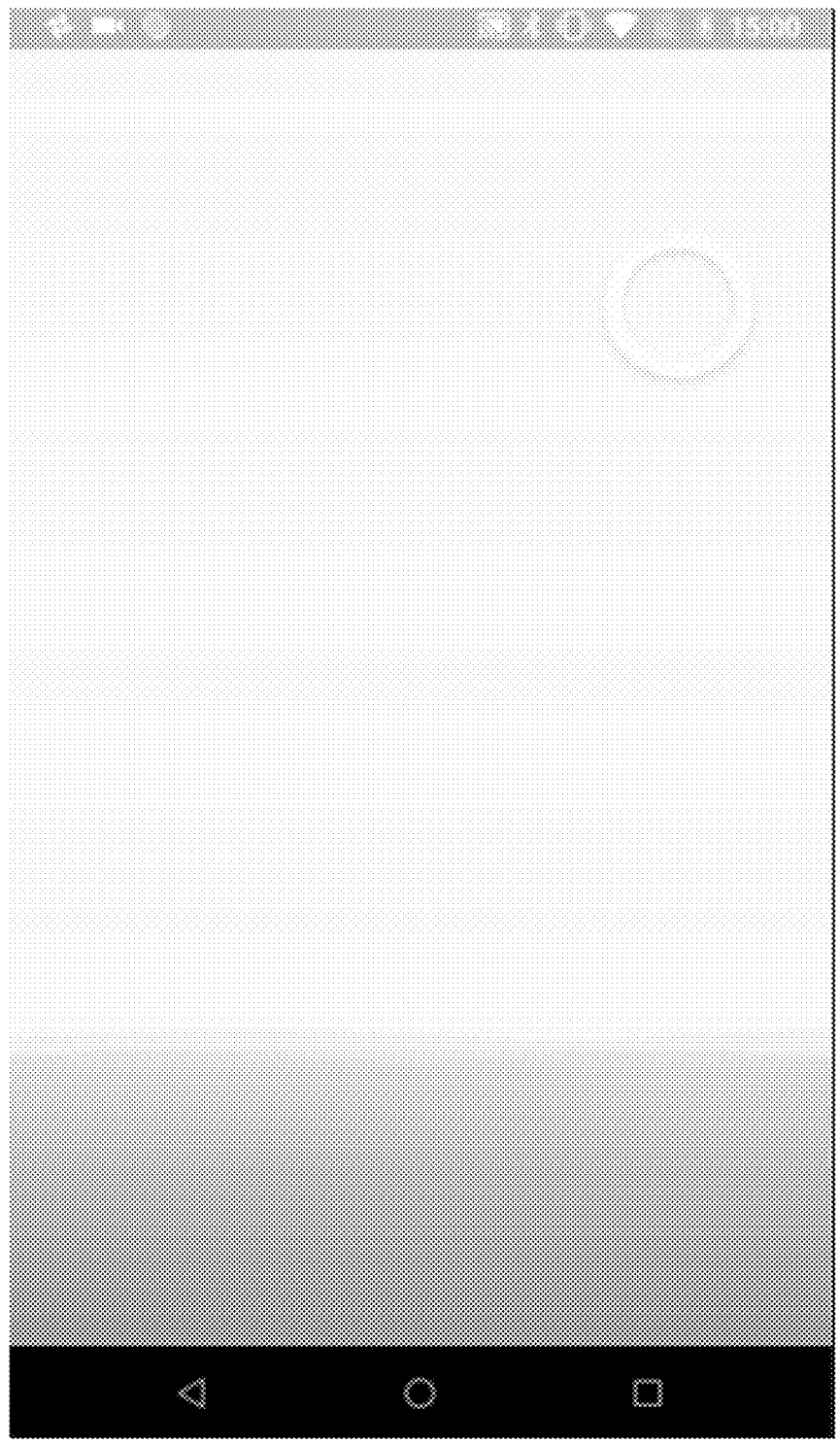
Figure 19D:
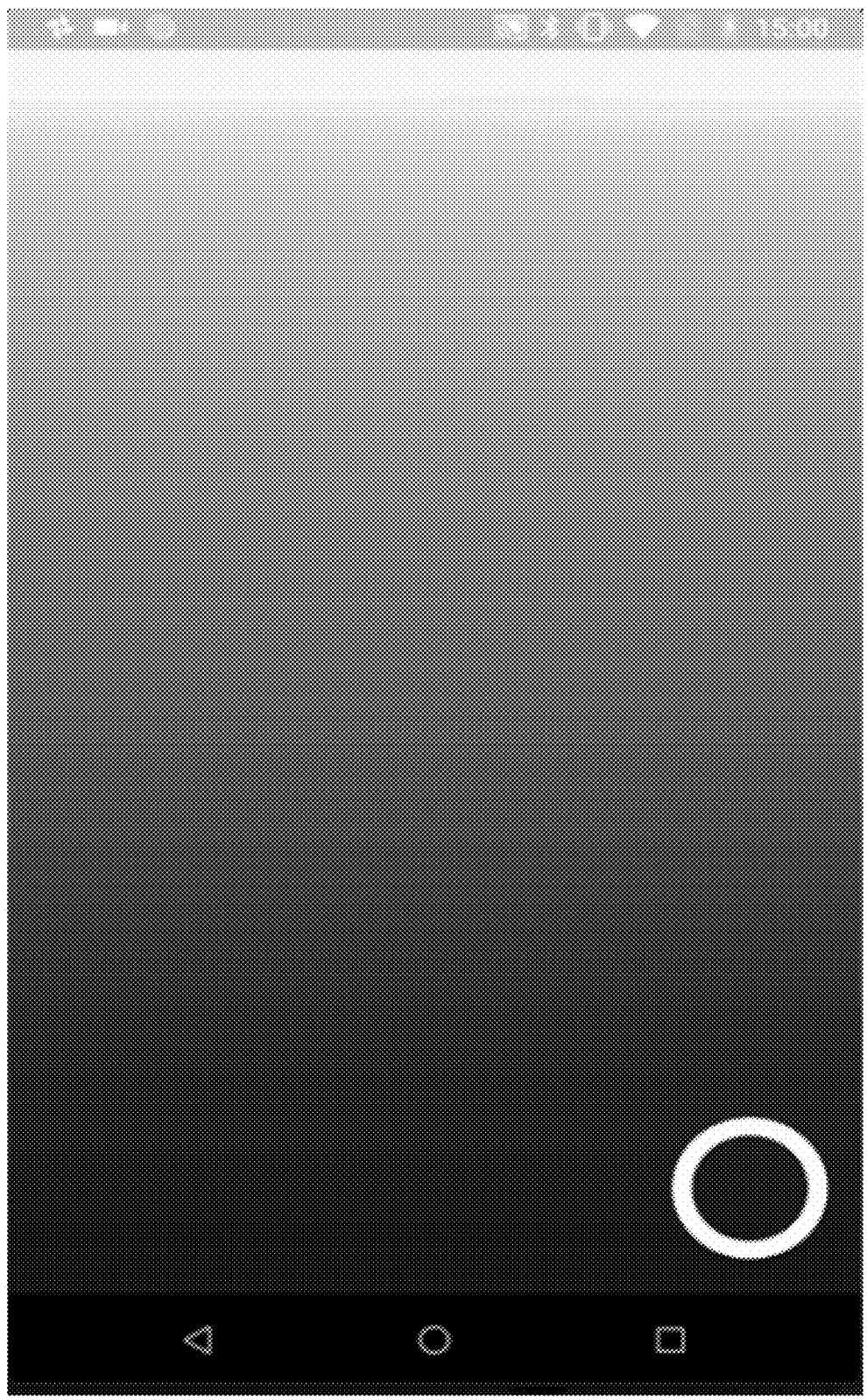

FIGS. 19A-19D are exemplary screen shots of the mood map interface in accordance with an aspect of the invention. In FIG. 19A, the mood maps x-axis is an activity correlate represented as an ocean surface horizontally bisecting the display, whereby a wave action increases the further right or left from a center point and the wave action calms further left or right from the center point. The mood maps y-axis is a positivity correlate represented as a sky above the ocean surface and ocean depth below the ocean surface, whereby the sky light becomes brighter (indicating positivity) the further up from the center point and the ocean depth becomes dimmer (indicating negativity) the further down from the center point (FIGS. 19B, 19C, 19D).

While not illustrated, in some embodiments, the mood maps z-axis is a time or duration correlate, wherein the mood map shifts ninety degrees to reveal a side-sectional view of the ocean surface and shore, whereby the shore at either end of the display represents day zero and time or duration increases the further from the shore. Other correlates of behavior may be represented on any one of the two or three axis of the mood map, without departing from the scope of the invention.

The mood map/mapper may allow for a user to plot a single point on the x/y or x/y/z map, wherein each axis represents a unique and complementary behavioral attribute. In other embodiments, the user may plot multiple points on the x/y or x/y/z map to provide at least four behavioral attributes to inform a dEMS assessment by creating a coefficient, which may be eventually converted into at least one of a dEMS score, dEMS behavioral characteristic, d/EMS type, neurotransmitter implicated, treatment regimen, digital therapeutic type, etc. In other embodiments, at least one of a dEMS score, dEMS behavioral characteristic, d/EMS type, neurotransmitter implicated, treatment regimen, or digital therapeutic type may be derived without the need of a coefficient or algorithmically, statistically, probabilistically, or deep learned.

In yet other embodiments, the user may engage the mood map/mood mapper by finger-tip scrolling across the map and removing the finger to pinpoint the exact location of the circle/cursor point to define the at least two-axis correlates of behavior. In other embodiments, the user may finger-tip scroll across the map and double-tap to pinpoint the exact location of the circle/cursor point.

While not illustrated, in some embodiments, the mood map/mood mapper may be configured in alternate ways to interactively engage the user in defining the user's dEMS. For instance, in one embodiment, the map/mapper may be an interface comprising a series of vertically oriented scales requiring the user to slide a bar up or down the scale in response to a question designed to infer wholly or partially a dEMS of the user. For instance, "what is the likelihood of the polar ice caps completely melting by 2050?" The user would be prompted to slide the bar in response to the question, wherein the furthest top of the scale represents an extremely high likelihood and the furthest bottom of the scale represents an extremely low likelihood. Questions may extend to questions of a more personal nature, such as, "do you believe you will lose your patience, exhibited by an outburst of some kind, during the course of the work day today?" The system may capture the responses to each of the questions and create a coefficient, which may be eventually converted into at least one of a dEMS score, dEMS behavioral characteristic, d/EMS type, neurotransmitter implicated, treatment regimen, digital therapeutic type, etc. In other embodiments, at least one of a dEMS score, dEMS behavioral characteristic, d/EMS type, neurotransmitter implicated, treatment regimen, or digital therapeutic type may be derived without the need of a coefficient or algorithmically, statistically, probabilistically, or deep learned.

Figure 20A:
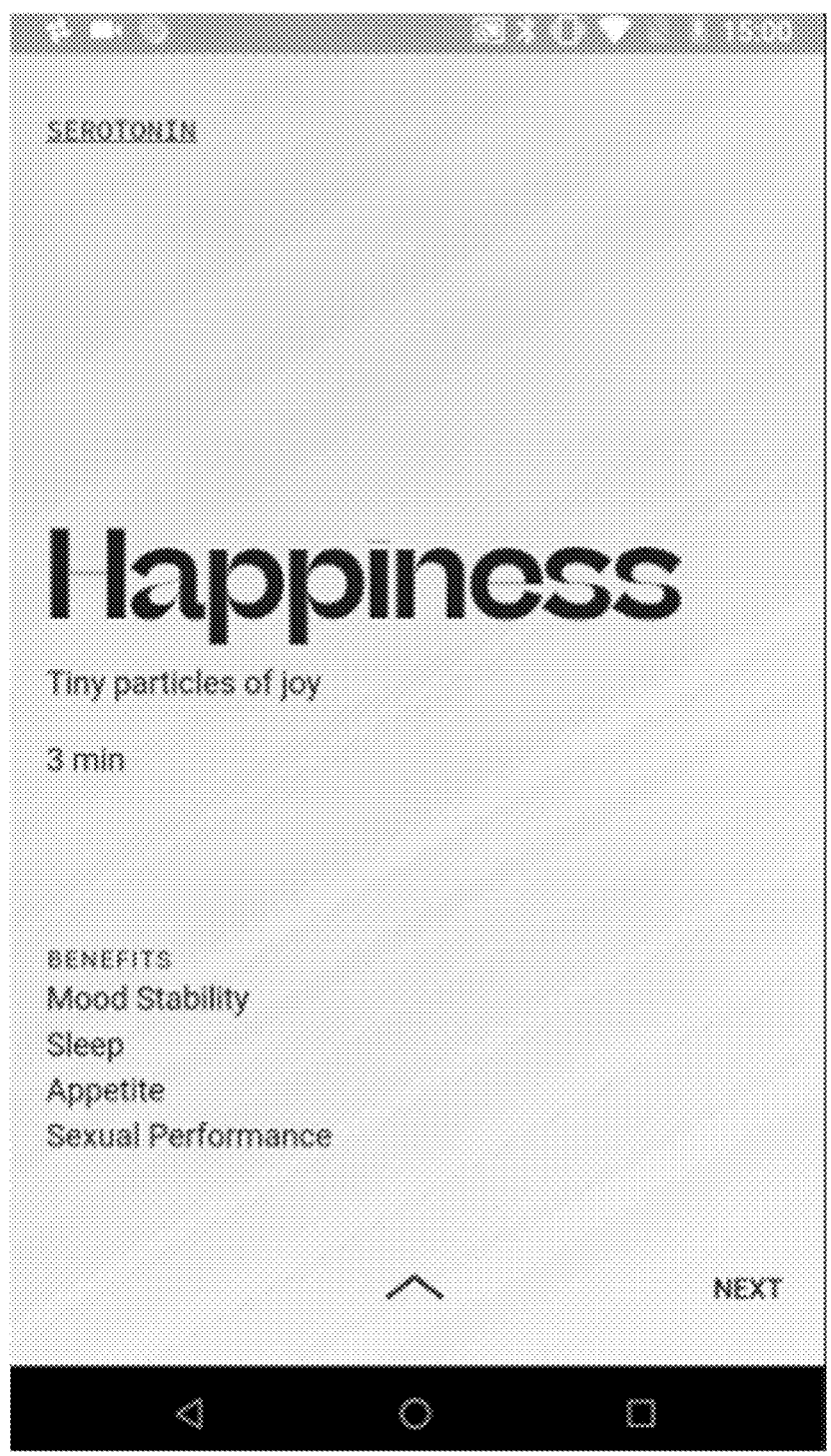
FIG. 20A and FIG. 20B are exemplary screen shots of the hyper-personalized digital therapeutic pushed to the user-plotted dynamic EMS.
Figure 20B:
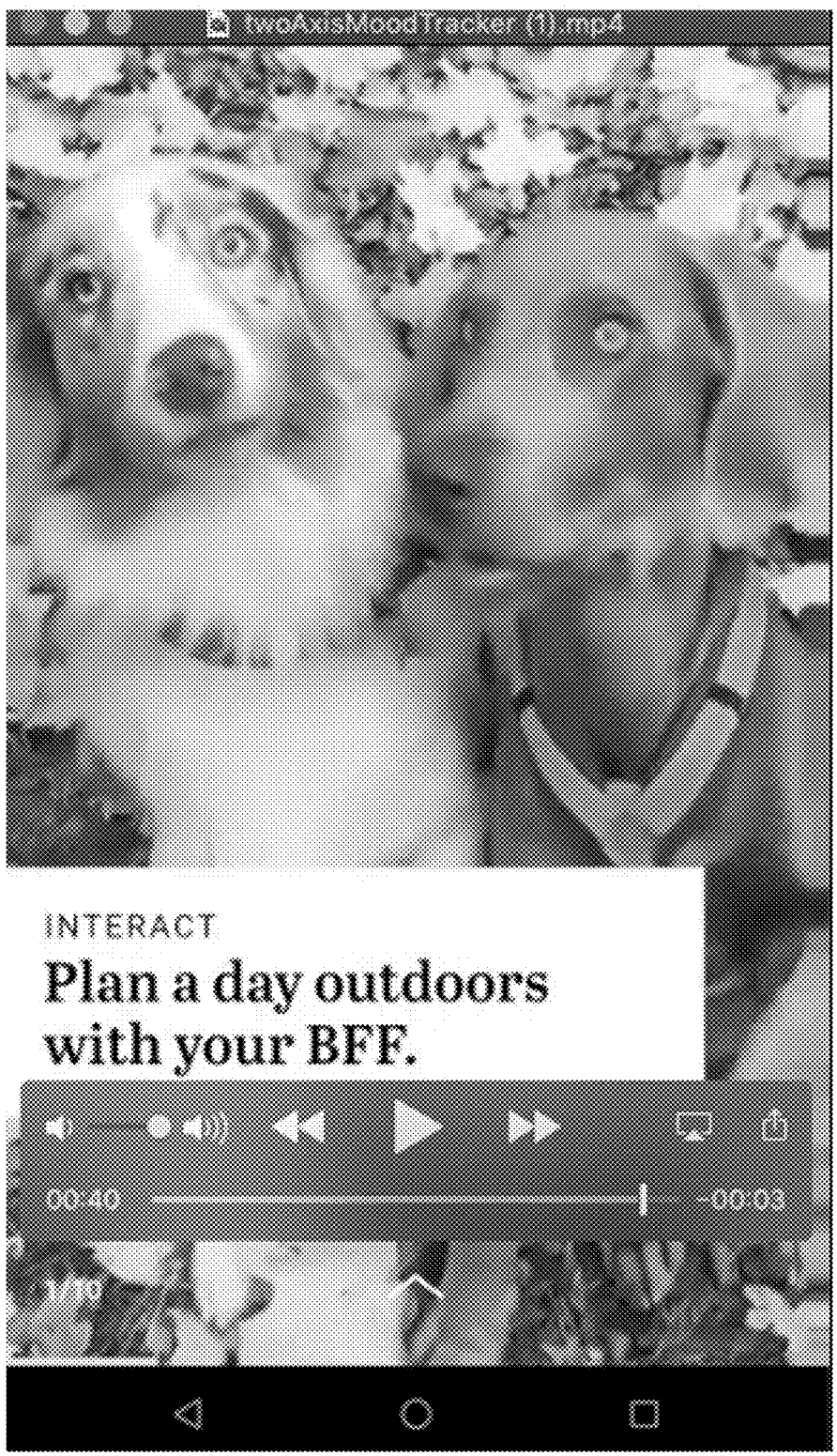

FIG. 20A and FIG. 20B are exemplary screen shots of the hyper-personalized digital therapeutic pushed to the user-plotted dEMS. Once the EMS (regimen) is defined and a particular course of treatment (message) is started, the first card (window) explicitly identifies the specific EMS and its associated neurotransmitter/effects. While not shown, by tapping the specific EMS and its associated neurotransmitter/effects, users can see the source of supporting scientific research. By tapping the hamburger icon, users can choose to save the individual card, or share the card and its contents with friends across social media. It is to be understood by a person of ordinary skill in the art that these icons, or any icons, on this card (window), or any card (window), may be positioned elsewhere (or anywhere), without departing from the inventive scope.

The focal point of the same or next card (window) in series is the actual EMS-defined message (treatment), and in the case of this window, a suggested action—to plan a day outdoors with a friend. This suggested action is to restore/maintain/improve on the dynamic EMS of happiness by expanding on the associated serotonin neurotransmitter, which is documented for building happiness and confidence. The veracity of the message or suggested action is supported by the referenced peer-reviewed research and co-signed credentialed expert. As a person skilled in the art will recognize that modifications and changes can be made to the embodiments of the cards, windows, icons, design elements, EMS types, behavioral intervention types, message types, without departing from the scope of this invention.

While not shown in FIGS. 20A and 20B, the messages (cards/windows) may comprise a single or battery of physical and, or cognitive tasks and based on responses, further indicate a more nuanced EMS for a more tailored initial or subsequent (secondary) message. Responses may include a level of compliance, engagement, interaction, choices, etc. Secondary messages may be pushed from secondary prescribers or primary prescribers coupled to the EMS store. Furthermore, for deeper and more nuanced EMS definition, assigning an indication score or color-coded range to further convey EMS severity may be achievable. As a result, matching of message type to scored or color-coded EMS may produce a more refined match for pushing of even more personalized digital content or therapeutics to boost mood, alleviate anxiety, reduce stress, and improve psychological health or mental fitness by directing users to follow procedures proven to increase the production of beneficial molecules and neurotransmitters like Dopamine, Oxytocin, Acetylcholine, Serotonin, and GABA to deliver positive mood and mind-altering effects.

Figure 21:
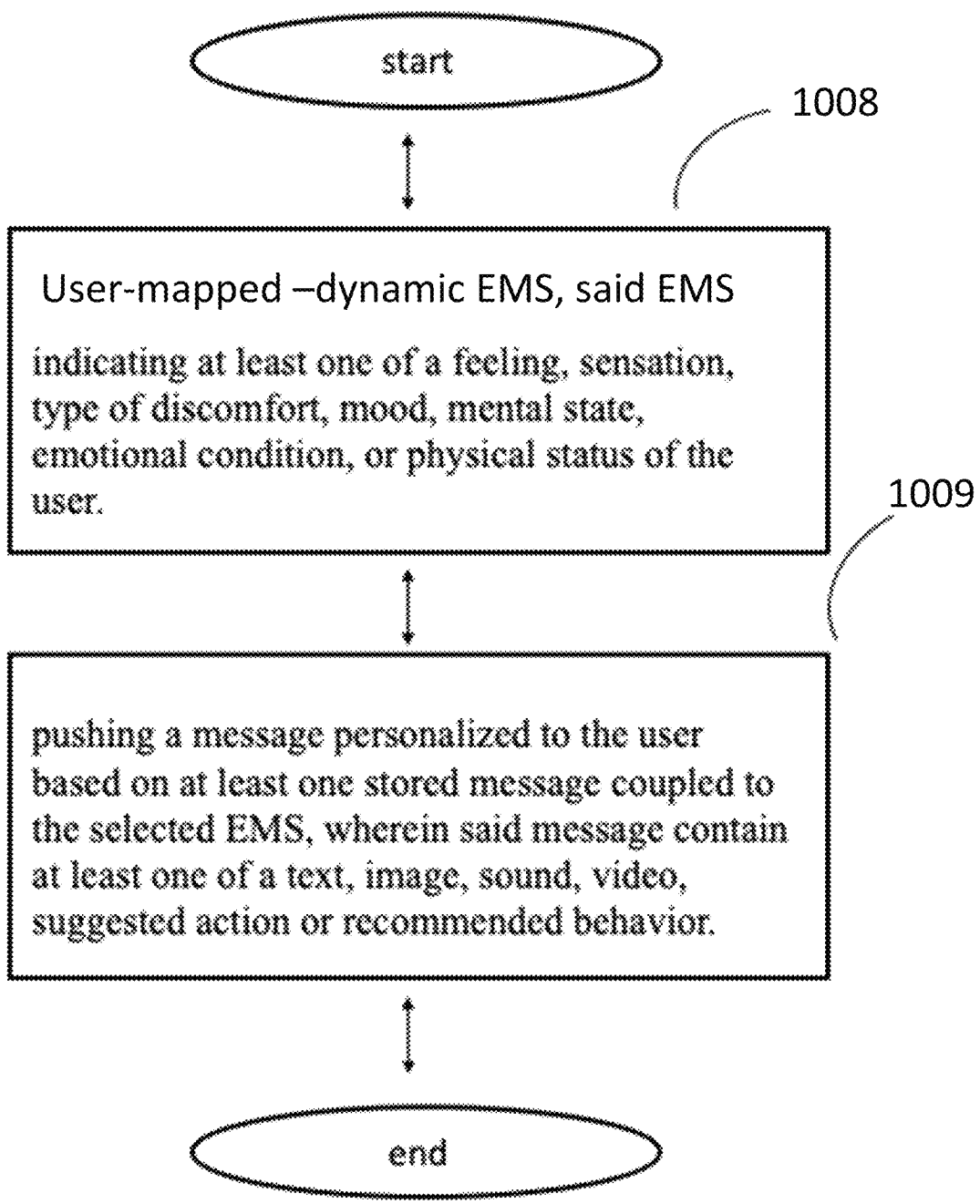
FIG. 21 illustrates a method flow chart for generating the hyper-personalized digital therapeutic pushed to the user-plotted dynamic EMS.

FIG. 21 illustrates a method flow chart for generating the hyper-personalized digital therapeutic pushed to the user-plotted dynamic EMS. The first step is: selecting at least one EMS for the user based on a user-plotted point on a displayed mood map to reflect at least a two-dimensional EMS along at least two correlates of behavior, said EMS indicating a granular assessment of at least one of a feeling, sensation, mood, mental state, emotional condition, or physical status of the user 1008; and step two entails delivering at least a primary-level message (digital therapeutic) personalized to the user based on at least one of a stored message coupled to the EMS 1009.

FIG. 22 illustrates a method flow chart for delivering an audio-based content (digital therapeutic or digital pharmaceutical) in accordance with an aspect of the invention. In a preferred embodiment, the method for delivering an audio-based digital therapeutic entails the steps of: (1) selecting at least one EMS for the user, in which the EMS indicates a granular assessment of at least one of a feeling, sensation, mood, mental state, emotional condition, or physical status of the user 1102; (2) choosing an audio-based digital therapeutic personalized to the user based on at least one of a stored message coupled to the selected EMS 1104; and finally (3) delivering said audio-based digital therapeutic to at least one of a user's device (mobile device, wearable, smart watch, tablet, desktop, laptop, headphones, or speaker) or home entertainment system in communication with at least one of the user's device or a voice-activated Internet-of-Things (IoT) hub 1106.

In a preferred embodiment, the audio-based digital therapeutic is at least one of a suggestion or recommendation for the user to perform a task or consume content with clinically proven benefits to address at least one of a mood, anxiety, stress, psychological state, emotional state, or physical state by altering levels of at least one neurotransmitter of the user. The content is tailored to alter at least one neurotransmitter comprised of at least one of Dopamine, Serotonin, Epinephrine, Endorphins, Norepinephrine, Endorphins, Adrenaline, Oxytocin, or GABA.

In one instance, a user-plotted or user-selected EMS on a smart watch or smart phone-configured interface may prompt a tailored curative audio-based content to be played-back via a users home entertainment system coupled to a home automation (IoT) hub (in turn, coupled to the users device and application. The user-plotted point may be on a one, two, or three dimensional circumplex-type graph (mood map or mood wheel) appearing on a smart-watch or mobile-phone configured interface. The user-selected EMS may be selected from a finger-scroll on a mobile-phone screen or smart watch. The user-selected EMS may also be selected by a scroll of a dial disposed on the side of a smart-watch. Furthermore, the content may be further annotated with efficacy and dosage labels. For instance, two distinct contents may be tailored to alter Dopamine levels in a user that has been assigned (diagnosed) with an EMS of depression/lethargy. However, since user 1 has been assigned (diagnosed) with a higher severity, user 1 may be delivered content specific to the EMS with a higher dosage and efficacy, versus the content delivered to user 2, who is experiencing a less severe form of depression/lethargy. An example of content with a higher dosage/efficacy may be content with a longer duration (120 seconds, versus 90 seconds, for instance) and, or content eliciting a stronger emotional response or a request to comply with a more strenuous physical task.

In another embodiment, the method may entail the steps of: (1) selecting at least one EMS for the user based on a user-plotted point on a displayed mood map to reflect at least a two-dimensional EMS along at least two correlates of behavior, said EMS indicating a granular assessment of at least one of a feeling, sensation, mood, mental state, emotional condition, or physical status of the user; (2) selecting an audio-based digital therapeutic personalized to the user based on at least one of a stored message coupled to the EMS; and (3) delivering said audio-based digital therapeutic to at least one of a user's device (mobile device, wearable, smart watch, tablet, desktop, laptop) or home entertainment system in communication with at least one of the user's device or a voice-activated Internet-of-Things (IoT) hub.

In yet another embodiment, the method may entail discerning at least one EMS for at least one user from a user-plotted point along a color wheel (mood wheel). In such an embodiment, the EMS may be selected/discerned by plotting a point on a perimeter of a displayed color wheel (mood wheel) comprising a gradient of colors, wherein each color is associated with a different EMS. The mood wheel may comprise two axis, wherein the first axis (outer perimeter of wheel) represents a first correlate of behavior, and the second axis (outer perimeter extending radially towards a center of the wheel) represents a second correlate of behavior. The plotted point represents two correlates of behavior that inform an EMS specific or hyper-personalized to the user. The user-plotted point on the mood wheel may displayed on the users device via an application interface. Preferably, the mood wheel may be displayed on an interface configured for small-form factor user devices, such as a smart watch, and the like. Given the small display/interface as a function of the small-form factor of a smart watch, other user-plotted methods/devices, such as the mood map, may not be preferable, although still used if necessary or preferred. In yet other embodiments, the EMS may be defined based on at least one of a stored, previous user-plotted point on the mood wheel, or previous selected EMS. In still yet other embodiments, the EMS may be selected by the user from a list/store of EMS—or from a list/store of EMS with a preview of associated content. Other embodiments may include discerning the appropriate EMS for a user based on vocal attributes or speech recognition.

It is preferable for the EMS to be discerned by a mood map, typically displayed on a users device, such as a smart phone. The mood maps x-axis is an activity correlate represented as an ocean surface horizontally bisecting the display, whereby a wave action increases the further right or left from a center point and the wave action calms further left or right from the center point. The mood maps y-axis is a positivity correlate represented as a sky above the ocean surface and ocean depth below the ocean surface, whereby the sky light becomes brighter (indicating positivity) the further up from the center point and the ocean depth becomes dimmer (indicating negativity) the further down from the center point (FIGS. 19B, 19C, 19D).

While not illustrated, other mood maps may be possible to discern a dynamic EMS, other than the animated ocean interface. In one embodiment, the x-axis may be at least one of an activity correlate or positivity correlate, different from the y-axis. For instance, the x-axis may be a positivity correlate, while the y-axis may be either an activity correlate or even a time correlate. In another embodiment, the x-axis may be an activity correlate, while the y-axis may b either a positivity correlate or time correlate. Any possible configuration of axis and behavior correlates may be possible. The x-axis may be represented as a gradient of one color, while the y-axis may be represented as a gradient of another color.

While also not illustrated, in some embodiments, the mood maps z-axis is a time or duration correlate, wherein the mood map shifts ninety degrees to reveal a side-sectional view of the ocean surface and shore, whereby the shore at either end of the display represents day zero and time or duration increases the further from the shore. Other correlates of behavior may be represented on any one of the two or three axis of the mood map, without departing from the scope of the invention.

The mood map/mapper may allow for a user to plot a single point on the x/y or x/y/z map, wherein each axis represents a unique and complementary behavioral attribute. In other embodiments, the user may plot multiple points on the x/y or x/y/z map to provide at least four behavioral attributes to inform a dEMS assessment by creating a coefficient, which may be eventually converted into at least one of a dEMS score, dEMS behavioral characteristic, d/EMS type, neurotransmitter implicated, treatment regimen, digital therapeutic type, etc. In other embodiments, at least one of a dEMS score, dEMS behavioral characteristic, d/EMS type, neurotransmitter implicated, treatment regimen, or digital therapeutic type may be derived without the need of a coefficient or algorithmically, statistically, probabilistically, or deep learned.

In yet other embodiments, the user may engage the mood map/mood mapper or mood wheel by finger-tip scrolling across the map/wheel and removing the finger to pinpoint the exact location of the circle/cursor point to define the at least two-axis correlates of behavior. In other embodiments, the user may finger-tip scroll across the map/wheel and double-tap to pinpoint the exact location of the circle/cursor point. In other embodiments, at least one of a dEMS score, dEMS behavioral characteristic, d/EMS type, neurotransmitter implicated, severity, treatment regimen (duration/efficacy), or digital therapeutic type may be derived algorithmically, statistically, probabilistically, or deep learned.

While not shown, a system for delivering a digital therapeutic, specific to a users emotional or mental state (EMS) is also provided. The system may comprise: a primary message prescriber; a processor coupled to a memory element with instructions, said processor when executing said memory-stored instructions, configure the system to cause: at least one EMS to be selected for the user, said EMS indicating a granular assessment of at least one of a feeling, sensation, mood, mental state, emotional condition, or physical status of the user; and the message prescriber delivering an audio-based digital therapeutic personalized to the user based on at least one of a stored message coupled to the EMS.

In some embodiments, the EMS is selected from at least one of a list/store from the user, by a mood map, or a mood wheel. Other embodiments for ascertaining/discerning/diagnosing an EMS may be possible, for instance, by vocal/speech recognition, or based on a user response from a single or series of diagnostic questions.

In some embodiments, once the EMS is diagnosed for user 1, an option may exist for user 1 to forward to at least a user 2. In other embodiments, the message prescriber may deliver an audio-based digital therapeutic to at least a second user based on a request by a first user, without performing an EMS diagnostic. In some embodiments, the audio-based digital therapeutic requested or selected is to be consumed (dosed) simultaneously by the first and at least the second user, wherein the first and second user are at least one of co-located or remotely located. For instance, after user 1 is diagnosed with a depression/lethargic EMS based on a user 1-plotted mood map, the message prescriber may push an audio content tailored for combatting the diagnosed EMS. User 1 may then have the option to forward to at least a user 2 for simultaneous consumption, despite user 1 and user 2 being continents apart. Simultaneous consumption providing for an enhanced or more rewarding effect due to the understanding that another person of your choosing is experiencing the same emotional cues at exactly the same time. In some embodiments, a pause in the playback from one of the users may cause a pause in the playback of the other user involved in the simultaneous consumption/dosing. For instance, upon user 1 receiving a call, the playback of the content is interrupted for both user 1 and user 2 simultaneously, until user 1 is ready to resume consumption. The requested, selected, or system diagnosed EMS and associated content (audio-based or visual-based) may be forwarded, simultaneously casted, separately casted, or simultaneously paused during interruption and only resumed upon either, or both, users ready for consumption.

While also not shown, in another embodiment, a system for delivering an identical digital therapeutic to at least two users, specific to at least a first and second user's emotional or mental state (EMS) may be provided. The system may comprise: a primary message prescriber; a processor coupled to a memory element with instructions, wherein the processor when executing said memory-stored instructions, configure the system to cause: at least one EMS to be selected for at least the first user and the second user, wherein the EMS indicates a granular assessment of at least one of a feeling, sensation, mood, mental state, emotional condition, or physical status of the at least two users. The message prescriber may deliver the identical digital therapeutic personalized to the at least first and second user based on at least one of a stored message coupled to the EMS and the identical digital therapeutic configured for at least one of a simultaneous playback or pause from the at least first and second users.

In some embodiments, the two users may be in a shared network or may be completely independent of each other. Once simultaneous dosing/consumption (of the audio or visual-based content) is complete, the two users may wish to further engage in simultaneous consumption of related content (audio-based or visual-based). Moreover, once the single or serial consumption is complete, a messaging platform may allow for the free exchange of communication between the two users. The platform or the system may also allow for the free exchange of other media—related or unrelated to the initial or subsequent single or serial consumption.

Map engagement and hyper-personalized digital therapeutic content may be pushed to any number of user devices, such as a smart phone, smart watch, tablet, smart tv, or any device with a display feature. Dynamic EMS (dEMS) assessment via the mood map and content pushing may be rendered/delivered identically across the ecosystem of devices. In other embodiments, the rendering/delivery may be specifically formatted based on the device form factor/configurations. For instance, a smart watch format may alter the map presentation, plot mechanisms, and EMS store. The pushed content on a smaller form factor, such as a smart watch, may feature more text-based, static imagery, haptic effects, as opposed to long-form animated or video content. Another user device may feature the use of a home automation vocal-based hub, configured to recognize natural based language input and output. In such embodiments, dEMS may be rendered from vocal tone or responses to targeted question/s. In other embodiments, dEMS may be user-selected. The hyper-personalized digital therapeutic in response to the rendered or user-selected dEMS may be an audio output of a select EMS type from an audio-based EMS store. The audio output may comprise at least one of a narrative, sound, song, tune, voice message, etc.

The claimed invention leverages existing clinical research and proven science (already published in peer-reviewed journals) and repackages insights as content modules or behavioral interventions that are simpler, more seductive, and profoundly more fun than traditional analogue therapies or digital treatment regimen. Described more simply, the system and platform curates existing digital content, and creates entirely new content programs, informed by and centered around techniques proven to boost mood, alleviate anxiety, reduce stress, and improve psychological health or mental fitness by directing users to follow procedures proven to increase the production of beneficial molecules and neurotransmitters like Dopamine, Oxytocin, Acetylcholine, Serotonin, and GABA to deliver positive mood and mind-altering effects. This is, in essence, a purely digital, transorbital drug delivery system. No pills. No powders.

Purely digital experiences to positively impact mood, mind and personal sense of well-being.

Figure 23A:
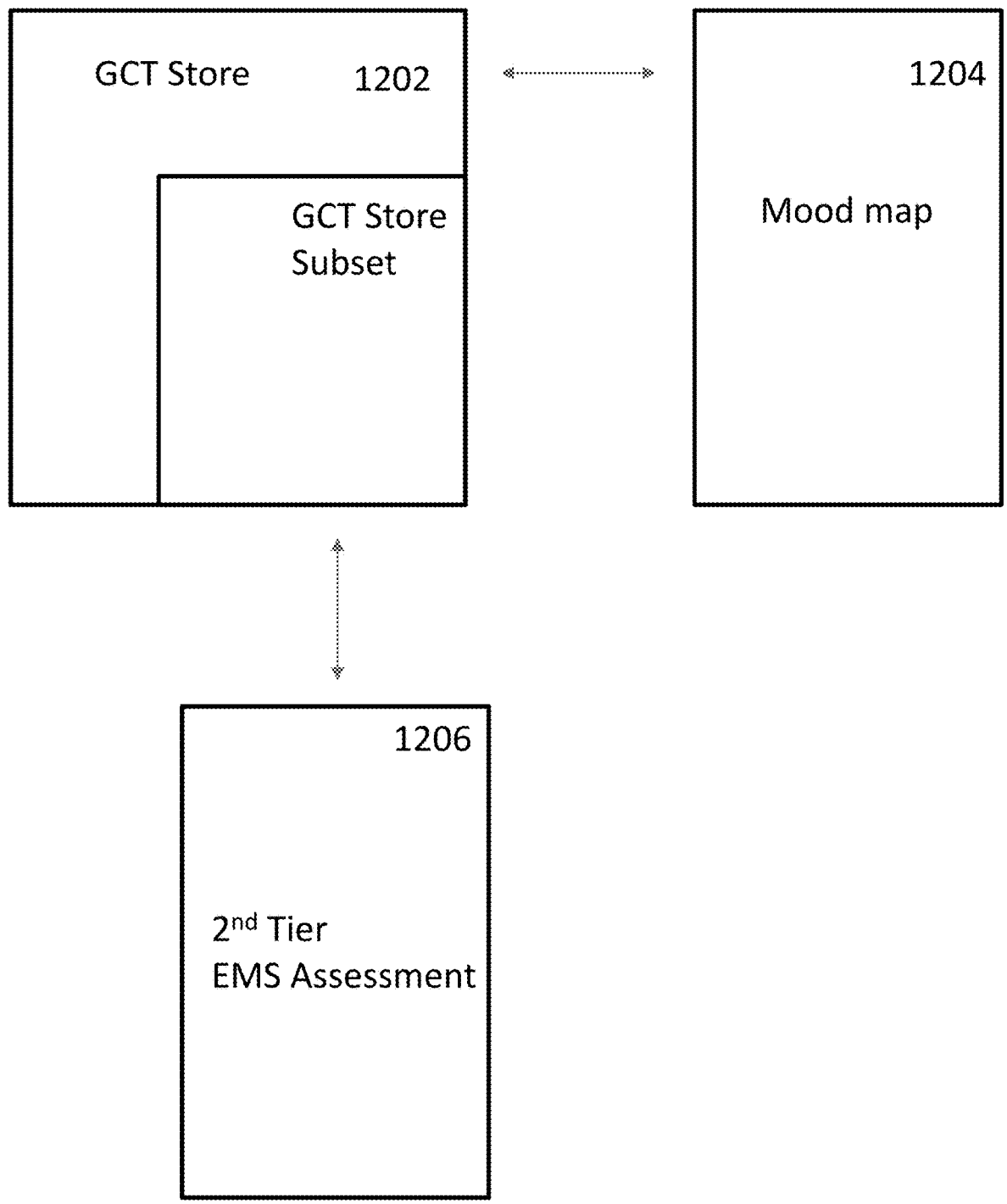
FIG. 23A is an exemplary system block diagram of the GCT delivery in accordance with an aspect of the invention.

Now in reference to FIG. 23A. FIG. 23A illustrates an exemplary system block diagram of the GCT delivery in accordance with an aspect of the invention. Illustrated is a preferred embodiment for a method for delivering generalized clinician tips (GCT), specific to a users emotional or mental state (EMS). In this preferred embodiment, the method comprises the steps of: fast-capturing of at least one EMS for the user based on at least one of a user-plotted point on at least one of a displayed mood map 1204 or mood wheel or user-selected from a menu. The EMS indicating an assessment of at least one of a feeling, sensation, mood, mental state, emotional condition, or physical status of the user. In other embodiments, the fast-capture also will ascribe (prescribe) the appropriate neurotransmitter (NT) associated with the user-selected EMS that requires addressing. By limiting the EMS to a specific handful of NT's, the assessment will be also fast-captured, rather than subjecting the user to the "paradox of choices". Exemplary NT's are Epinephrine, Norepinephrine, Endorphins, Acetylcholine, Dopamine, Serotonin, GABA, or Oxytocin—each NT corresponding to a unique EMS or a plurality of EMS. Conversely, an EMS may correspond to a unique NT or a plurality of NT's. Other NT's may be included beyond the NT's mentioned above.

Still in reference to FIG. 23A, delivering the GCT to at least one of a user's device (mobile device, wearable, smart watch, tablet, desktop, laptop, headphones, speaker, or smart speaker) or home entertainment system in communication with at least one of the user's device or a voice-activated Internet-of-Things (IoT) hub; and wherein the GCT is selected from a store of EMS-specific GCT 1202 and is at least one of a suggestion or recommendation for the user to perform a task with clinical-consensus benefits to address at least one of the EMS and/or NT. The GCT is a long-form, text-based medium with substantive clinician-approved recommendations or suggestions. The GCT may be coupled with visual assets or design elements, but the at the forefront will be the clinician-approved suggestions or recommendations in text form. It a suggestion or recommendation that has a consensus of at least two accredited clinicians. The intended response from the GCT is to primarily deliver a longitudinal behavioral response, such as helping someone quitting a vice, re-engaging with an estranged family member, or improving focus at the workplace, etc. Alternatively, the GCT may also be designed or peer-reviewed by a team of clinicians to deliver a more acute response. For instance, the GCT may be a shorter-form text of suggestions or recommendations to perform a task to address the assessed EMS and/or NT. An example of this would be a suggestion to stop current activity and walk around the block, while taking deep breaths and holding before exhaling. The GCT may go on further explaining the benefits of walking and deep breathing and how it elevates levels of Oxytocin, which is crucial for a sense of well-being and confidence. This type of short-form GCT, in contrast to the long-form, may be prescriptive for achieving an acute psychological or behavioral response, rather than a more longitudinal behavioral modification.

The GCT contrasts the short-burst digital therapeutic replete with design or visual assets. The short-burst digital therapeutic is a more social-based content intended to be fun and engage the user over a short span. The short-burst digital therapeutic or social-based digital content (sdc) may also comprise of a short recommendation or suggestion intended to achieve an acute psychological response by altering NT levels corresponding to the EMS selected.

In a preferred embodiment, the EMS may be defined based on a user-plotted or selected EMS. Alternatively, the EMS may be based on at least one of a stored or previous user-plotted or selected EMS. In order to achieve a fast-capture of EMS, at least one of the displayed mood map or mood wheel may be used. As described earlier, the mood map or wheel reflects at least one of a two-dimensional or three-dimensional EMS along at least two correlates of behavior. In alternate embodiments, a third correlate of behavior may be included, wherein the three correlates are a positivity correlate, an activity correlate, and a time correlate—for a more refined assessment.

As shown, the EMS may be further defined by the user answering curated questions and based on the answer ($2^{nd}$ tier-assessment 1206), the GCT is further limited from a subset of the GCT store 1202. In other embodiments, the $2^{nd}$-tier assessment 1206 may be achieved by tracking a user performance to at least one of physical or cognitive task. In yet other embodiments, the $2^{nd}$-tier assessment 1206 may be achieved by capturing or tracking a biometric measurable from the user.

In another embodiment, subsequent or series of GCT may be delivered based on at least one of the users measured or self-reported response to the first delivered GCT. For instance, an image, acoustic, heart rate, sweat, skin galvanic response capture means may be used to capture or measure a response to a first or prior GCT. Based on the measurable or response, a subsequent or series of GCT may be delivered accordingly. In one example, a user receives a recommendation for the benefits of consistent exercise on mental health and immediately displays micro-gestures suggesting an unwillingness. Based on the captured gestures, the subsequent or series of GCT will revise the recommendation to for a less strenuous activity, such as simply walking around the block.

Now in reference to FIG. 23B, which is an exemplary method flow chart of the GCT delivery in accordance with an aspect of the invention. The method for delivering generalized clinician tips (GCT), specific to a users emotional or mental state (EMS), the method comprising the steps of: (1) fast-capturing of at least one EMS for the user based on at least one of a user-plotted point on at least one of a displayed mood map or mood wheel or user-selected from a menu, said EMS indicating an assessment of at least one of a feeling, sensation, mood, mental state, emotional condition, or physical status of the user and categorized as at least one of Dopamine, Serotonin, Epinephrine, Norepinephrine, Acetylcholine, Oxytocin, or GABA neurotransmitters 1302; (2) delivering said GCT to at least one of a user's device (mobile device, wearable, smart watch, tablet, desktop, laptop, headphones, speaker, or smart speaker) or home entertainment system in communication with at least one of the user's device or a voice-activated Internet-of-Things (IoT) hub 1304; and (3) delivering said GCT from a subset of the GCT store based on the further defined EMS, wherein the GCT is selected from a store of EMS-specific GCT and is at least one of a suggestion or recommendation for the user to perform a task with clinical-consensus benefits to address at least one of the EMS and improve at least one of the associated neurotransmitters 1306.

In other embodiments, the user may perform at least one of answering at least one question, performing a physical task, conducting a cognitive task, or subjecting to at least one biometric measurable via an interface/sensor/capturing means to further define the at least one of the EMS and the at least one of the associated neurotransmitters ($2^{nd}$-tier assessment). The further defined EMS and/or neurotransmitter may deliver a more precisely tailored GCT specific to the users needs. In yet other embodiments, the delivered GCT may be coupled with delivery of at least one SDC. The SDC may be at least one of serial or parallel with the GCT. In other words, once the GCT is delivered, the at least one SDC may follow. Alternatively, the SDC and GCT may overlap/split a screen or screen-in-screen, analogous to picture-in-picture (PIP). In other embodiments, the SDC may premiere, followed by the GCT in any of the above mentioned screening configurations or sequences. In an embodiment, a communication module may deliver and, or display at least one of the GCT from at least one of a GCT store, GCT store subset, or SDC based on at least one of the EMS and/or NT.

Furthermore, in some embodiments, at least one of the GCT or social-based digital content is augmented by a member of a trusted shared network for further sharing within the network or to any of a social media site. The member of the trusted shared network may be enabled to suggest or push social-based digital content outside of the EMS store. Furthermore, the SDC may further comprise pushing at least one of a curated social media, news, sports feed based on the selected EMS and/or NT specific for the user.

Figure 24:
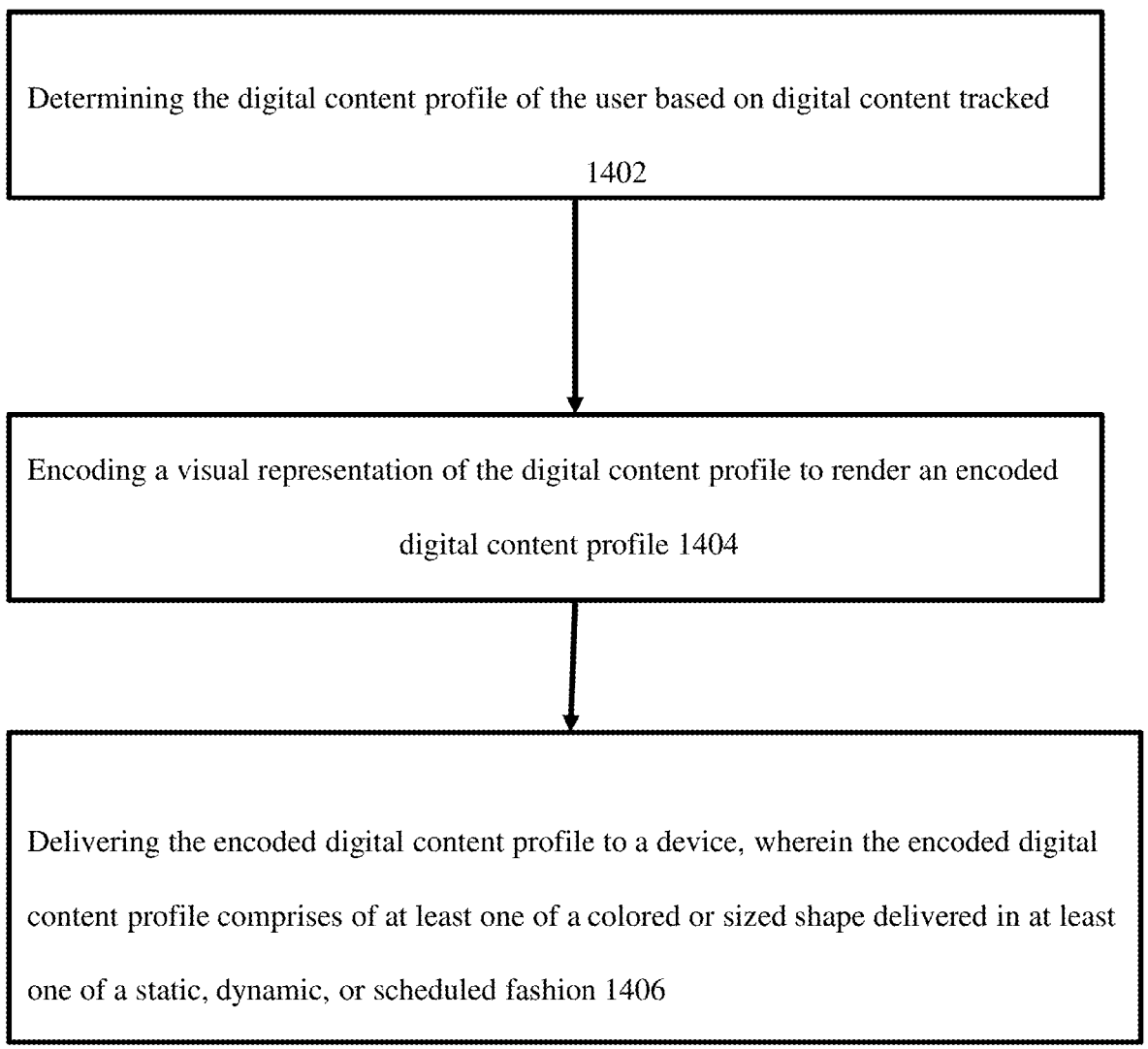
FIG. 24 is an exemplary method flow diagram detailing the steps in delivering an encoded profile to a user device in accordance with an aspect of the invention.

Now in reference to FIG. 24—depicting an exemplary method flow diagram detailing the steps involved in the delivery of an encoded EMS (emotional or mental state) profile or encoded mood profile to a user device. The encoded EMS profile or encoded mood profile may also be a profile based on digital content consumed (digital content/media diet). In one embodiment, a method for delivering an encoded digital content profile of a user to a device may comprise the steps of: determining the digital content profile of the user based on digital content tracked 1402; encoding a visual representation of the digital content profile to render an encoded digital content profile 1404; and delivering the encoded digital content profile to a device, wherein the encoded digital content profile comprises of at least one of a colored or sized shape delivered to the device in at least one of a logged-off, locked, or resting state 1406. The digital content tracked may be any and all digital content viewed on all user devices—across any and all platforms. Alternatively, the digital content tracked may be content viewed on a specific application or platform. Moreover, the tracking may simply be content played partially or completely, or more heavily rate for content that is interacted with by the user, such as forwarded or re-played.

The tracking may be achieved by any of the conventional methods known in the art, such as those used for developing marketing metrics. Alternatively, content—at the point of generation or curation—may be metadata tagged with a specific content identifier that may be referenced using a standardized look-up customized for EMS or NT (neurotransmitter) identification. As a result, content consumption for a user in a given period may be aggregated and parsed for EMS/NT type. The next step would be rating the parsed EMS/NT type and apportioning a color, a color intensity, or shape in a visual representation for device display. The overall visual map representing an encoded EMS or mood profile of the user based on his or her current or historical media/digital content consumption. Any number of other techniques for tracking content, such as crawling or fingerprinting, may be used to generate the encoded EMS or mood profile.

In another embodiment, the EMS or mood may be determined or assessed based on any number of other factors besides digital content viewed. For instance, an EMS or mood may be determined based on a recent or previous input of EMS/NT type by the user. Additionally, the EMS/NT type may be assessed based on a biometric or motion capture of the user. Leveraging an image capture or motion capture means of a device may allow the system to assess the user EMS/mood to generate the encoded profile for device display. While not shown in FIG. 24, a method for delivering an encoded emotional or mental state (EMS) profile of a user to a user device may comprise the steps of determining the EMS of the user based on at least one of a sensor-captured, data gathered, or previously user-selected input; and delivering an encoded visual representation of said EMS to a user device in at least one of a lock-screen or rest state.

Any number of conventional routines may be employed to instruct a device processor to display the encoded profile, as opposed to any one of the factory-set choices of screen-savers or lock-screen. In some embodiments, the EMS/mood profile may superimpose key information from factory-set screen, such as time, date, or temperature. The advantage of this profile serving as the rest or lock-screen on any device is that it is yet another fast-capture of the user mood snapshot pervasively displayed, without the need of the user to log in or access the application. It serves as a pervasive reminder to the user of the user mood, EMS, or media/content diet—allowing the user to make better informed decisions. These decisions may range from work-place and social interactions, to media consumption habits and social media posts. The profile may additionally inform the user of a more accurate assessment of EMS/NT for user input into the application for a better matched digital content pushed.

While also not illustrated in FIG. 24, the profile may be pushed in at least one of a static, dynamic, or scheduled fashion. While not logged on to the application, the profile may be pushed as or after content is viewed (dynamic fashion). Moreover, the profile may be pushed in a scheduled fashion, as per the scheduler preferences of the user. For instance, a user may prefer a profile sent three times a day, interspersed evenly, say at 11 am, 5 pm, and 11 pm. The static fashion is in reference to the system pushing the profile for display upon a device being in a rest or lock state. Any one of the dynamic or static fashion may also encompass for pushing a profile upon a triggered device or user event. For instance, a device event may be when the device transitions into a lock or rest state (screen-save), at which point a push of the profile as a rest or lock-screen is triggered. An example of a user event triggering a profile push may be when the user reaches his or her milestone of 10,000 steps or upon reaching a limit of 3 hours spent on social media.

Figure 25:
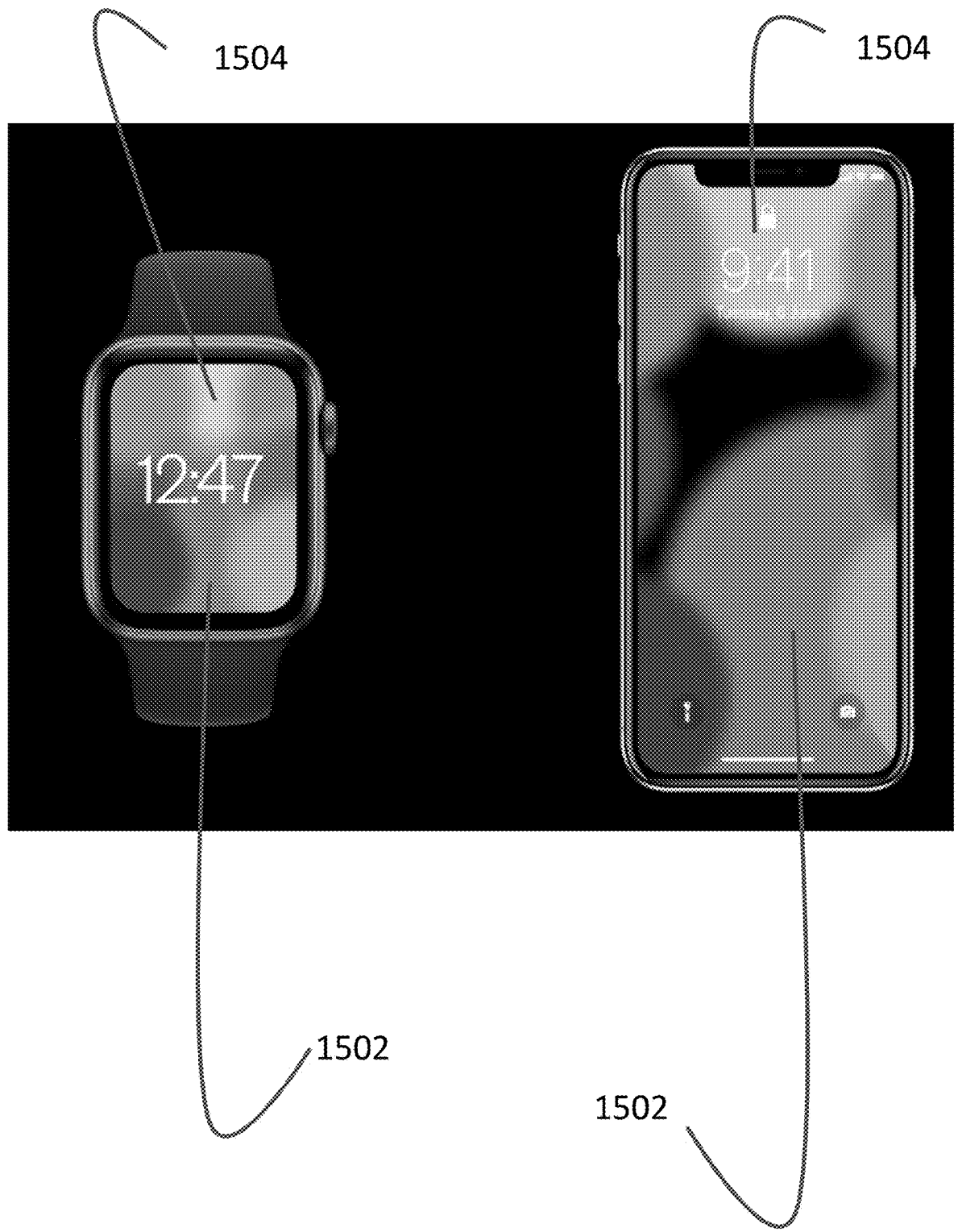
FIG. 25 is an exemplary encoded profile as displayed on a smart phone/watch in accordance with an aspect of the invention.
Figure 26:
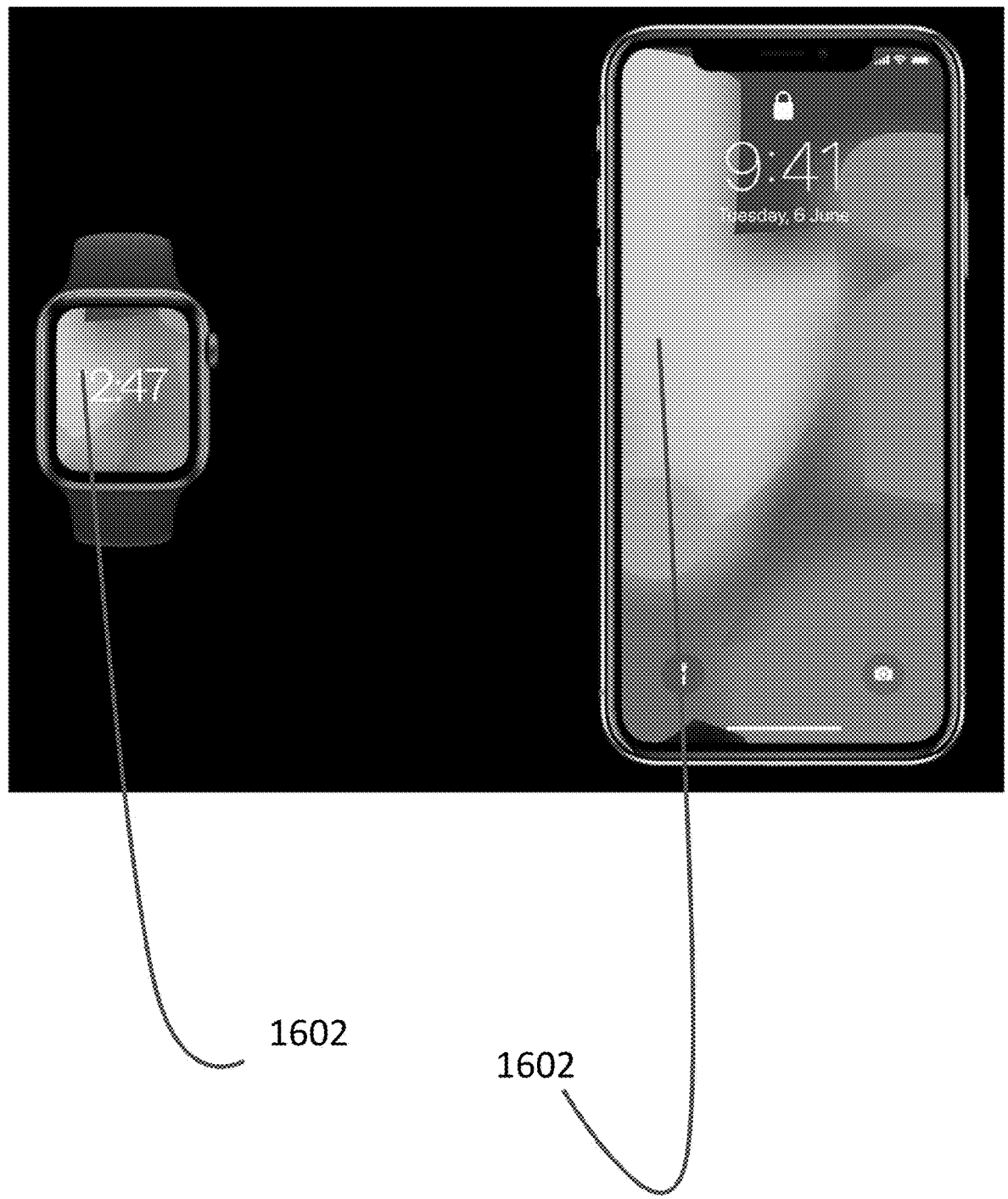
FIG. 26 is an exemplary encoded profile as displayed on a smart phone/watch in accordance with an aspect of the invention.

FIGS. 25 and 26 both illustrate an exemplary encoded profile as displayed on a smart phone and smart watch in accordance with an aspect of the invention. Each figure represents a different encoded profile, as depicted by the variation in the visual representation between FIG. 25 and FIG. 26. As depicted in FIGS. 25 and 26, the visual representation is primarily composed of a series of conjoined, separated, or overlapping circles of varying sizes and colors. Any standardized rule may be used to decode the representation. Moreover, any standardized table of colors and symbols representing EMS or NT may be used for application of the rule.

In one embodiment, based on the total time of a user viewing content—across the primary device or across any and all devices (tablet, phone, smart watch, home hub, speakers)—the EMS or NT type of the content will be captured and indicate the overall chemical footprint or exposure profile of the user via the encoded profile. As illustrated in FIGS. 25 and 26, the encoded profile is displayed on each of a smart phone or smart watch. As shown in both figures, the circles are of varying size and shape.

Representative Table of Color/Symbols

Dopamine/associated EMS—Purple;
Endorphins/EMS—Red;
Testosterone/EMS—Klein Blue;
Oxytocin/EMS—Pink;
Acetylcholine/EMS—Green;
GABA/EMS—Light Blue;
Serotonin/EMS—Yellow;
Experimental Medicine/EMS—Hot Pink It should be appreciated that any combination of EMS/NT and colors/symbols may be paired. For instance, Dopamine may be represented as purple or as a purple square. This purple square may additionally be displayed on any generated, curated, or uploaded content as a way to label the content with a digital nutrition label. In the context of FIGS. 25 and 26, circles are used as a fixed symbol and EMS/NT are distinguished purely on a color basis. Likewise, the encoded profile may be composed of colored shapes to distinguish EMS/NT, or simply as blank shapes.

In both figures, the colored circles appear in various sizes—indicating a percentage of total time spent consuming or exposed to content of a particular labeled EMS/NT. In other embodiments, the encoded profile may be based on a sensor-captured input or a user input to denote a current or a rolling profile of a user EMS/mood. As shown in FIG. 25, the predominant circle displayed is green 1502 corresponding to Acetycholine (ACh) based on our representative color/symbol table, followed by yellow 1504 corresponding to Serotonin (5-HT3). ACh is a neurotransmitter that has been known to be associated with higher cognitive functioning, such as focusing. ACh is the NT corresponding to the EMS or mood related to focus or addressing a need to focus more. Based on a representative rule for decoding colors/symbols, the large green circle 1502 may indicate to a user that the assessed or determined EMS of the user or tracked content of the user implicates the NT ACh and the EMS of focus. As a result, a user may heed the indication and be more mindful of off-line interactions, on-line interactions, or future consumption of content. The user may be nudged to be less absent-minded during his or her day-to-day activities, as well as consciously consume content or make an active effort to only consume content labeled with ACh (green half-circle). Alternatively, the large green circle 1502 prominently displayed on ones encoded profile may nudge the user to actively avoid any content labeled as ACh, since the profile already indicates a high level of focus or tracked content implicating focus.

In contrast, FIG. 26 shows an encoded profile featuring a large yellow circle 1602 indicative of the EMS/NT of Serotonin/Happiness. Serotonin (5-HT3) is the NT associated with feelings of well-being and happiness. The inhibition of serotonin (5-HT3) re-uptake is the pharmacological approach to addressing clinical depression. As shown in FIG. 26, the large yellow circle 1602 may indicate to a user that the assessed or determined EMS of the user or tracked content of the user implicates the NT 5-HT3 and the EMS of happiness. As a result, a user may heed the indication and be more mindful of off-line interactions, on-line interactions, or future consumption of content. The user may be nudged to be less pessimistic during his or her day-to-day activities, as well as consciously consume content or make an active effort to only consume content labeled with Serotonin (yellow full-circle). Alternatively, the large yellow circle 1602 prominently displayed on ones encoded profile may nudge the user to actively avoid any content labeled with Serotonin (yellow full-circle), since the profile already indicates a high level of happiness or tracked consumption of content implicating happiness.

In some embodiments, another rule for decoding may be provided, in which in addition to color and size, placement on the screen may imply a significance. Placement on the screen may confer a qualitative value for EMS/NT intensity, as opposed to just duration of consumption. For instance, a small yellow circle in the center of the encoded profile may suggest that while the user has consumed content labeled Serotonin/5-HT3/Happiness for a short duration, the content consumed was intense. An example of intense content may be a toddler riding the back of a large dog and chuckling uncontrollably. While the content was short, it was rated or labeled intensely for being strongly related to Serotonin/Happiness—hence the small yellow circle featured at the center of the encoded profile. In contrast, a small yellow circle featured on the margins of the encoded profile may suggest a short-duration of happy content with low intensity. For instance, a quick glance of a picture of an employee or acquaintance, who the user isn't exactly indifferent towards, but who doesn't exactly invoke any overwhelmingly positive feelings for the user either. This placement variable in the decoding rule may also apply to determined or assessed EMS/NT and not strictly for tracked digital content. The assessed or determined EMS/NT from sensor-captured, data-gathered, or user-selected input may also drive the specific placement of the colored shape/s to encode for intensity.

In another embodiment, the user may drag any one of the shapes to set a preferred EMS profile. This may result in a goal-set and notify the user of a degree of match with the dragged profile. In one embodiment, a change in profile over a time-at-a glance may be visually depicted with a time-lapse. In yet another embodiment, a user may be able to view his or her profile or changes in his or her profile by time, day, or month. In another embodiment, a user may tap on any of the circles or shapes, revealing the total amount of EMS/NT content exposure. Exposure may be expressed in terms of time exposed or percentage of total screen time—and may be displayed over the tapped circle, or displayed on a dedicated screen. Other embodiments enable a user to tap over any of the circles or shapes, resulting in a menu of content titles or a thumbnail menu of content viewed corresponding to the colored circle or shape tapped. Additionally, the user may select any of the drop-down menu titles or thumbnail menu content for preview or playback.

Profiles may additionally be displayed over a tablet or screen configured for display outside of an office or cubicle to fellow employees/co-workers. This profile may help guide and better inform office interactions and work-flow decisions, serving as a powerful human-resource tool. Staff-wide management of work load may be achieved by a profile management program. For instance, if a manager detects a profile indicative of focus-issues for a particular employee, the manager may then elect to relieve the employee of any attention-oriented tasks.

The profile may also be displayed on the outward-facing display of a two-way or foldable smart phone or tablet. The profile may be a cue to a concerned on-looker, friend, or family member for approaching and engaging in a social interaction or soft-intervention of sorts. On the other hand, an on-looker, friend, or family member may view the profile and provide much needed affirmation and support to the user.

Embodiments are described at least in part herein with reference to flowchart illustrations and/or block diagrams of methods, systems, and computer program products and data structures according to embodiments of the disclosure. It will be understood that each block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus, to produce a computer implemented process such that, the instructions which execute on the computer or other programmable apparatus provide steps for implementing the functions/acts specified in the block or blocks.

In general, the word "module" as used herein, refers to logic embodied in hardware or firmware, or to a collection of software instructions, written in a programming language, such as, Java, C, etc. One or more software instructions in the unit may be embedded in firmware. The modules described herein may be implemented as either software and/or hardware modules and may be stored in any type of non-transitory computer-readable medium or other non-transitory storage elements. Some non-limiting examples of non-transitory computer-readable media include CDs, DVDs, BLU-RAY, flash memory, mobile device, remote device, and hard disk drive.

I claim:

1. A method for delivering an encoded visual representation of an emotional or mental state (EMS) profile of a user to a device, when the device is in a logged-off, locked, or resting state from an application, said method comprising the steps of:
    determining an EMS of the user based on at least one of a sensor-captured input, data gathered input, or user-selected input;
    delivering the encoded visual representation in at least one of static, dynamic, or scheduled fashion, wherein the encoded visual representation is at least one shape of varying size, color, or color intensity, wherein the at least one shape of varying size, color, or color intensity denotes at least one of EMS types or severity of EMS types; and
    wherein the EMS types or severity of EMS types indicates the user's digital content diet.

2. The method of claim 1, wherein an EMS that is determined based on the data gathered input is based on digital content viewed on the user device.

3. The method of claim 1, wherein an EMS that is determined based on sensor-captured input is based on an extent of activity monitored.

4. The method of claim 1, wherein an EMS that is determined based on the user-selected input is based on a most recently inputted EMS.

5. The method of claim 1, wherein the encoded visual representation is a plurality of shapes of varying size, color, or color intensity.

6. The method of claim 1, wherein a placement of at least one shape on the visual representation denotes EMS types or severity of EMS types.

7. The method of claim 1, wherein at least one shape of varying size, color, or color intensity denote a digital content diet of at least one of a current diet or historical diet.

8. The method of claim 1, wherein overlapping of shapes denote digital content corresponding to more than one of multiple EMS types.

9. The method of claim 1, wherein proximal placement of shapes denote different and related digital content, wherein each of the different content have a unique EMS type.

10. The method of claim 1, wherein the encoded visual representation is delivered in a static fashion, wherein the static fashion is at least one of a fixed increment of time or a fixed event.

11. The method of claim 1, wherein the encoded visual representation is delivered in a dynamic fashion based on at least one of an updated EMS, recently viewed content, or content being currently viewed.

12. The method of claim 1, wherein the scheduled fashion is based on a user's preference for at least one of a time preference or a format preference.

13. The method of claim 1, wherein the device is at least one of a smart phone, smart watch, tablet, television, laptop, desktop, or home entertainment hub.

14. The method of claim 1, wherein the device is at least one of a tablet or screen display configured for display in or out of at least one of an office or cubicle.

15. The method of claim 1, wherein the device is a screen display configured for public display.

16. The method of claim 1, wherein the device is a foldable smartphone configured for outward display of the encoded visual representation.

17. The method of claim 16, wherein the outward display causes a further digital interaction.

18. A method for delivering an encoded visual representation of an emotional or mental state (EMS) profile of a user to a device, said method comprising the steps of:
    determining an EMS of the user based on at least one of a sensor-captured input, data gathered input, or previously user-selected input;
    delivering the encoded visual representation to a user device in at least one of a lock-screen or rest state, wherein the encoded visual representation is at least one shape of varying size, color, or color intensity, wherein the at least one shape of varying size, color, or color intensity denotes at least one of EMS types or severity of EMS types; and
    wherein the EMS types or severity of EMS types indicates the user's digital content diet.

19. The method of claim 18, wherein the user may drag at least one shape to set a preferred EMS profile.

20. The method of claim 19, wherein a notification is pushed indicating degree of match with the preferred EMS profile.

21. The method of claim 18, wherein a change in the EMS profile over a period of time is visually depicted with a time-lapse.

* * * * *